(12) United States Patent
Martinsson et al.

(10) Patent No.: US 11,963,963 B2
(45) Date of Patent: Apr. 23, 2024

(54) 6-HETEROCYCLYL-4-MORPHOLIN-4-YLPYRIDINE-2-ONE COMPOUNDS USEFUL FOR THE TREATMENT OF CANCER AND DIABETES

(71) Applicant: Sprint Bioscience AB, Huddinge (SE)

(72) Inventors: Jessica Martinsson, Huddinge (SE); Martin Andersson, Huddinge (SE); Johan Lindström, Huddinge (SE); Rickard Forsblom, Huddinge (SE); Fredrik Rahm, Huddinge (SE); Tobias Ginman, Huddinge (SE); Jenny Viklund, Huddinge (SE)

(73) Assignee: Sprint Bioscience AB, Huddinge (SE)

( * ) Notice: Subject to any disclaimer, the term of this patent is extended or adjusted under 35 U.S.C. 154(b) by 55 days.

(21) Appl. No.: 17/501,407

(22) Filed: Oct. 14, 2021

(65) Prior Publication Data
US 2022/0175788 A1 Jun. 9, 2022

Related U.S. Application Data

(63) Continuation of application No. 15/999,432, filed as application No. PCT/EP2017/053614 on Feb. 17, 2017, now Pat. No. 11,179,399.

(30) Foreign Application Priority Data

Feb. 19, 2016 (EP) ................................ 16156533

(51) Int. Cl.
| A61K 31/5377 | (2006.01) |
| A61K 31/4745 | (2006.01) |
| A61K 31/5386 | (2006.01) |
| A61K 31/541 | (2006.01) |
| A61K 33/243 | (2019.01) |
| A61K 45/06 | (2006.01) |
| A61P 35/00 | (2006.01) |
| C07D 401/04 | (2006.01) |
| C07D 413/14 | (2006.01) |
| C07D 417/14 | (2006.01) |

(52) U.S. Cl.
CPC ...... *A61K 31/5377* (2013.01); *A61K 31/4745* (2013.01); *A61K 31/5386* (2013.01); *A61K 31/541* (2013.01); *A61K 33/243* (2019.01); *A61K 45/06* (2013.01); *A61P 35/00* (2018.01); *C07D 401/04* (2013.01); *C07D 413/14* (2013.01); *C07D 417/14* (2013.01)

(58) Field of Classification Search
None
See application file for complete search history.

(56) References Cited

U.S. PATENT DOCUMENTS

| 8,846,670 B2 | 9/2014 | Bacque et al. |
| 11,179,399 B2 * | 11/2021 | Martinsson ............. A61P 43/00 |
| 11,633,403 B2 * | 4/2023 | Martinsson ........ A61K 31/4745 |
| | | 514/235.2 |
| 2014/0275003 A1 | 9/2014 | Barsanti et al. |

FOREIGN PATENT DOCUMENTS

| WO | WO-2004/048365 A1 | 6/2004 |
| WO | WO-2010/052569 A2 | 5/2010 |
| WO | WO-2011/001113 A2 | 1/2011 |
| WO | WO-2013/190510 A2 | 12/2013 |
| WO | WO-2014/151616 A1 | 9/2014 |
| WO | WO-2015/030057 A1 | 3/2015 |
| WO | WO-2016/044662 A1 | 3/2016 |

OTHER PUBLICATIONS

Aggarwal et al., "Reaction of α-Ketoketene S, N-Acetals with Cyanoacetamide: A New General Method for Substituted and Fused 4-(N-Alkylamino-, N-Arylamino-, or N-Morpholino)-3-cyano-2(1H)-pyridones", Synthesis, 1982, 1982(3): pp. 214-216.

Coffman et al., "6-Amino-4-(pyrimidin-4-yl)pyridones: Novel glycogen synthase kinase-3b inhibitors", Bioorganic & Medicinal Chemistry Letters, 2011, 21: pp. 1429-1433.

Roedig et al., "Nucleophile Substitutionen am (Z)-Perchlor-1,3-butadien-1-carbonitril mit Natriumphemolat und sekundären aliphatischen Aminen", Chemische Berichte, 1982, 115(5): pp. 1733-1738, XP055269826, DE.

* cited by examiner

*Primary Examiner* — Brian J Davis
(74) *Attorney, Agent, or Firm* — Flaster Greenberg P.C.

(57) ABSTRACT

The invention provides novel 6-heterocyclyl-4-morpholin-4-yl-pyridine-2-one compounds of formula (I), pharmaceutical compositions containing such compounds, and methods for using such compounds in treatment of diseases including cancer, diabetes, inflammatory disease, neurodegenerative disorders, cardiovascular disorders and viral infections;

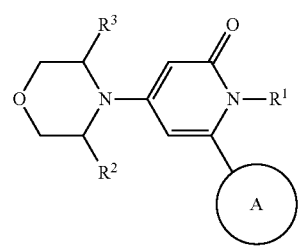

wherein $R^1$, $R^2$, $R^3$ and A are as defined in the specification.

20 Claims, No Drawings

6-HETEROCYCLYL-4-MORPHOLIN-4-YLPYRIDINE-2-ONE COMPOUNDS USEFUL FOR THE TREATMENT OF CANCER AND DIABETES

CROSS-REFERENCE TO RELATED APPLICATIONS

This application is a continuation of U.S. patent application Ser. No. 15/999,432, filed Aug. 17, 2018, which is a U.S. National Phase of International Application No. PCT/EP2017/053614 filed Feb. 17, 2017, which claims priority to EP Application No. 16156533.8 filed Feb. 19, 2016, each of which is hereby incorporated by reference in their entirety.

FIELD OF THE INVENTION

The invention provides novel 6-heterocyclyl-4-morpholin-4-yl-pyridine-2-one compounds of formula (I), to pharmaceutical compositions containing such compounds, and to methods for using such compounds in treatment of diseases including cancer and diabetes.

BACKGROUND OF THE INVENTION

Enzymes belonging to the family of phosphatidylinositide 3-kinases (PI3K) are regulators of several important cellular events. The family consists of three classes, I, II and III and while the Class I group has been an interesting drug target for many years, Class II and III are less exploited. The PI3K Class III, vacuolar protein sorting 34 (Vps34, PIK3C3) forms a heterodimer with its regulatory subunit p150 (Vps15) and this dimer takes part in several complexes regulating vesicular trafficking events such as autophagy, endocytosis, exocytosis and micropinocytosis (Amaravadi et al. Clin Cancer Res. 2011, 17:654-666; Carpentier et al. 2013, Traffic). The enzyme is responsible for phosphorylation of phosphatidylinositol (PI) to phosphatidylinositol (3)-phosphate (PI3P). The ligand binding to PX and FYVE domains results in recruiting and delocalization of these effector proteins that lead to vesicular formation, elongation and movement (Backer et al. J Biochem. 2008, 410:1-17).

Autophagy is a catabolic process where cellular components are targeted for degradation by enclosing them in double-membrane vesicles, autophagosomes that are fused with the protease-containing lysosomes. This is a mean for the cell to handle damaged organelles and misfolded proteins and by that maintain cellular function. The pathway is also a way of recirculating cellular content into new building blocks (Boya et al, Nat Cell Biol 2013, 15; 713-720). Autophagy is a cellular response to stressful conditions as nutrient deprivation, acidosis and hypoxia but also to drug treatment. Therefore, autophagy inhibition is a means to potentiate cancer drugs and resensitize drug resistant tumors (Nagelkerke et al, Semin Cancer Biol 2014, 31; 99-105). Most advanced tumors show a high upregulation of autophagic flux (Leone et al. Trends in Endocrin Metab 2013, 24; 209-217). An established marker for studying autophagic flux is the detection of autophagic puncta in the form of lipidated LC3 protein on the autophagosome. Inhibition of Vps34 results in the inhibition of autophagy as measured by LC3 redistribution into puncta (Dowdle et al., Nat Cell Biol 2014, 16; 1069-79).

As recently described, ablation of the regulatory subunit p150 leads to increased insulin sensitivity in vivo due to decreased insulin receptor internalization (Nemazanyy, Nature Commun., 2015, 6:8283). A kinase dead heterozygous animal model confirms this result with increased glucose tolerance and increased insulin sensitivity (WO2013076501).

Several disease states could benefit from Vps34 inhibition including cancer, inflammatory diseases, neurodegenerative disorders, cardiovascular disorders, diabetes and viral infections (Reviewed in Rubinsztein et al, Nat Rev 2012, 11; 709-730). Cancer forms that would benefit from Vps34 inhibition include, but are not limited to, triple negative breast cancer, pancreas cancer, leukemia, melanoma and lung cancer. There is thus a need for novel and potent inhibitors of Vps34.

Previous disclosures describing Vps34 inhibitors in use to affect diseases include WO2015150555; WO2015150557; WO2015108861; WO2015108881; WO2012085815; WO2012085244; WO2013190510; Farkas, J. Biol. Chem., 2011 286(45) 38904-12.

DESCRIPTION OF THE INVENTION

An object of the invention is to provide novel and potent inhibitors of Vps34. Another object of the invention is to provide novel and potent inhibitors of Vps34 that may be used for treating cancer and other diseases such as diabetes.

According to one aspect of the invention, there is provided a compound of Formula (I)

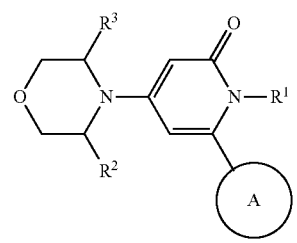

wherein
$R^1$, $R^2$ and $R^3$ are independently selected from hydrogen, $C_1$-$C_3$haloalkyl and $C_1$-$C_3$alkyl;

A represents

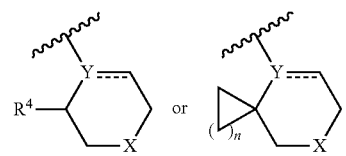

wherein
X represents $CH_2$, S, SO, $SO_2$, $NR^5$, $NCOR^5$, $NCOR^9$, $NCOCH_2R^9$, O, or a bond;
Y represents N, CH or C;
n is selected from 1, 2, 3 and 4;
$R^4$ is selected from hydrogen, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl and heteroaryl, wherein said aryl and said heteroaryl are optionally substituted with one or more $R^1$;
$R^5$ is selected from hydrogen, $C_1$-$C_3$fluoroalkyl, $C_1$-$C_3$alkyl, $C_1$-$C_3$alkoxy$C_1$-$C_3$alkyl and $C_3$-$C_6$cycloalkyl;

R⁶ is selected from C₁-C₃alkoxy, N—C₁-C₃alkylamino, N,N-diC₁-C₃alkylamino, 1-pyrrolidinyl, 1-piperidinyl and 1-azetidinyl;

R⁷ is selected from C₁-C₆alkyl, C₃-C₆cycloalkyl, C₁-C₃alkoxyC₁-C₃alkyl, C₁-C₃haloalkyl, halogen, N—C₁-C₃alkylamino, N,N-diC₁-C₃alkylamino, C₁-C₃haloalkoxy and C₁-C₃alkoxy;

R⁹ is selected from C₁-C₃alkyl, C₁-C₃alkoxy, C₃-C₆cycloalkyl, heterocyclyl, phenyl and a monocyclic heteroaryl, wherein said heterocyclyl, said phenyl and said monocyclic heteroaryl are optionally substituted with one or two R⁸;

R⁸ is selected from halogen, C₁-C₃haloalkyl and C₁-C₃alkyl; and pharmaceutically acceptable salts, stereoisomers and tautomers thereof.

In one embodiment of this aspect, R⁴ is selected from hydrogen, halogen, COR⁶, C₁-C₆alkyl, C₁-C₃alkoxyC₁-C₃alkyl, C₁-C₆alkoxy, C₃-C₆cycloalkyl, C₁-C₃cyanoalkyl, C₁-C₃haloalkyl, aryl and heteroaryl, wherein said aryl and said heteroaryl are optionally substituted with one or more R⁷.

In one embodiment of this aspect, Y is N.

In one embodiment of this aspect, R¹ and R³ are independently selected from hydrogen and methyl.

In one embodiment of this aspect, R² is hydrogen.

In one embodiment of this aspect, R¹ is hydrogen.

In one embodiment of this aspect, R³ is methyl.

In one embodiment of this aspect, R³ is hydrogen.

In one embodiment of this aspect, R⁵ is C₁-C₃alkyl.

In one embodiment of this aspect, R⁶ is N—C₁-C₃alkylamino or N,N-diC₁-C₃alkylamino, such as N,N-diC₁-C₃alkylamino.

In one embodiment of this aspect, R⁶ is dimethylamino.

In one embodiment of this aspect, R⁷ is selected from halogen, C₁-C₃fluoroalkyl, C₁-C₃fluoroalkoxy, C₁-C₃alkoxy, C₁-C₃alkyl, C₃-C₆cycloalkyl and N,N-diC₁-C₃alkylamino.

In one embodiment of this aspect, R⁷ is selected from fluorine, chlorine, trifluoromethyl, trifluoromethoxy, methoxy, methyl, ethyl, cyclopropyl and dimethylamino.

In one embodiment of this aspect, R⁹ is selected from C₁-C₃alkoxy, heterocyclyl, phenyl and a monocyclic heteroaryl, wherein said heterocyclyl, said phenyl and said monocyclic heteroaryl are optionally substituted with one or two R⁸.

In one embodiment of this aspect, R⁹ is selected from heterocyclyl, phenyl and a monocyclic heteroaryl, wherein said heterocyclyl, said phenyl and said monocyclic heteroaryl are optionally substituted with one or two R⁸.

In one embodiment of this aspect, R⁹ is selected from tetrahydrofuryl, phenyl and pyridyl, each optionally substituted with one or two R⁸.

In one embodiment of this aspect, R⁸ is halogen.

In one embodiment of this aspect, said monocyclic heteroaryl in R⁴ is selected from pyridyl, furyl, isoxasolyl, pyrazolyl and thiazolyl, each optionally substituted with one or more R⁷.

In one embodiment of this aspect, R⁴ is selected from

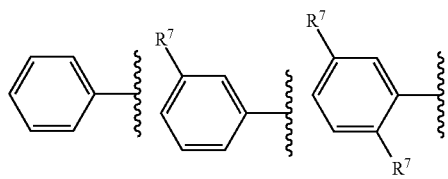

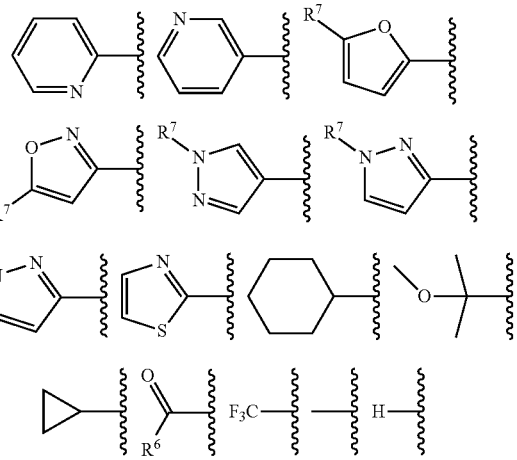

In one embodiment of this aspect, R⁷ is selected from fluorine, chlorine, C₁-C₃alkoxy, C₁-C₃fluoroalkoxy, C₁-C₃fluoroalkyl, C₃-C₆cycloalkyl, N,N-diC₁-C₃alkylamino.

In one embodiment of this aspect, R⁷ is selected from fluorine, chlorine, methyl, ethyl, methoxy, trifluoromethoxy, trifluoromethyl, cyclopropyl and N,N-dimethylamino.

In one embodiment of this aspect, X represents a bond.

In one embodiment of this aspect, R⁴ is selected from

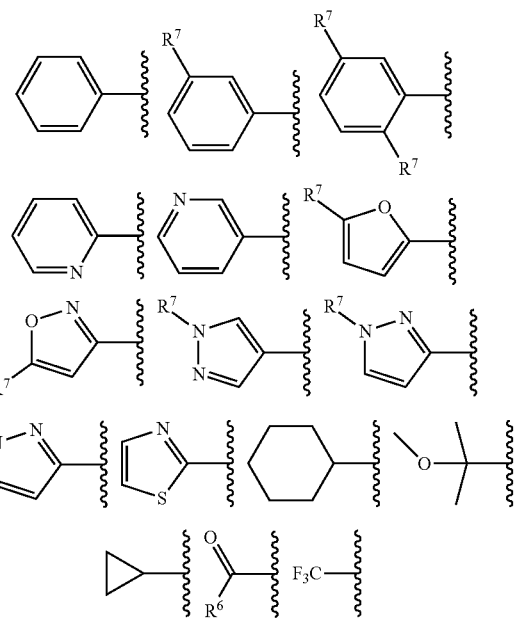

In one embodiment of this aspect, A represents:

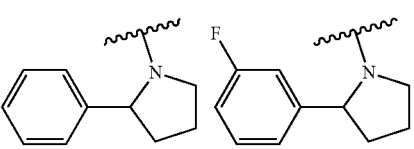

-continued

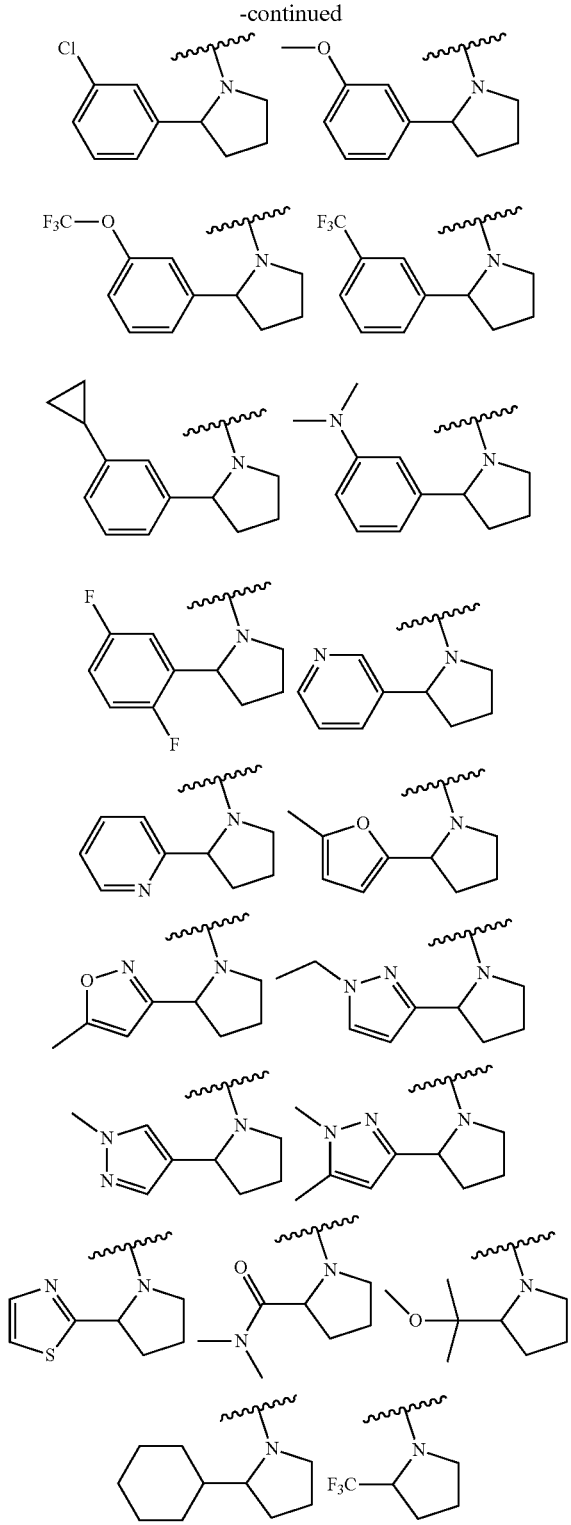

In one embodiment of this aspect, X represents CH$_2$, SO, SO$_2$, NR$^5$, NCOR$^5$, NCOR$^9$, NCOCH$_2$R$^9$ or O; and R$^5$ is C$_1$-C$_3$alkyl.

In one embodiment of this aspect, R$^4$ is selected from hydrogen, C$_1$-C$_6$alkyl, C$_3$-C$_6$cycloalkyl, C$_1$-C$_3$haloalkyl and phenyl, wherein phenyl is optionally substituted with one or more R$^7$.

In one embodiment of this aspect, A represents:

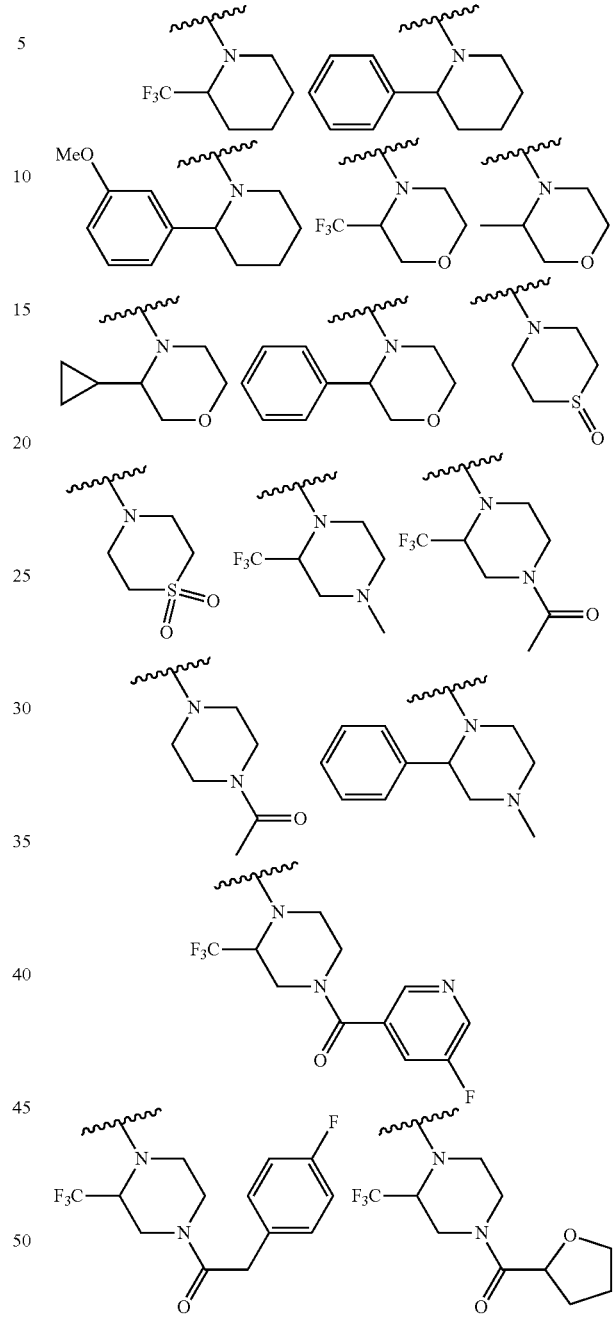

In one embodiment of this aspect,

X represents CH$_2$, SO, SO$_2$, NR$^5$, NCOR$^5$, NCOR$^9$, NCOCH$_2$R$^9$, O, or a bond;

R$^4$ is selected from hydrogen, COR$^6$, C$_1$-C$_3$alkyl, methoxyC$_1$-C$_3$alkyl, C$_3$-C$_6$cycloalkyl, C$_1$-C$_3$fluoroalkyl, phenyl and a monocyclic heteroaryl, wherein said phenyl and said monocyclic heteroaryl are optionally substituted with one or two R$^7$;

R$^5$ is C$_1$-C$_3$alkyl;

R$^6$ is N,N-diC$_1$-C$_3$alkylamino; and

R$^7$ is selected from fluorine, chlorine, C$_1$-C$_3$alkyl, C$_1$-C$_3$alkoxy, C$_1$-C$_3$fluoroalkoxy, C$_1$-C$_3$fluoroalkyl, C$_3$-C$_6$cycloalkyl and N,N-diC$_1$-C$_3$alkylamino.

In one embodiment of this aspect, Y is CH or C; X is O; and $R^4$ is hydrogen.

In one embodiment of this aspect, $R^1$ and $R^2$ are hydrogen;

$R^3$ is methyl;

X is selected from $CH_2$, O, $NCOR^5$, $NCOR^9$, $NCOCH_2R^9$, and a bond;

Y is N;

$R^4$ is hydrogen, phenyl or trifluoromethyl;

$R^5$ is methyl;

$R^7$ is methoxy;

$R^9$ is selected from pyridyl, phenyl; and $R^8$ is fluorine.

In one embodiment of this aspect, $R^1$ and $R^2$ are hydrogen;

$R^3$ is methyl;

X is selected from $CH_2$, O, $NCOR^5$, $NCOCH_2R^9$, and a bond;

Y is N;

$R^4$ is phenyl or trifluoromethyl, said phenyl being substituted with one or more $R^7$;

$R^5$ is methyl;

$R^7$ is methoxy or halogen, such as methoxy or chlorine;

$R^9$ is phenyl, said phenyl being optionally substituted by one or more $R^8$; and $R^8$ is halogen, such as fluorine.

In one embodiment of this aspect, $R^4$ is trifluoromethyl or phenyl, said phenyl being meta-substituted with methoxy or chlorine.

In one embodiment, compounds according to the invention are potent inhibitors of autophagy in HOS cells, as shown in Example 51.

In one embodiment of this aspect, $R^7$ is methoxy or chlorine; and $R^8$ is fluorine.

In one embodiment of this aspect, A represents

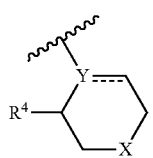

In one embodiment of this aspect, A represents

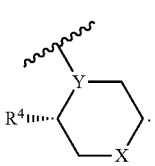

Compounds according to the invention having the configuration of the carbon on which $R^4$ is situated, according to this embodiment, are more potent inhibitors of Vps34 in vitro, as shown in appended example 50, see comparison of example compounds 3 versus 4 and 34 versus 35.

In one embodiment of this aspect, $R^1$ and $R^2$ are hydrogen;

$R^3$ is methyl;

X represents $NCOR^9$ or $NCOCH_2R^9$;

$R^4$ is trifluoromethyl or phenyl, said phenyl being optionally substituted with methoxy or chlorine;

$R^9$ is selected from $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and $R^8$ is selected from fluorine, chlorine, $C_1$-$C_3$haloalkyl and $C_1$-$C_3$alkyl.

In one embodiment of this aspect, $R^1$ and $R^2$ are hydrogen;

$R^3$ is methyl;

X represents $NCOR^9$ or $NCOCH_2R^9$;

$R^4$ is trifluoromethyl;

$R^9$ is selected from $C_1$-$C_3$alkyl, $C_1$-$C_3$alkoxy, $C_3$-$C_6$cycloalkyl, oxazolyl, tetrahydrofuryl, morpholinyl, pyridyl and phenyl, wherein said oxazolyl, said tetrahydrofuryl, said morpholinyl, said pyridyl and said phenyl are optionally substituted with one or two $R^8$; and $R^8$ is selected from fluorine, chlorine, $C_1$-$C_3$haloalkyl and $C_1$-$C_3$alkyl.

In one embodiment, a compound according to the invention admits several possible $R^9$ since the bioactive conformation of said compound is, when binding to vps34, such that $R^9$ is located in the solvent, rather than inside the binding pocket.

In one embodiment of this aspect,

X represents $CH_2$, SO, $SO_2$, $NR^5$, $NCOR^5$, $NCOR^9$, $NCOCH_2R^9$ or O;

$R^1$ and $R^3$ are independently selected from hydrogen and methyl;

$R^2$ is hydrogen;

$R^4$ is selected from

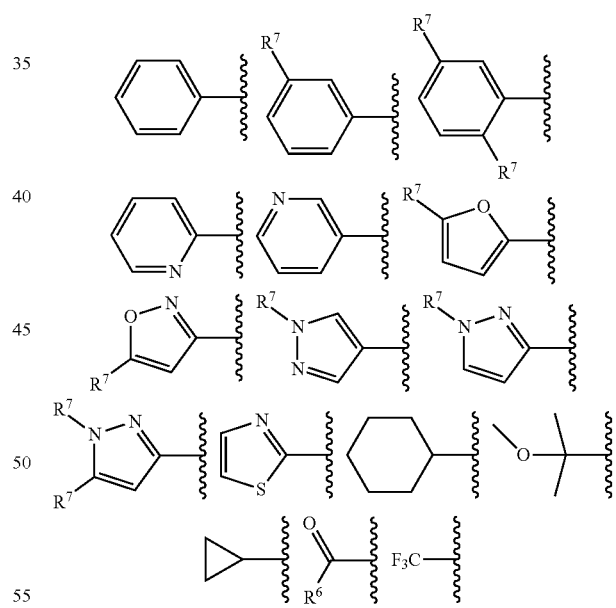

$R^5$ is $C_1$-$C_3$alkyl;

$R^7$ is selected from fluorine, chlorine, methyl, ethyl, methoxy, trifluoromethoxy, trifluoromethyl, cyclopropyl and N,N-dimethylamino;

$R^9$ is selected from tetrahydrofuryl, phenyl and pyridyl, each optionally substituted with one or two $R^8$; and $R^8$ is halogen.

In one embodiment of this aspect, $R^1$, $R^2$ and $R^3$ are independently selected from hydrogen and methyl; and A represents
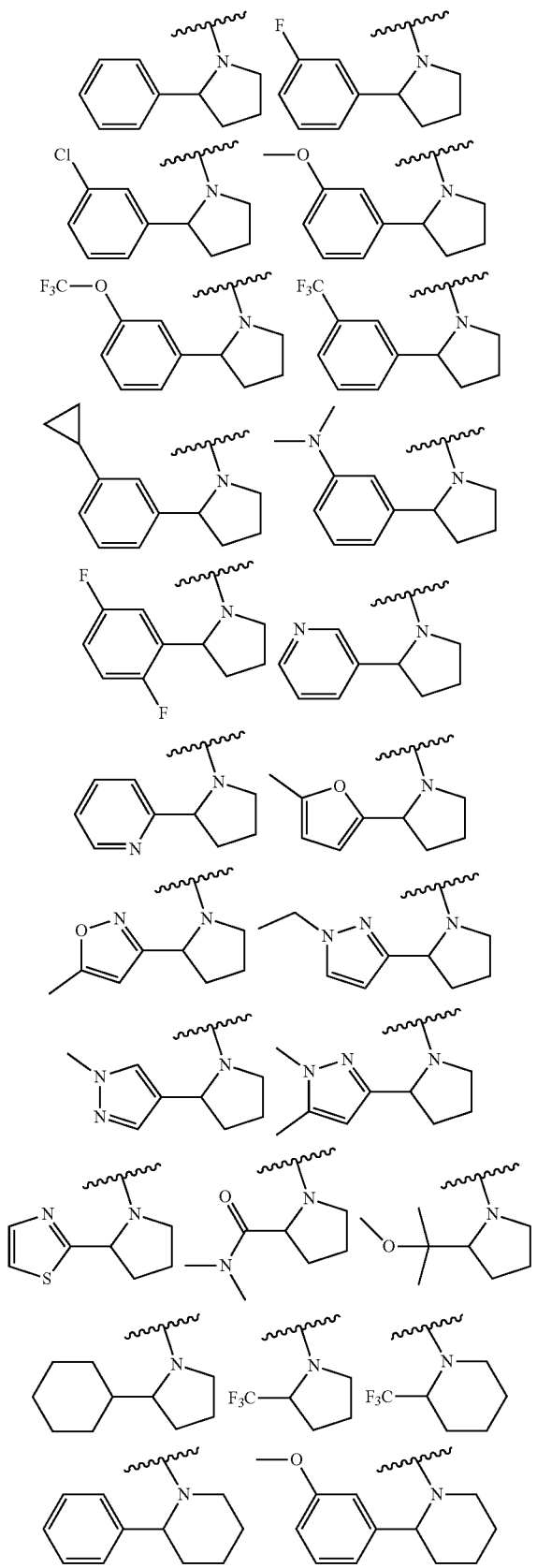
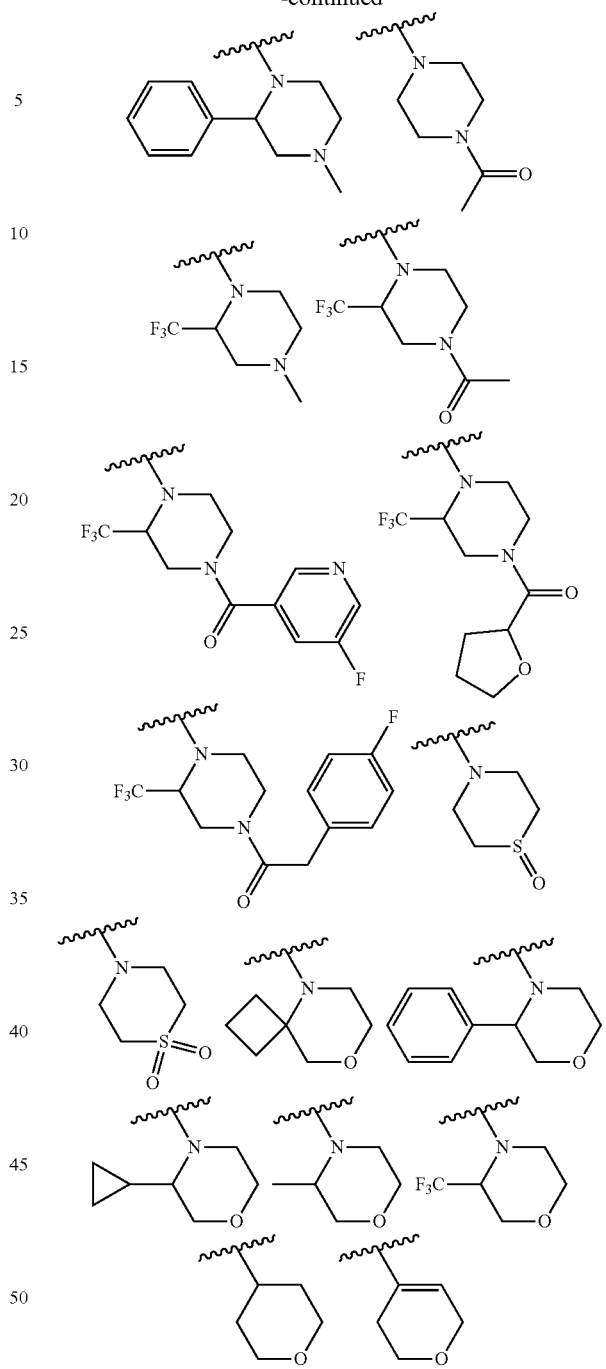
In one embodiment of this aspect, said compound is selected from:
4-morpholino-6-(2-phenylpyrrolidin-1-yl)-1H-pyridin-2-one;
1-methyl-4-morpholino-6-(2-phenylpyrrolidin-1-yl)pyridin-2-one;
4-morpholino-6-[(2S)-2-phenylpyrrolidin-1-yl]-1H-pyridin-2-one;
4-morpholino-6-[(2R)-2-phenylpyrrolidin-1-yl]-1H-pyridin-2-one;
6-(3,6-dihydro-2H-pyran-4-yl)-4-(3-methylmorpholin-4-yl)-1H-pyridin-2-one;

4-(3-methylmorpholin-4-yl)-6-tetrahydropyran-4-yl-1H-pyridin-2-one;
6-[2-(3-methoxyphenyl)pyrrolidin-1-yl]-4-(3-methylmorpholin-4-yl)-1H-pyridin-2-one;
4-(3-methylmorpholin-4-yl)-6-[2-(3-pyridyl)pyrrolidin-1-yl]-1H-pyridin-2-one;
4-(3-methylmorpholin-4-yl)-6-(2-phenylpyrrolidin-1-yl)-1H-pyridin-2-one;
N,N-dimethyl-1-[4-[(3R)-3-methylmorpholin-4-yl]-6-oxo-1H-pyridin-2-yl]pyrrolidine-2-carboxamide;
6-[2-(1-methoxy-1-methyl-ethyl)pyrrolidin-1-yl]-4-[(3R)-3-methylmorpholin-4-yl]-1H-pyridin-2-one;
6-(2-cyclohexylpyrrolidin-1-yl)-4-[(3R)-3-methylmorpholin-4-yl]-1H-pyridin-2-one;
6-[2-(3-fluorophenyl)pyrrolidin-1-yl]-4-[(3R)-3-methylmorpholin-4-yl]-1H-pyridin-2-one;
6-[2-(2,5-difluorophenyl)pyrrolidin-1-yl]-4-[(3R)-3-methylmorpholin-4-yl]-1H-pyridin-2-one;
4-[(3R)-3-methylmorpholin-4-yl]-6-[2-[3-(trifluoromethoxy)phenyl]pyrrolidin-1-yl]-1H-pyridin-2-one;
4-[(3R)-3-methylmorpholin-4-yl]-6-[2-[3-(trifluoromethyl)phenyl]pyrrolidin-1-yl]-1H-pyridin-2-one;
6-[2-(3-methoxyphenyl)pyrrolidin-1-yl]-4-[(3R)-3-methylmorpholin-4-yl]-1H-pyridin-2-one;
4-[(3R)-3-methylmorpholin-4-yl]-6-(2-phenylpyrrolidin-1-yl)-1H-pyridin-2-one;
4-[(3R)-3-methylmorpholin-4-yl]-6-[2-(1-methylpyrazol-4-yl)pyrrolidin-1-yl]-1H-pyridin-2-one;
6-[2-(1,5-dimethylpyrazol-3-yl)pyrrolidin-1-yl]-4-[(3R)-3-methylmorpholin-4-yl]-1H-pyridin-2-one;
6-[2-(1-ethylpyrazol-3-yl)pyrrolidin-1-yl]-4-[(3R)-3-methylmorpholin-4-yl]-1H-pyridin-2-one;
6-[2-(5-methyl-2-furyl)pyrrolidin-1-yl]-4-[(3R)-3-methylmorpholin-4-yl]-1H-pyridin-2-one;
6-[2-[3-(dimethylamino)phenyl]pyrrolidin-1-yl]-4-[(3R)-3-methylmorpholin-4-yl]-1H-pyridin-2-one;
4-[(3R)-3-methylmorpholin-4-yl]-6-(3-methylmorpholin-4-yl)-1H-pyridin-2-one;
4-[(3R)-3-methylmorpholin-4-yl]-6-[2-(trifluoromethyl)-1-piperidyl]-1H-pyridin-2-one;
4-[(3R)-3-methylmorpholin-4-yl]-6-(3-phenylmorpholin-4-yl)-1H-pyridin-2-one;
4-[(3R)-3-methylmorpholin-4-yl]-6-(1-oxo-1,4-thiazinan-4-yl)-1H-pyridin-2-one;
6-(1,1-dioxo-1,4-thiazinan-4-yl)-4-[(3R)-3-methylmorpholin-4-yl]-1H-pyridin-2-one;
6-(4-acetylpiperazin-1-yl)-4-[(3R)-3-methylmorpholin-4-yl]-1H-pyridin-2-one;
4-[(3R)-3-methylmorpholin-4-yl]-6-[(2R)-2-phenyl-1-piperidyl]-1H-pyridin-2-one;
4-[(3R)-3-methylmorpholin-4-yl]-6-(4-methyl-2-phenyl-piperazin-1-yl)-1H-pyridin-2-one;
4-[(3R)-3-methylmorpholin-4-yl]-6-[3-(trifluoromethyl)morpholin-4-yl]-1H-pyridin-2-one;
6-(3-cyclopropylmorpholin-4-yl)-4-[(3R)-3-methylmorpholin-4-yl]-1H-pyridin-2-one;
4-[(3R)-3-methylmorpholin-4-yl]-6-[(2S)-2-(trifluoromethyl)pyrrolidin-1-yl]-1H-pyridin-2-one;
4-[(3R)-3-methylmorpholin-4-yl]-6-[(2R)-2-(trifluoromethyl)pyrrolidin-1-yl]-1H-pyridin-2-one;
6-[2-(3-chlorophenyl)pyrrolidin-1-yl]-4-[(3R)-3-methylmorpholin-4-yl]-1H-pyridin-2-one;
6-[2-(3-cyclopropylphenyl)pyrrolidin-1-yl]-4-[(3R)-3-methylmorpholin-4-yl]-1H-pyridin-2-one;
4-[(3R)-3-methylmorpholin-4-yl]-6-[2-(2-pyridyl)pyrrolidin-1-yl]-1H-pyridin-2-one;
4-[(3R)-3-methylmorpholin-4-yl]-6-(2-thiazol-2-ylpyrrolidin-1-yl)-1H-pyridin-2-one;
6-[2-(5-methylisoxazol-3-yl)pyrrolidin-1-yl]-4-[(3R)-3-methylmorpholin-4-yl]-1H-pyridin-2-one;
1-methyl-4-[(3R)-3-methylmorpholin-4-yl]-6-[(2R)-2-(trifluoromethyl)-1-piperidyl]pyridin-2-one;
4-[(3R)-3-methylmorpholin-4-yl]-6-(8-oxa-5-azaspiro[3.5]nonan-5-yl)-1H-pyridin-2-one;
6-[2-(3-methoxyphenyl)-1-piperidyl]-4-[(3R)-3-methylmorpholin-4-yl]-1H-pyridin-2-one;
6-[4-acetyl-2-(trifluoromethyl)piperazin-1-yl]-4-[(3R)-3-methylmorpholin-4-yl]-1H-pyridin-2-one;
6-[4-(5-fluoropyridine-3-carbonyl)-2-(trifluoromethyl)piperazin-1-yl]-4-[(3R)-3-methylmorpholin-4-yl]-1H-pyridin-2-one;
6-[4-[2-(4-fluorophenyl)acetyl]-2-(trifluoromethyl)piperazin-1-yl]-4-[(3R)-3-methylmorpholin-4-yl]-1H-pyridin-2-one;
4-[(3R)-3-methylmorpholin-4-yl]-6-[4-(tetrahydrofuran-2-carbonyl)-2-(trifluoromethyl)piperazin-1-yl]-1H-pyridin-2-one;
4-[(3R)-3-methylmorpholin-4-yl]-6-[4-methyl-2-(trifluoromethyl)piperazin-1-yl]-1H-pyridin-2-one; and
pharmaceutically acceptable salts, tautomers and stereoisomers thereof.

According to one aspect of the invention, there is provided a compound of Formula (I)

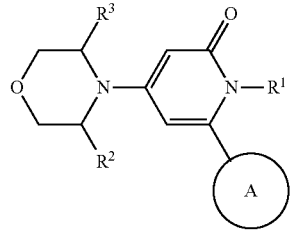

wherein
$R^1$, $R^2$ and $R^3$ are independently selected from hydrogen, $C_1$-$C_3$haloalkyl and $C_1$-$C_3$alkyl;
A represents

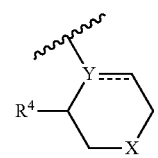

wherein
X represents $CH_2$, S, SO, $SO_2$, $NR^5$, $NCOR^5$, $NCOR^9$, $NCOCH_2R^9$, O, or a bond;
Y represents N, CH or C;
$R^4$ is selected from hydrogen, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_1$-$C_3$cyanoalkyl, $C_1$-$C_3$haloalkyl, aryl and heteroaryl, wherein said aryl and said heteroaryl are, mono- or bicyclic, and optionally substituted with one or more $R^7$;
$R^5$ is selected from hydrogen, $C_1$-$C_3$fluoroalkyl, $C_1$-$C_3$alkyl, $C_1$-$C_3$alkoxy$C_1$-$C_3$alkyl and $C_3$-$C_6$cycloalkyl;

$R^6$ is selected from $C_1$-$C_3$alkoxy, N—$C_1$-$C_3$alkylamino, N,N-di$C_1$-$C_3$alkylamino, 1-pyrrolidinyl, 1-piperidinyl and 1-azetidinyl;

$R^7$ is selected from $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N,N-di$C_1$-$C_3$alkylamino, $C_1$-$C_3$haloalkoxy and $C_1$-$C_3$alkoxy;

$R^9$ is selected from $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$;

$R^8$ is selected from halogen, $C_1$-$C_3$haloalkyl and $C_1$-$C_3$alkyl; and pharmaceutically acceptable salts, stereoisomers and tautomers thereof.

In the A ring, "- -" denotes either a single or double bond. When Y in said ring is C (quaternary sp²-hybridized carbon), the bond is a double bond. When Y in said ring is N or CH, the bond is a single bond.

In one embodiment of this aspect, $R^1$ and $R^2$ are hydrogen;

$R^3$ is methyl;

X represents NCOR$^9$ or NCOCH$_2$R$^9$;

$R^4$ is trifluoromethyl;

$R^9$ is selected from $C_1$-$C_3$alkyl, $C_1$-$C_3$alkoxy, $C_3$-$C_6$cycloalkyl, oxazolyl, tetrahydrofuryl, morpholinyl, pyridyl and phenyl, wherein said oxazolyl, said tetrahydrofuryl, said morpholinyl, said pyridyl and said phenyl are optionally substituted with one or two $R^8$; and $R^8$ is selected from fluorine, chlorine, $C_1$-$C_3$haloalkyl and $C_1$-$C_3$alkyl.

In one embodiment, a compound according to the invention admits several possible $R^9$ since the bioactive conformation of said compound is, when binding to vps34, such that $R^9$ is located in the solvent, rather than inside the binding pocket.

In one embodiment of this aspect, $R^9$ is selected from methyl, methoxy, cyclobutyl, 2-methyl-1,3-oxazol-4-yl, 2-tetrahydrofuryl, 4-morpholinyl, 3-pyridyl, 3-fluoro-5-pyridyl.

In one embodiment of this aspect, Y is N.

In one embodiment of this aspect, $R^1$ and $R^3$ are independently selected from hydrogen and methyl.

In one embodiment of this aspect, $R^2$ is hydrogen.

In one embodiment of this aspect, $R^1$ is hydrogen.

In one embodiment of this aspect, $R^1$ is methyl.

In one embodiment of this aspect, $R^3$ is methyl.

In one embodiment of this aspect, $R^3$ is hydrogen.

In one embodiment of this aspect,

X represents CH$_2$, SO, SO$_2$, NR$^5$, NCOR$^5$, O, or a bond;

$R^4$ is selected from hydrogen, COR$^6$, $C_1$-$C_3$alkyl, methoxy$C_1$-$C_3$alkyl, $C_3$-$C_6$cycloalkyl, $C_1$-$C_3$fluoroalkyl, phenyl and a monocyclic heteroaryl, wherein said phenyl and said monocyclic heteroaryl are optionally substituted with one or two $R^7$;

$R^5$ is $C_1$-$C_3$alkyl;

$R^6$ is N,N-di$C_1$-$C_3$alkylamino; and $R^7$ is selected from fluorine, chlorine, $C_1$-$C_3$alkoxy, $C_1$-$C_3$fluoroalkoxy, $C_1$-$C_3$fluoroalkyl, $C_3$-$C_6$cycloalkyl, N,N-di$C_1$-$C_3$alkylamino.

In one embodiment of this aspect, said monocyclic heteroaryl in $R^4$ is selected from pyridyl, furyl, isoxasolyl, pyrazolyl and thiazolyl.

In one embodiment of this aspect, $R^4$ is selected from

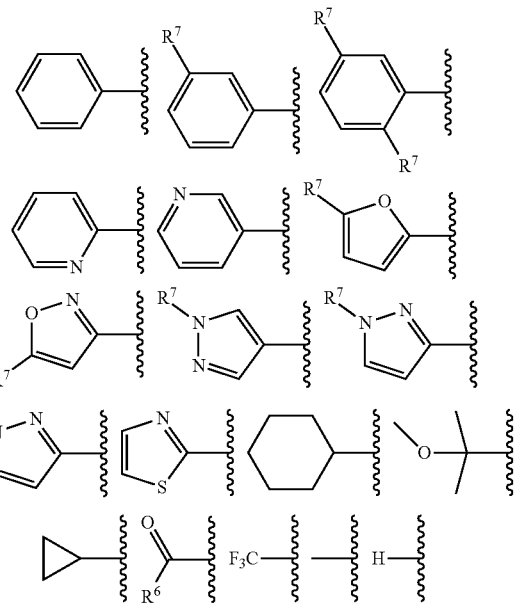

wherein $R^6$ is dimethylamino; and $R^7$ is selected from fluorine, chlorine, trifluoromethyl, trifluoromethoxy, methoxy, methyl, ethyl, cyclopropyl and dimethylamino.

In one embodiment of this aspect, X represents a bond.

In one embodiment of this aspect, A represents:

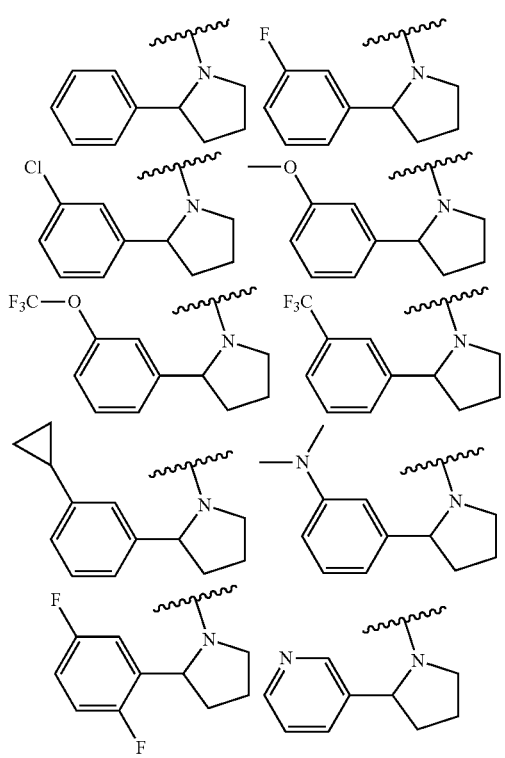

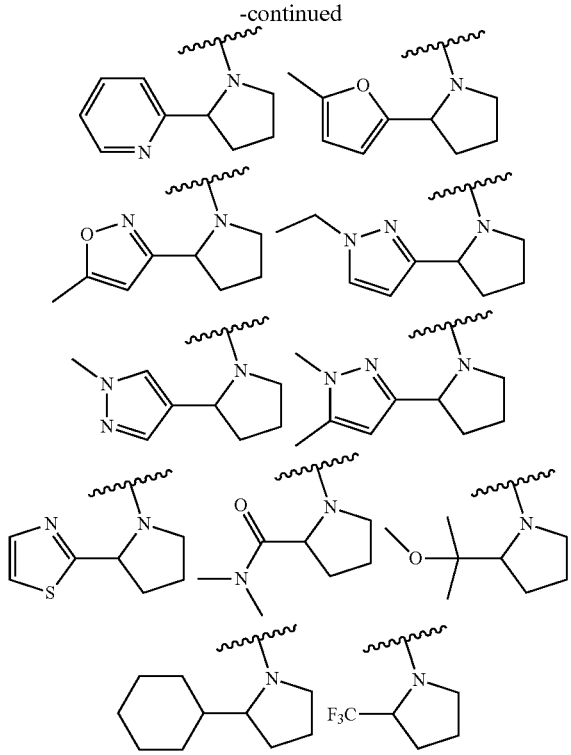

In one embodiment of this aspect, X represents CH₂, SO, SO₂, NR⁵, NCOR⁵ or O; and
R⁵ is C₁-C₃alkyl.
In one embodiment of this aspect, A represents:

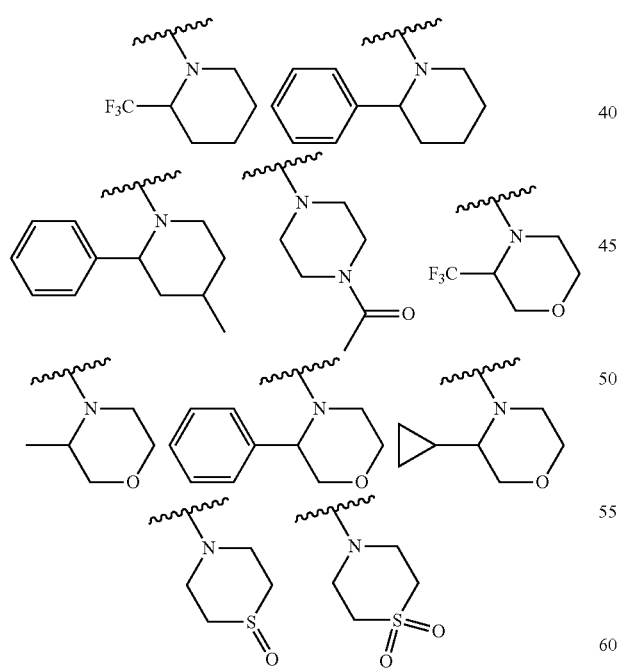

In one embodiment of this aspect, Y is CH or C; X is O; and R⁴ is hydrogen.
In one embodiment of this aspect
R¹ and R² are hydrogen;
R³ is methyl;
X is selected from CH₂, O and a bond;
Y is N;
R⁴ is phenyl or trifluoromethyl; and
R⁷ is selected from methoxy, trifluoromethyl, chlorine and cyclopropyl.

In one embodiment of this aspect,
R¹ and R³ are independently selected from hydrogen, and methyl;
R² is hydrogen; and
A represents

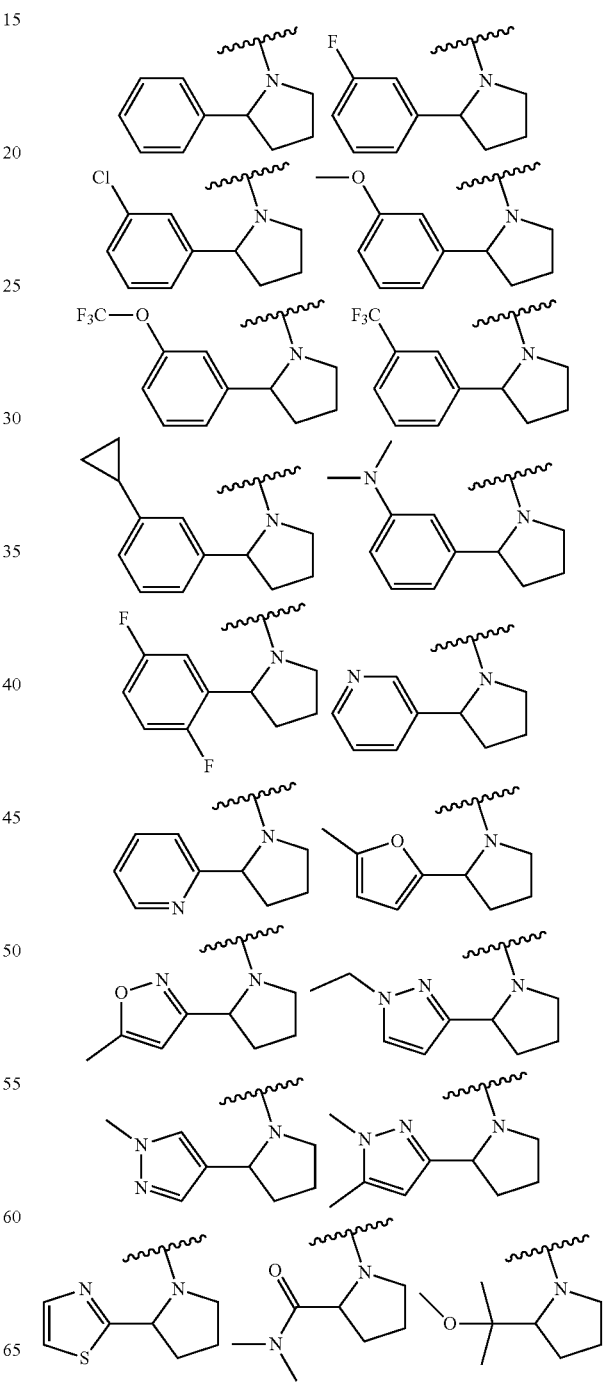

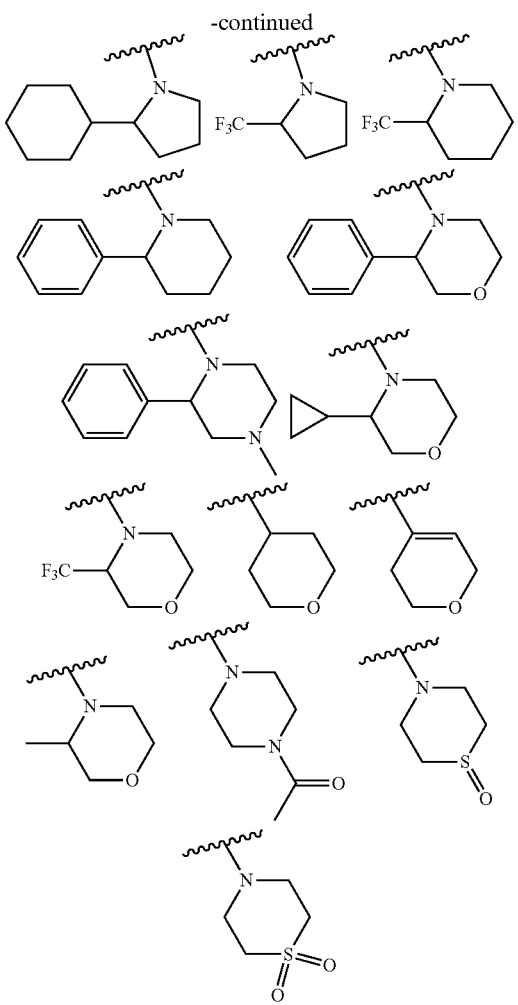

In one embodiment of this aspect, there is provided a compound selected from:
4-morpholino-6-(2-phenylpyrrolidin-1-yl)-1H-pyridin-2-one;
1-methyl-4-morpholino-6-(2-phenylpyrrolidin-1-yl)pyridin-2-one;
4-morpholino-6-[(2S)-2-phenylpyrrolidin-1-yl]-1H-pyridin-2-one;
4-morpholino-6-[(2R)-2-phenylpyrrolidin-1-yl]-1H-pyridin-2-one;
6-(3,6-dihydro-2H-pyran-4-yl)-4-(3-methylmorpholin-4-yl)-1H-pyridin-2-one;
4-(3-methylmorpholin-4-yl)-6-tetrahydropyran-4-yl-1H-pyridin-2-one;
6-[2-(3-methoxyphenyl)pyrrolidin-1-yl]-4-(3-methylmorpholin-4-yl)-1H-pyridin-2-one;
4-(3-methylmorpholin-4-yl)-6-[2-(3-pyridyl)pyrrolidin-1-yl]-1H-pyridin-2-one;
4-(3-methylmorpholin-4-yl)-6-(2-phenylpyrrolidin-1-yl)-1H-pyridin-2-one;
N,N-dimethyl-1-[4-[(3R)-3-methylmorpholin-4-yl]-6-oxo-1H-pyridin-2-yl]pyrrolidine-2-carboxamide;
6-[2-(1-methoxy-1-methyl-ethyl)pyrrolidin-1-yl]-4-[(3R)-3-methylmorpholin-4-yl]-1H-pyridin-2-one;
6-(2-cyclohexylpyrrolidin-1-yl)-4-[(3R)-3-methylmorpholin-4-yl]-1H-pyridin-2-one;
6-[2-(3-fluorophenyl)pyrrolidin-1-yl]-4-[(3R)-3-methylmorpholin-4-yl]-1H-pyridin-2-one;
6-[2-(2,5-difluorophenyl)pyrrolidin-1-yl]-4-[(3R)-3-methylmorpholin-4-yl]-1H-pyridin-2-one;
4-[(3R)-3-methylmorpholin-4-yl]-6-[2-[3-(trifluoromethoxy)phenyl]pyrrolidin-1-yl]-1H-pyridin-2-one;
4-[(3R)-3-methylmorpholin-4-yl]-6-[2-[3-(trifluoromethyl)phenyl]pyrrolidin-1-yl]-1H-pyridin-2-one;
6-[2-(3-methoxyphenyl)pyrrolidin-1-yl]-4-[(3R)-3-methylmorpholin-4-yl]-1H-pyridin-2-one;
4-[(3R)-3-methylmorpholin-4-yl]-6-(2-phenylpyrrolidin-1-yl)-1H-pyridin-2-one;
4-[(3R)-3-methylmorpholin-4-yl]-6-[2-(1-methylpyrazol-4-yl)pyrrolidin-1-yl]-1H-pyridin-2-one;
6-[2-(1,5-dimethylpyrazol-3-yl)pyrrolidin-1-yl]-4-[(3R)-3-methylmorpholin-4-yl]-1H-pyridin-2-one;
6-[2-(1-ethylpyrazol-3-yl)pyrrolidin-1-yl]-4-[(3R)-3-methylmorpholin-4-yl]-1H-pyridin-2-one;
6-[2-(5-methyl-2-furyl)pyrrolidin-1-yl]-4-[(3R)-3-methylmorpholin-4-yl]-1H-pyridin-2-one;
6-[2-[3-(dimethylamino)phenyl]pyrrolidin-1-yl]-4-[(3R)-3-methylmorpholin-4-yl]-1H-pyridin-2-one;
4-[(3R)-3-methylmorpholin-4-yl]-6-(3-methylmorpholin-4-yl)-1H-pyridin-2-one;
4-[(3R)-3-methylmorpholin-4-yl]-6-[2-(trifluoromethyl)-1-piperidyl]-1H-pyridin-2-one;
4-[(3R)-3-methylmorpholin-4-yl]-6-(3-phenylmorpholin-4-yl)-1H-pyridin-2-one;
4-[(3R)-3-methylmorpholin-4-yl]-6-(1-oxo-1,4-thiazinan-4-yl)-1H-pyridin-2-one;
6-(1,1-dioxo-1,4-thiazinan-4-yl)-4-[(3R)-3-methylmorpholin-4-yl]-1H-pyridin-2-one;
6-(4-acetylpiperazin-1-yl)-4-[(3R)-3-methylmorpholin-4-yl]-1H-pyridin-2-one;
4-[(3R)-3-methylmorpholin-4-yl]-6-[(2R)-2-phenyl-1-piperidyl]-1H-pyridin-2-one;
4-[(3R)-3-methylmorpholin-4-yl]-6-(4-methyl-2-phenylpiperazin-1-yl)-1H-pyridin-2-one;
4-[(3R)-3-methylmorpholin-4-yl]-6-[3-(trifluoromethyl)morpholin-4-yl]-1H-pyridin-2-one;
6-(3-cyclopropylmorpholin-4-yl)-4-[(3R)-3-methylmorpholin-4-yl]-1H-pyridin-2-one;
4-[(3R)-3-methylmorpholin-4-yl]-6-[(2S)-2-(trifluoromethyl)pyrrolidin-1-yl]-1H-pyridin-2-one;
4-[(3R)-3-methylmorpholin-4-yl]-6-[(2R)-2-(trifluoromethyl)pyrrolidin-1-yl]-1H-pyridin-2-one;
6-[2-(3-chlorophenyl)pyrrolidin-1-yl]-4-[(3R)-3-methylmorpholin-4-yl]-1H-pyridin-2-one;
6-[2-(3-cyclopropylphenyl)pyrrolidin-1-yl]-4-[(3R)-3-methylmorpholin-4-yl]-1H-pyridin-2-one;
4-[(3R)-3-methylmorpholin-4-yl]-6-[2-(2-pyridyl)pyrrolidin-1-yl]-1H-pyridin-2-one;
4-[(3R)-3-methylmorpholin-4-yl]-6-(2-thiazol-2-ylpyrrolidin-1-yl)-1H-pyridin-2-one;
6-[2-(5-methylisoxazol-3-yl)pyrrolidin-1-yl]-4-[(3R)-3-methylmorpholin-4-yl]-1H-pyridin-2-one;
1-methyl-4-[(3R)-3-methylmorpholin-4-yl]-6-[(2R)-2-(trifluoromethyl)-1-piperidyl]pyridin-2-one; and
pharmaceutically acceptable salts, tautomers and stereoisomers thereof.

In one aspect of the invention, there is provided a compound according to the present invention, for use in the treatment or prophylaxis of a disease.

In one aspect of the invention, there is provided a compound according to the present invention, for use in treating cancer. Typically, said cancer is selected from breast cancer, such as triple negative breast cancer, pancreas cancer, leukemia, melanoma and lung cancer.

In one aspect of the invention, there is provided a compound according to the present invention, for use in treating diabetes. Typically, said diabetes is type II diabetes.

In one aspect of the invention, there is provided a compound according to the present invention, for use in treating a disease selected from inflammatory diseases, neurodegenerative disorders, cardiovascular disorders and viral infections.

In one aspect of the invention, there is provided use of a compound according to the present invention, in the preparation of a medicament for treating cancer. Typically said cancer is selected from breast cancer, such as triple negative breast cancer, pancreas cancer, leukemia, melanoma and lung cancer.

In one aspect of the invention, there is provided use of a compound according to the present invention, in the preparation of a medicament for treating diabetes. Typically, said diabetes is type II diabetes.

In one aspect of the invention, there is provided use of a compound according to the present invention, in the preparation of a medicament for treating a disease selected from inflammatory diseases, neurodegenerative disorders, cardiovascular disorders and viral infections.

In one aspect of the invention, there is provided a method of treating cancer, comprising administering a therapeutically effective amount of a compound according to the present invention, to a patient in need thereof. Typically, said cancer is selected from breast cancer, such as triple negative breast cancer, pancreas cancer, leukemia, melanoma and lung cancer.

In one aspect of the invention, there is provided a compound according to the present invention, for use in treating cancer, wherein said cancer treatment further comprises radiation therapy.

In one aspect of the invention, there is provided a method of treating cancer, comprising administering a therapeutically effective amount of a compound according to the present invention, to a patient in need thereof, in conjunction with radiation therapy.

The compounds of the present invention may also be employed in cancer treatment in conjunction with radiation therapy and/or surgical intervention. Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

In one aspect of the invention, there is provided a method of treating diabetes, comprising administering a therapeutically effective amount of a compound according to the present invention, to a patient in need thereof. Typically, said diabetes is type II diabetes.

In one aspect of the invention, there is provided a method of treating a disease selected from inflammatory disease, inflammatory diseases, neurodegenerative disorders, and viral infections, comprising administering a therapeutically effective amount of a compound according to the present invention, to a patient in need thereof.

In one aspect of the invention, there is provided a pharmaceutical composition comprising a compound according to the present invention, and a pharmaceutically acceptable diluent, carrier and/or excipient.

In one aspect of the invention, there is provided a pharmaceutical composition, comprising a therapeutically effective amount of a compound according to claim 1 and another anticancer agent selected from alkylating agents, antimetabolites, anticancer camptothecin derivatives, plan-derived anticancer agents, antibiotics, enzymes, platinum coordination complexes, tyrosine kinase inhibitors, hormones, hormone antagonists, monoclonal antibodies, interferons, and biological response modifiers.

As used herein, the term "$C_1$-$C_6$alkyl" means both linear and branched chain saturated hydrocarbon groups with 1 to 6 carbon atoms. Examples of $C_1$-$C_6$alkyl groups include methyl, ethyl, n-propyl, isopropyl, n-butyl, iso-butyl, sec-butyl, t-butyl, n-pentyl, 4-methyl-butyl, n-hexyl, 2-ethyl-butyl groups. Among unbranched $C_1$-$C_6$alkyl groups, typical ones are methyl, ethyl, n-propyl, n-butyl, n-pentyl and n-hexyl groups. Among branched alkyl groups, there may be mentioned iso-propyl, iso-butyl, sec-butyl, t-butyl, 4-methyl-butyl and 2-ethyl-butyl groups.

As used herein, the term "$C_1$-$C_3$alkyl" means both linear and branched chain saturated hydrocarbon groups with 1 to 3 carbon atoms. Examples of $C_1$-$C_3$alkyl groups include methyl, ethyl, n-propyl and isopropyl groups.

As used herein, the term "$C_1$-$C_6$alkoxy" means the group O-alkyl, where "$C_1$-$C_6$alkyl" is used as described above. Examples of $C_1$-$C_6$alkoxy groups include, but are not limited to, methoxy, ethoxy, isopropoxy, n-propoxy, n-butoxy, n-hexoxy, 3-methyl-butoxy groups.

As used herein, the term "$C_1$-$C_3$alkoxy" means the group O-alkyl, where "$C_1$-$C_3$alkyl" is used as described above. Examples of $C_1$-$C_3$alkoxy groups include, but are not limited to, methoxy, ethoxy, isopropoxy and n-propoxy.

As used herein, the term "$C_1$-$C_6$haloalkyl" means both linear and branched chain saturated hydrocarbon groups, with 1 to 6 carbon atoms and with 1 to all hydrogens substituted by a halogen of different or same type. Examples of $C_1$-$C_6$haloalkyl groups include methyl substituted with 1 to 3 halogen atoms, ethyl substituted with 1 to 5 halogen atoms, n-propyl or iso-propyl substituted with 1 to 7 halogen atoms, n-butyl or iso-butyl substituted with 1 to 9 halogen atoms, and sec-butyl or t-butyl groups substituted with 1 to 9 halogen atoms.

As used herein, the term "$C_1$-$C_3$haloalkyl" means both linear and branched chain saturated hydrocarbon groups, with 1 to 3 carbon atoms and with 1 to all hydrogens substituted by a halogen of different or same type. Examples of $C_1$-$C_3$haloalkyl groups include methyl substituted with 1 to 3 halogen atoms, ethyl substituted with 1 to 5 halogen atoms, and n-propyl or iso-propyl substituted with 1 to 7 halogen atoms.

As used herein, the term "$C_1$-$C_3$haloalkoxy" means both linear and branched chain saturated alkoxy groups, with 1 to 3 carbon atoms and with 1 to all hydrogen atoms substituted by a halogen atom of different or same type. Examples of $C_1$-$C_3$haloalkoxy groups include methoxy substituted with 1 to 3 halogen atoms, ethoxy substituted with 1 to 5 halogen atoms, and n-propoxy or iso-propoxy substituted with 1 to 7 halogen atoms.

As used herein, the term "$C_1$-$C_3$fluorooalkyl" means both linear and branched chain saturated hydrocarbon groups, with 1 to 3 carbon atoms and with 1 to all hydrogen atoms substituted by a fluorine atom. Examples of $C_1$-$C_3$fluoroalkyl groups include methyl substituted with 1 to 3 fluorine atoms, ethyl substituted with 1 to 5 fluorine atoms, and n-propyl or iso-propyl substituted with 1 to 7 fluorine atoms.

As used herein, the term "$C_1$-$C_3$fluorooalkoxy" means both linear and branched chain saturated alkoxy groups, with 1 to 3 carbon atoms and with 1 to all hydrogen atoms substituted by a fluorine atom. Examples of $C_1$-$C_3$fluoroalkoxy groups include methoxy substituted with 1 to 3 fluorine atoms, ethoxy substituted with 1 to 5 fluorine atoms, and n-propoxy or iso-propoxy substituted with 1 to 7 fluorine atoms.

As used herein, the term "$C_3$-$C_6$cycloalkyl" means a cyclic saturated hydrocarbon group, with 3 to 6 carbon atoms. Examples of $C_3$-$C_6$cycloalkyl groups include cyclopropyl, cyclobutyl, cyclopentyl and cyclohexyl.

As used herein, the term "$C_1$-$C_3$alkoxy$C_1$-$C_3$alkyl" means both a both linear and branched chain saturated hydrocarbon group, with 1 to 3 carbon atoms, substituted with an alkoxy group with 1 to 3 carbon atoms. Examples of $C_1$-$C_3$alkoxy$C_1$-$C_3$alkyl groups are drawn below.

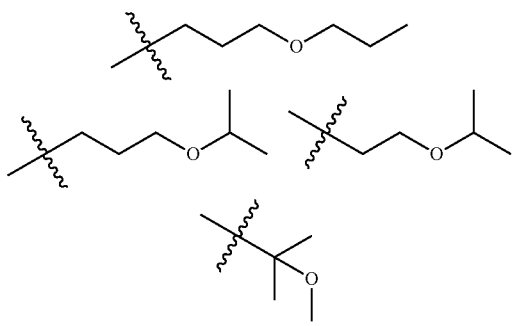

As used herein, the term "$C_1$-$C_3$cyanoalkyl" means both a linear and branched chain cyano (CN) derivative, with one to three carbon atoms including the carbon atom that is part of the cyano group. Examples of $C_1$-$C_3$cyanoalkyl groups are drawn below.

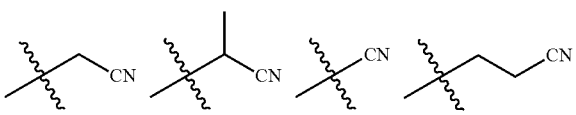

As used herein, the term "halogen" means fluorine, chlorine, bromine or iodine.

As used herein, the term "aryl" means a monocyclic or bicyclic aromatic carbocyclic group. Examples of aryl groups include phenyl and naphthyl. A naphthyl group may be attached through the 1 or the 2 position. In a bicyclic aryl, one of the rings may be partially saturated. Examples of such groups include indanyl and tetrahydronaphthyl.

As used herein, the term "monocyclic aryl" means a monocyclic aromatic carbocyclic group. Examples of monocyclic aryl groups include phenyl.

As used herein, the term "heteroaryl" means a monocyclic or bicyclic aromatic group of carbon atoms wherein from one to three of the carbon atoms is/are replaced by one or more heteroatoms independently selected from nitrogen, oxygen or sulfur. In a bicyclic aryl, one of the rings may be partially saturated. Examples of such groups include indolinyl, dihydrobenzofuran and 1,3-benzodioxolyl.

As used herein, the term "monocyclic heteroaryl" means a monocyclic aromatic group of carbon atoms wherein from one to three of the carbon atoms is/are replaced by one or more heteroatoms independently selected from nitrogen, oxygen or sulfur.

Examples of monocyclic heteroaryl groups include, but are not limited to, furyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl, and pyrimidinyl.

Examples of bicyclic heteroaryl groups include, but are not limited to, quinoxalinyl, quinazolinyl, pyridopyrazinyl, benzoxazolyl, benzothiophenyl, benzimidazolyl, naphthyridinyl, quinolinyl, benzofuryl, indolyl, indazolyl, benzothiazolyl, pyridopyrimidinyl, and isoquinolinyl.

As used herein, the term "heterocyclyl" means a cyclic group of carbon atoms wherein from one to three of the carbon atoms is/are replaced by one or more heteroatoms independently selected from nitrogen, oxygen and sulfur. Examples of heterocyclyl groups include, but are not limited to, tetrahydrofuryl, tetrahydropyranyl, pyrrolidinyl, piperidinyl, piperazinyl, morpholinyl and dioxanyl.

Depending on the substituents present in compounds of the formula (I), the compounds may form salts which are within the scope of the present invention. Salts of compounds of formula (I), which are suitable for use in medicine are those wherein a counterion is pharmaceutically acceptable.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)alkyl or aryl sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucamine, morpholine, thiomorpholine, piperidine, pyrrolidine, a mono, di- or tri lower alkylamine, for example ethyl, tertbutyl, diethyl, diisopropyl, triethyl, tributyl or dimethylpropylamine, or a mono-, di- or trihydroxy lower alkylamine, for example mono-, di- or triethanolamine. Corresponding internal salts may furthermore be formed.

The compounds of the invention may be used in the prophylaxis and/or treatment as such, or in a form of a pharmaceutical composition. While it is possible for the active ingredient to be administered alone, it is also possible for it to be present in a pharmaceutical composition. Accordingly, the invention provides a pharmaceutical composition comprising a compound of formula (I), and a pharmaceutically acceptable diluent, excipient and/or carrier. Pharmaceutical compositions of the invention may take the form of a pharmaceutical composition as described below.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such compositions may be high molecular weight excipients such as celluloses (avicel) or polyethylene glycols (PEG). Such compositions can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

Compositions of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Typical unit dosage compositions are those containing an effective dose, as hereinbefore recited, or an appropriate fraction thereof, of the active ingredient.

It should be understood that in addition to the ingredients particularly mentioned above, the compositions of this invention may include other agents conventional in the art having regard to the type of composition in question, for example those suitable for oral administration may include flavoring agents.

The compositions may be presented in unit dosage form and may be prepared by any of the methods well known in the art of pharmacy. Methods may include the step of bringing the active ingredient into association with the carrier which constitutes one or more accessory ingredients. Compositions may be prepared by uniformly and intimately bringing into association the active ingredient with liquid carriers or finely divided solid carriers or both and then, if necessary, shaping the product into the desired composition.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), phosphatidylserine, phosphatidylinositol, diphosphatidylglycerol (cardiolipin) or phosphatidylcholine (lecithin).

Compositions for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as polyethylene glycol, ethanol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Compositions for rectal administration may be presented as a suppository with the usual carriers such as cocoa butter, synthetic glyceride esters or polyethylene glycol.

Such carriers are typically solid at ordinary temperatures, but liquefy and/or dissolve in the rectal cavity to release the drug.

Compositions for topical administration in the mouth, for example buccally or sublingually, include lozenges comprising the active ingredient in a flavored basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Compounds of formula (I) may be administered as the sole pharmaceutical agent or in combination with one or more additional therapeutic agents where the combination causes no unacceptable adverse effects. This pharmaceutical composition includes administration of a single pharmaceutical dosage composition which contains a compound of formula (I) and one or more additional therapeutic agents, as well as administration of the compound of formula (I) and each additional therapeutic agent in its own separate pharmaceutical dosage composition. For example, a compound of formula (I) and a therapeutic agent may be administered to the patient together in a single oral dosage composition such as a capsule or tablet, or each agent may be administered in compositions with separate dosage.

Where separate dosage compositions are used, the compound of formula (I) and one or more additional therapeutic agents may be administered at essentially the same time (e.g., concurrently) or at separately staggered times (e.g., sequentially).

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions may be provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

EXAMPLES

Below follows a number of non-limiting examples of the invention.

The following table lists the abbreviations used in this section.

| Abbreviations | Meaning |
| --- | --- |
| Amphos | (4-(N,N-dimethylamino)phenyl)di-tert-butyl phosphine |
| anh. | anhydrous |
| aq. | aqueous |
| BuLi | butyl lithium |
| DCM | dichloromethane |
| DIPEA | N,N-Diisopropylethylamine |
| DMAc | N,N-dimethyl acetamide |
| DMF | N,N-dimethyl formamide |
| DMSO | dimethyl sulfoxide |
| DTT | Dithiothreitol |
| EtOAc | ethyl acetate |
| EtOH | ethanol |
| h | hour(s) |
| HPLC | high pressure (or performance) liquid chromatography |
| KOtBu | potassium tert-butoxide |
| LCMS | liquid chromatography mass spectrometry |
| LiOtBu | Lithium tert-butoxide |
| MeCN | acetonitrile |
| 2-MeTHF | 2-methyl tetrahydrofuran |
| MeOH | methanol |
| min. | minute(s) |
| NMR | nuclear magnetic resonance |
| PEPPSI™-iPr | [1,3-bis(2,6-Diisopropylphenyl)imidazol-2-ylidene](3-chloropyridyl)palladium(II) dichloride |
| $Pd_2(dba)_3$ | tris(dibenzylideneacetone)dipalladium(0) |
| $Pd(OAc)_2$ | palladium(II) acetate |
| quant. | quantitative |
| rt | room temperature |
| sat. | saturated |
| TFA | trifluoroacetic acid |
| THF | tetrahydrofuran |
| XantPhos | 4,5-bis(diphenylphosphino)-9,9-dimethylxanthene |
| XPhos | 2-dicyclohexylphosphino-2',4',6'-triisopropylbiphenyl |

Preparation of Compounds

Scheme 1 and 2 described below illustrate general synthetic routes to compounds of formula (I) of the invention but are not intended to be limiting. The compounds in the present invention may be prepared as a free base or a pharmaceutically acceptable salt thereof. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 4$^{th}$ Edition, Wiley-Interscience, New York, 2006. It is to be understood that microwaves can alternatively be used for the heating of reaction mixtures.

A, $R^1$, $R^2$, $R^3$, $R^4$, $R^5$, $R^6$, $R^7$, $R^8$ and $R^9$ are, unless specified otherwise, as defined in formula (I).

(i) Formation of the Corresponding Compound of Formula (III)

A compound of formula (III) may be obtained (Scheme 1) by starting from, for example, a compound of formula (II), wherein LG represents a leaving group such as halogen (such as chlorine, bromine or iodine), or an alkyl-, aryl- or haloalkyl-sulfonate (such as triflate), and reacting said compound (II) with an appropriate coupling partner A*, representing either an appropriate cyclic amine as free base or a salt (such as HCl or TFA or acetic acid), or an appropriate boronic acid or boronic acid derivative, under the influence of a transition metal catalyst as described in for example *Metal-Catalyzed Cross-Coupling Reactions, 2nd, Completely Revised and Enlarged Edition* by A. de Meijere and F. Diederich, Wiley VCH, 2004

Scheme 1

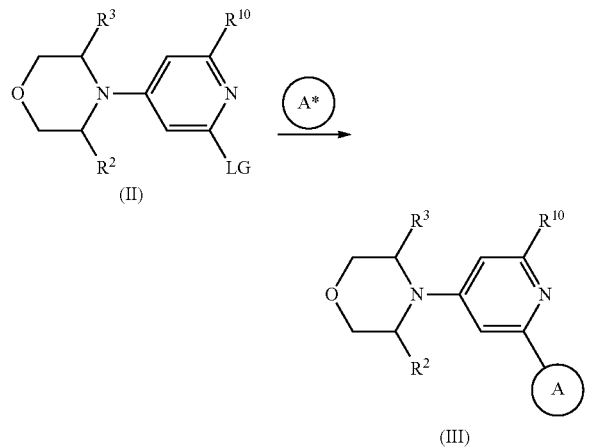

The reaction may be carried out by coupling of a compound of formula (II), with an appropriate coupling partner A*. The reaction may be carried out using a suitable metal catalyst such as palladium catalyst, such as di-tert-butylphosphinoferrocene palladium (II) dichloride, tetrakis(triphenylphosphine)palladium (0), palladium diphenylphosphinoferrocene dichloride, palladium(II) acetate or bis(dibenzylideneacetone) palladium (0). Optionally a suitable ligand such as triphenylphosphine, tri-tert-butylphosphine or 2-(dicyclohexylphosphino)biphenyl or 2-dicyclohexylphosphino-2',4',6'-triisopropylbiphenyl is employed. A suitable base, such as an alkyl amine, such as triethyl amine, or an alkali metal or alkaline earth metal carbonate or hydroxide or phosphate such as potassium carbonate, sodium carbonate, cesium carbonate, or sodium hydroxide, or potassium phosphate, may be used in the reaction. Said reaction may be performed at a temperature range between +20° C. and +160° C., in a suitable solvent, such as toluene, tetrahydrofuran, 2-methyl-tetrahydrofuran, dioxane, dimethoxyethane, acetonitrile, water, ethanol, N,N-dimethylacetamide or N,N-dimethylformamide, or mixtures thereof. If enantiomerically pure or enriched compound (II) is used in this reaction, an enantiomerically pure or enantiomerically enriched compound (III) is obtained.

(ii) Formation of a Corresponding Compound of Formula (I)

Scheme 2

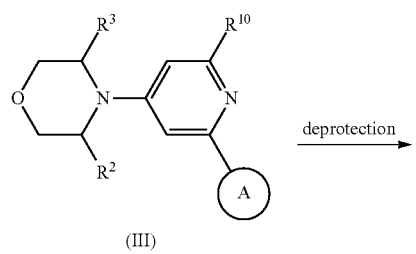

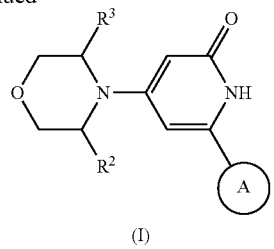

A compound of formula (I) may be obtained (Scheme 2) by starting from, for example, a compound of formula (III), wherein $R^{10}$ may be F, $OCH_3$, $OC(CH_3)_3$, or $OSiR'R''R'''$ (wherein R', R" and R''' are independently aryl (such as phenyl) or alkyl (such as methyl or tert-butyl)). If $R^{10}$ is F, the conversion into (I) may be carried out by for instance acidic hydrolysis using aqueous HCl. If $R^{10}$ is $OCH_3$ the conversion into (I) may be carried out by reaction with for instance TMSI in a suitable solvent such as chloroform or by reaction with HBr in a suitable solvent such as acetic acid or by reaction with $BBr_3$ in a suitable solvent such as dichloromethane. If $R^{10}$ is $OC(CH_3)_3$ the conversion into (I) may be carried out by reaction with for instance trifluoroacetic acid in a suitable solvent such as dichloromethane. If $R^{10}$ is $OSiR'R''R'''$ the conversion into (I) may be carried out by for instance HCl in a suitable solvent such as methanol or by using tetrabutyl ammonium fluoride in tetrahydrofuran. If enantiomerically pure or enriched compound (III) is used in this reaction, an enantiomerically pure or enantiomerically enriched compound (I) is obtained.

Compounds of formula (II), (III) and coupling partner A* are commercially available compounds, or are known in the literature, or they are prepared by standard processes known in the art. A compound of formula (I), (II) or (III) may be separated into its enantiomers by standard processes known in the art by for example chromatography on a chiral stationary phase.

General Methods

All solvents used were of analytical grade and commercially available anhydrous solvents were routinely used for reactions. Starting materials were available from commercial sources, or prepared according to literature procedures. Room temperature refers to +20-25° C. Solvent mixture compositions are given as volume percentages or volume ratios.

Microwave heating was performed in a Biotage Initiator microwave cavity producing continuous irradiation at 2.45 GHz. It is understood that microwaves may be used for the heating of reaction mixtures.

Straight phase chromatography was manually performed on Merck Silica gel 60 (0.040-0.063 mm), or automatically using an ISCO Combiflash® Companion™ system using SiliaSep™ normal-phase flash columns using the solvent system indicated.

NMR spectra were recorded on a 400 MHz (or higher field) NMR spectrometer fitted with a probe of suitable configuration. Spectra were recorded at ambient temperature unless otherwise stated. NMR spectra were acquired in $CDCl_3$, DMSO-$d_6$ or $CD_3OD$. Chemical shifts are given in ppm down- and upfield from TMS (0.00 ppm). The following reference signals were used: the residual solvent signal of DMSO-$d_5$ δ 2.5 or the residual solvent signal of $CHCl_3$ δ 7.26 or the residual solvent of $CD_2HOD$ 3.31. Resonance multiplicities are denoted s, d, t, q, m and br for singlet, doublet, triplet, quartet, multiplet and broad, respectively.

High pressure (performance) liquid chromatography (HPLC) was performed on a reverse phase column. A linear gradient was applied using for example mobile phase A (aqueous 0.1% NH$_3$ or aqueous 0.1% acetic acid or aqueous 0.1% formic acid) and B (acetonitrile or methanol). Mass spectrometry (MS) analyses were performed in positive ion mode using electrospray ionization (ES+).

Preparative chromatography was run on a Gilson-PREP GX271 or GX281 with Trilution Ic as software on a reverse phase column. A linear gradient was applied using for example mobile phase A (aqueous 0.1% NH$_3$ or aqueous 0.1% acetic acid or aqueous 0.1% formic acid) and B (acetonitrile or methanol).

Preparative chiral chromatography for separation of enantiomers was run on a Thar SFC using supercritical fluid chromatography on a chiral stationary phase. A linear gradient was applied using mobile phase A (carbon dioxide) and B (acetonitrile or methanol or ethanol or 2-propanol or any mixtures thereof). Additives (such as diethyl amine or isopropyl amine or ammonia or formic acid or TFA) may be used.

Compounds have been named using Accelrys Draw 4.1 SP1.

Intermediate Example 1

4-(2,6-dichloro-4-pyridyl)morpholine

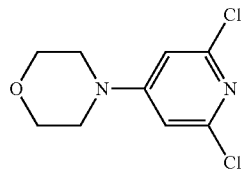 [SMILES: Clc1cc(N2CCOCC2)cc(Cl)n1]

2,6-dichloro-4-iodo-pyridine (6 g, 21.91 mmol), morpholine (2 ml, 23.12 mmol), PPh$_3$ (350 mg, 1.33 mmol), Pd(OAc)$_2$ (150 mg, 0.67 mmol) and freshly ground K$_3$PO$_4$ (13 g, 61.24 mmol) were taken up in DMF (40 ml) and the resulting mixture was stirred vigorously while being degassed with nitrogen for 5 min. The mixture was lowered into a pre-heated oilbath and stirred at 100° C. for 1 h. When cooled to rt the mixture was poured into water (150 ml) and EtOAc (50 ml). The organic layer was separated and the aqueous layer extracted with EtOAc (3×30 ml). The combined organics were washed with brine, dried over Na$_2$SO$_4$, filtered, concentrated and purified on a silica gel column eluted with 10-60% EtOAc in heptane to give the title compound (2.53 g, 49%). MS ES+ m/z 233 [M+H]$^+$.

Intermediate Example 2

4-(2-tert-butoxy-6-chloro-4-pyridyl)morpholine

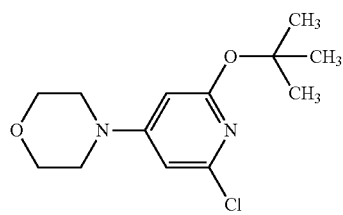 [SMILES: CC(C)(C)Oc1cc(N2CCOCC2)cc(Cl)n1]

4-(2,6-dichloro-4-pyridyl)morpholine (3.2 g, 13.73 mmol), KOtBu (3.85 g, 34.32 mmol) and 4 Å molecular sieves (~10 beads, 4-8 mesh) were taken up in anh. Toluene (50 ml) and stirred at 90° C. for 2 h. When cooled to rt the mixture was diluted with EtOAc (30 ml), brine (40 ml) and water (20 ml). The organic layer was separated and the aqueous layer extracted with EtOAc (2×25 ml). The combined organics were washed with brine, dried over Na$_2$SO$_4$, filtered, concentrated and purified on a silica gel column eluted with 0-40% EtOAc in heptane to give the title compound (3.4 g, 91%). MS ES+m/z 271 [M+H]$^+$.

Intermediate Example 3

4-[2-tert-butoxy-6-(2-phenylpyrrolidin-1-yl)-4-pyridyl]morpholine

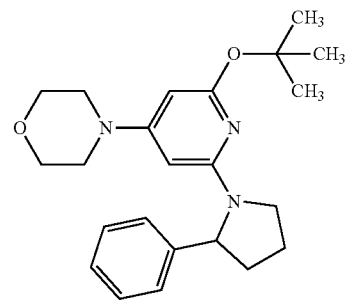 [SMILES: CC(C)(C)Oc1cc(N2CCOCC2)cc(N2CCCC2c2ccccc2)n1]

4-(2-tert-butoxy-6-chloro-4-pyridyl)morpholine (3.55 g, 13.11 mmol), 2-phenylpyrrolidine (2.8 g, 19.02 mmol), PEPPSI™-iPr (460 mg, 0.68 mmol) and KOtBu (2.5 g, 22.28 mmol) were taken up in anh. 1,4-Dioxane (50 ml) and degassed with nitrogen for 5 min. The resulting mixture was stirred at 50° C. for 1 h. When cooled to rt brine (25 ml), water (15 ml) and EtOAc (25 ml) were added. The organic layer was separated and the aqueous layer was extracted with EtOAc (2×20 ml). The combined organics were washed with brine, dried over Na$_2$SO$_4$, filtered, concentrated and purified on a silica gel column eluted with 0-50% EtOAc in heptane to give the title compound (5 g, 99%). MS ES+ m/z 382 [M+H]$^+$.

Example 1

4-morpholino-6-(2-phenylpyrrolidin-1-yl)-1H-pyridin-2-one

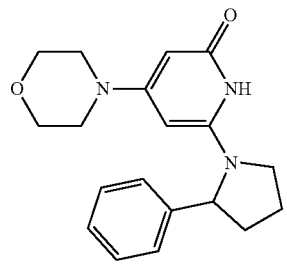

4-[2-tert-butoxy-6-(2-phenylpyrrolidin-1-yl)-4-pyridyl]morpholine (5 g, 13.11 mmol) was dissolved in DCM (40 ml) and TFA (2.92 ml, 39.32 mmol) was added slowly at rt.

The resulting mixture was stirred at rt for 1 h. More TFA (2 ml, 26.92 mmol) was added and stirring continued at rt for 2.5 h. The mixture was concentrated and the residue was taken up in EtOAc (50 ml) and cooled to 0° C. 28% NH₄OH (30 ml) was added slowly and the mixture was stirred vigorously for 10 min. The precipitate was filtered off, washed with water (2×5 ml), EtOAc (2×5 ml) and dried. The solid was suspended in EtOAc:heptane (1:1, 30 ml) and stirred at rt for 15 min and then filtered. The filter cake was washed with EtOAc:heptane (1:1, 2×10 ml), then suspended in pentane (10 ml), filtered, and dried to give the title compound (2.3 g, 54%). $^1$H NMR (500 MHz, DMSO-d$_6$) δ 7.30 (t, 2H), 7.24-7.16 (m, 3H), 5.07-4.98 (m, 2H), 4.91 (s, 1H), 3.78-3.71 (m, 1H), 3.67-3.55 (m, 4H), 3.52-3.42 (m, 1H), 3.11-3.01 (m, 2H), 3.01-2.95 (m, 2H), 2.36-2.29 (m, 1H), 1.94-1.82 (m, 2H), 1.82-1.75 (m, 1H). MS ES+ m/z 326 [M+H]⁺.

Example 2

1-methyl-4-morpholino-6-(2-phenylpyrrolidin-1-yl)pyridin-2-one

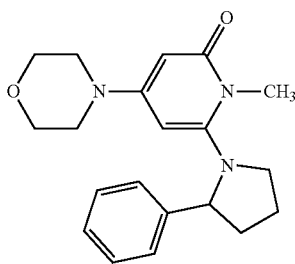 [SMILES: Cn1c(N2CCCC2c2ccccc2)cc(N2CCOCC2)cc1=O]

4-morpholino-6-(2-phenylpyrrolidin-1-yl)-1H-pyridin-2-one (75 mg, 0.23 mmol) and K₂CO₃ (50 mg, 0.36 mmol) were taken up in MeCN (1 ml). Iodomethane (0.02 ml, 0.32 mmol) was added and the mixture was stirred at rt for 30 min. DMAc (0.5 ml) was added and the mixture was stirred at rt overnight. MeOH (1 ml) and iodomethane (0.05 ml, 0.8 mmol) were added and stirring continued at rt overnight. The mixture was filtered and purified by preparative HPLC to give the title compound (5 mg, 6%). MS ES+ m/z 340 [M+H]⁺.

Intermediate Example 4

4-[2-tert-butoxy-6-[(2S)-2-phenylpyrrolidin-1-yl]-4-pyridyl]morpholine

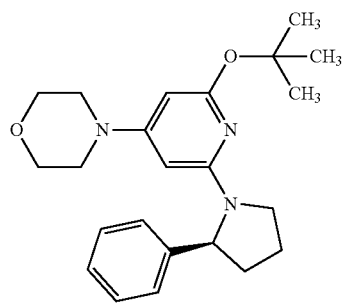 [SMILES: CC(C)(C)Oc1cc(N2CCOCC2)cc(N2CCC[C@H]2c2ccccc2)n1]

4-(2-tert-butoxy-6-chloro-4-pyridyl)morpholine (120 mg, 0.44 mmol), (2S)-2-phenylpyrrolidine (98 mg, 0.66 mmol), Pd₂(dba)₃ (20 mg, 0.02 mmol), XantPhos (25 mg, 0.04 mmol) and KOtBu (150 mg, 1.33 mmol) were taken up in toluene (3 ml) and resulting mixture was stirred at 100° C. over weekend. More Pd₂(dba)₃ (20 mg, 0.02 mmol), XantPhos (25 mg, 0.04 mmol) and KOtBu (150 mg, 1.33 mmol) were added and stirring was continued at 100° C. overnight. More Pd₂(dba)₃ (20 mg, 0.02 mmol), XantPhos (25 mg, 0.04 mmol) and KOtBu (150 mg, 1.33 mmol) were added and stirring was continued at 100° C. for 5 h. When cooled to rt EtOAc (5 ml) and brine (10 ml) were added. The mixture was filtered, the organic layer separated and the aqueous layer was extracted with EtOAc (2×5 ml). The combined organics were dried over Na₂SO₄, filtered, concentrated and purified on a silica gel column eluted with 0-40% EtOAc in heptane to give the title compound (75 mg, 44%). MS ES+ m/z 382 [M+H]⁺.

Example 3

4-morpholino-6-[(2S)-2-phenylpyrrolidin-1-yl]-1H-pyridin-2-one

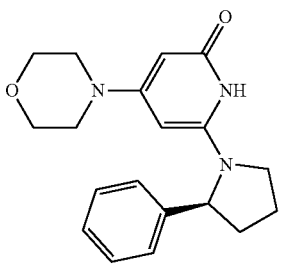 [SMILES: O=c1cc(N2CCOCC2)cc(N2CCC[C@H]2c2ccccc2)[nH]1]

4-[2-tert-butoxy-6-[(2S)-2-phenylpyrrolidin-1-yl]-4-pyridyl]morpholine (75 mg, 0.2 mmol) was dissolved in DCM (3 ml) and TFA (73 μl, 0.98 mmol) was added. The resulting mixture was stirred at rt for 3 h, concentrated and purified by preparative HPLC to give the title compound (23 mg, 36%). $^1$H NMR (500 MHz, DMSO-d$_6$) δ 7.38-7.26 (m, 2H), 7.26-7.12 (m, 3H), 5.08-4.94 (m, 2H), 4.88 (s, 1H), 3.78-3.68 (m, 1H), 3.65-3.52 (m, 4H), 3.50-3.41 (m, 1H), 3.13-2.89 (m, 4H), 2.38-2.27 (m, 1H), 1.96-1.82 (m, 2H), 1.82-1.71 (m, 1H). MS ES+ m/z 326 [M+H]⁺.

Example 4

4-morpholino-6-[(2R)-2-phenylpyrrolidin-1-yl]-1H-pyridin-2-one

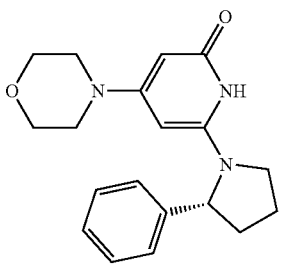 [SMILES: O=c1cc(N2CCOCC2)cc(N2CCC[C@@H]2c2ccccc2)[nH]1]

4-(2-tert-butoxy-6-chloro-4-pyridyl)morpholine (300 mg, 1.11 mmol), (2R)-2-phenylpyrrolidine (245 mg, 1.66 mmol), Pd$_2$(dba)$_3$ (51 mg, 0.06 mmol), XPhos (53 mg, 0.11 mmol) and KOtBu (373 mg, 3.32 mmol) were taken up in toluene (5 ml) and the resulting mixture was stirred at 105° C. for 2 h. When cooled to rt EtOAc (5 ml) and brine (10 ml) were added. The mixture was filtered, the organic layer separated and the aqueous layer was extracted with EtOAc (2×5 ml). The combined organics were dried over Na$_2$SO$_4$, filtered, concentrated and purified on a silica gel column eluted with 0-40% EtOAc in heptane. The resulting material was taken up in DCM (5 ml) and TFA (0.31 ml, 4.19 mmol) was added. The reaction mixture was stirred at rt for 45 min. More TFA (0.31 ml, 4.19 mmol) was added and stirring continued for 1 h. The mixture was concentrated and the residue taken up in EtOAc (5 ml) and 2M aq HCl (2 ml). The organic layer was separated and the aqueous layer was extracted with EtOAc (2×3 ml). The combined organics were washed with brine, dried over Na$_2$SO$_4$, filtered, concentrated and purified by preparative HPLC to give the title compound (52 mg, 19%). $^1$H NMR (500 MHz, DMSO-d$_6$) δ 9.50 (br s, 1H), 7.34-7.27 (m, 2H), 7.24-7.15 (m, 3H), 5.04-4.96 (m, 2H), 4.88 (br s, 1H), 3.78-3.68 (m, 1H), 3.63-3.53 (m, 4H), 3.49-3.41 (m, 1H), 3.07-3.00 (m, 2H), 3.00-2.93 (m, 2H), 2.38-2.26 (m, 1H), 1.94-1.81 (m, 2H), 1.78 (dd, 1H). MS ES+ m/z 326 [M+H]$^+$.

Intermediate Example 5

4-(2,6-dichloro-4-pyridyl)-3-methyl-morpholine

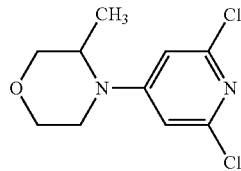

2,6-dichloro-4-iodo-pyridine (1.5 g, 5.48 mmol), 3-methylmorpholine (0.61 ml, 6.02 mmol), PPh$_3$ (144 mg, 0.55 mmol), Pd(OAc)$_2$ (61 mg, 0.27 mmol) and freshly ground K$_3$PO$_4$ (3.49 g, 16.43 mmol) were taken up in DMF (30 ml) and the resulting mixture was stirred at 100° C. for 1 h. When cooled to rt the mixture was poured into water (50 ml) and extracted with EtOAc (3×15 ml). The combined organics were washed with brine, dried over Na$_2$SO$_4$, filtered, concentrated and purified on a silica gel column eluted with 0-60% EtOAc in heptane to give the title compound (800 mg, 59%). MS ES+ m/z 247 [M+H]$^+$.

Intermediate Example 6

4-(2-tert-butoxy-6-chloro-4-pyridyl)-3-methyl-morpholine

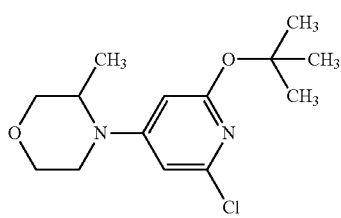 [SMILES: CC1COCCN1c1cc(Cl)nc(OC(C)(C)C)c1]

4-(2,6-dichloro-4-pyridyl)-3-methyl-morpholine (2.2 g, 8.9 mmol), KOtBu (2.5 g, 22.26 mmol) and 4 Å molecular sieves (~10 beads, 4-8 mesh) were taken up in anh. Toluene (40 ml) and stirred at 90° C. for 2 h. When cooled to rt the mixture was diluted with EtOAc (30 ml), brine (40 ml) and water (20 ml). The organic layer was separated and the aqueous layer extracted with EtOAc (2×25 ml). The combined organics were washed with brine, dried over Na$_2$SO$_4$, filtered, concentrated and purified on a silica gel column eluted with 0-40% EtOAc in heptane to give the title compound (2.2 g, 87%). MS ES+ m/z 285 [M+H]$^+$.

Example 5

6-(3,6-dihydro-2H-pyran-4-yl)-4-(3-methylmorpholin-4-yl)-1H-pyridin-2-one

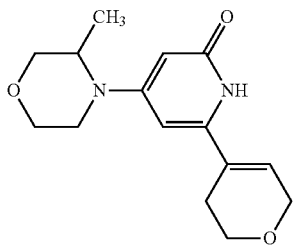 [SMILES: CC1COCCN1c1cc(C2=CCOCC2)[nH]c(=O)c1]

4-(2-tert-butoxy-6-chloro-4-pyridyl)-3-methyl-morpholine (0.2 g, 0.7 mmol), 2-(3,6-dihydro-2H-pyran-4-yl)-4,4,5,5-tetramethyl-1,3,2-dioxaborolane (0.18 g, 0.84 mmol), PdCl$_2$(amphos) (4.97 mg, 7.02 µmol) and K$_2$CO$_3$ (291.18 mg, 2.11 mmol) were dissolved in 2-MeTHF (3 ml) and Water (1 ml) and the resulting mixture was heated in a microwave reactor at 135° C. for 1 h. When cooled to rt, brine (5 ml), water (4 ml) and EtOAc (5 ml) were added. The organic layer was separated and the aqueous layer was extracted with EtOAc (2×10 ml). The combined organics were washed with brine, dried over MgSO$_4$, filtered and concentrated. The crude material was taken up in DCM (5 ml) and TFA (345.93 mg, 3.03 mmol) was added. The reaction mixture was stirred at r.t. overnight. The mixture was concentrated and the resulting residue was dissolved in EtOAc and washed with sat. aq. NaHCO$_3$ (2×10 ml). The organic layer was concentrated and purified by preparative HPLC to give the product as a solid (80 mg, 41%). $^1$H NMR (400 MHz, DMSO-d$_6$) δ 10.46 (br s, 1H), 6.51 (br s, 1H), 5.99 (s, 1H), 5.32 (s, 1H), 4.18 (br s, 2H), 3.96 (br d, 1H), 3.88 (br d, 1H), 3.79-3.57 (m, 4H), 3.49-3.33 (m, 2H), 3.02 (td, 1H), 2.37 (br s, 2H), 1.08 (d, 3H). MS ES+ m/z 277 [M+H]$^+$.

Example 6

4-(3-methylmorpholin-4-yl)-6-tetrahydropyran-4-yl-1H-pyridin-2-one

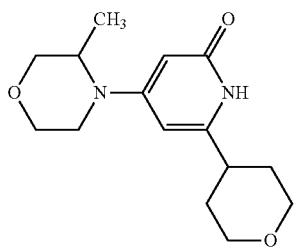 [SMILES: CC1COCCN1c1cc(C2CCOCC2)[nH]c(=O)c1]

6-(3,6-dihydro-2H-pyran-4-yl)-4-(3-methylmorpholin-4-yl)-1H-pyridin-2-one (80 mg, 0.29 mmol), 10% Pd on carbon (120 mg, 1.16 mmol) and ammonium formate (110 mg, 1.74 mmol) were dissolved in MeOH (4 ml) under nitrogen and the resulting mixture was stirred at 50° C. for 1 h. When cooled to rt the mixture was filtered and purified on preparative HPLC to give the product as a solid (30 mg, 37%). $^1$H NMR (400 MHz, CD$_3$OD) δ 6.05 (s, 1H), 5.54 (s, 1H), 4.06-3.94 (m, 4H), 3.80-3.68 (m, 2H), 3.61-3.42 (m, 4H), 3.20 (td, 1H), 2.76-2.66 (m, 1H), 1.86-1.72 (m, 4H), 1.26-1.18 (m, 3H). MS ES+ m/z 279 [M+H]$^+$.

Example 7

6-[2-(3-methoxyphenyl)pyrrolidin-1-yl]-4-(3-methylmorpholin-4-yl)-1H-pyridin-2-one

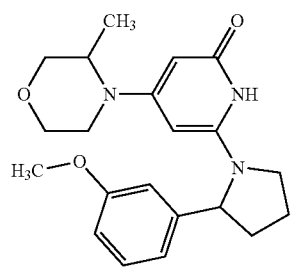 [SMILES: COc1cccc(C2CCCN2c2cc(N3CCOCC3C)cc(=O)[nH]2)c1]

4-(2-tert-butoxy-6-chloro-4-pyridyl)-3-methyl-morpholine (200 mg, 0.7 mmol), 2-(3-methoxyphenyl)pyrrolidine (150 mg, 0.84 mmol), PEPPSI™-iPr (24 mg, 0.04 mmol) and KOtBu (160 mg, 1.4 mmol) were taken up in anh. 1,4-Dioxane (5 ml) and degassed with nitrogen for 5 min. The resulting mixture stirred at 90° C. for 1 h. When cooled to rt brine (5 ml), water (4 ml) and EtOAc (5 ml) were added. The organic layer was separated and the aqueous layer extracted with EtOAc (2×10 ml). The combined organics were washed with brine, filtered and concentrated. The resulting residue was dissolved in DCM (10 ml) and TFA (0.38 ml, 5.06 mmol) was added slowly at rt. The resulting mixture was stirred at rt overnight. The mixture was concentrated and purified by preparative HPLC to give the title compound (90 mg, 37%). $^1$H NMR (500 MHz, DMSO-d$_6$) δ 9.50 (br s, 1H), 7.23 (td, 1H), 6.71-6.82 (m, 3H), 4.90-5.02 (m, 1H), 4.88 (br s, 1H), 4.81 (br s, 1H), 3.68-3.84 (m, 5H), 3.57-3.67 (m, 2H), 3.33-3.55 (m, 4H), 3.18 (br d, 1H), 3.09 (br d, 1H), 2.81-2.93 (m, 1H), 2.27-2.48 (m, 1H), 1.83-1.95 (m, 2H), 1.79 (br dd, 1H), 1.05 (d, 1H), 0.77 (br d, 2H). MS ES+ m/z 370 [M+H]$^+$.

Example 8

4-(3-methylmorpholin-4-yl)-6-[2-(3-pyridyl)pyrrolidin-1-yl]-1H-pyridin-2-one

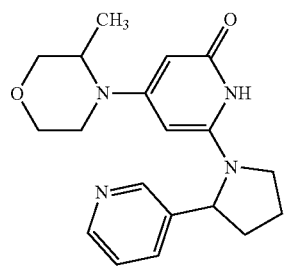 [SMILES: CC1COCCN1c1cc(N2CCCC2c2cccnc2)[nH]c(=O)c1]

The title compound was prepared as described in Example 7, starting from 4-(2-tert-butoxy-6-chloro-4-pyridyl)-3-methyl-morpholine (200 mg, 0.7 mmol) and 3-pyrrolidin-2-ylpyridine (120 mg, 0.84 mmol) to give the product (80 mg, 34%). $^1$H NMR (500 MHz, DMSO-d$_6$) δ 10.72 (br s, 1H), 8.40-8.49 (m, 2H), 7.57 (t, 1H), 7.33 (dt, 1H), 5.10 (br d, 1H), 4.96-5.05 (m, 1H), 4.93 (br s, 1H), 3.72-3.86 (m, 2H), 3.59-3.70 (m, 2H), 3.37-3.55 (m, 3H), 3.16-3.31 (m, 1H), 3.11 (br d, 1H), 2.87 (qd, 1H), 2.30-2.48 (m, 1H), 1.81-1.97 (m, 6H), 1.04 (d, 2H), 0.76 (br d, 1H). MS ES+ m/z 341 [M+H]$^+$.

Example 9

4-(3-methylmorpholin-4-yl)-6-(2-phenylpyrrolidin-1-yl)-1H-pyridin-2-one

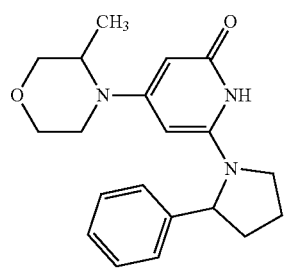 [SMILES: CC1COCCN1c1cc(N2CCCC2c2ccccc2)[nH]c(=O)c1]

The title compound was prepared as described in Example 7, starting from 4-(2-tert-butoxy-6-chloro-4-pyridyl)-3-methyl-morpholine (200 mg, 0.7 mmol) and 2-phenylpyrrolidine (120 mg, 0.84 mmol) to give the product (110 mg, 46%). $^1$H NMR (500 MHz, DMSO-d$_6$) δ 9.54 (br s, 1H), 7.26-7.36 (m, 2H), 7.17-7.26 (m, 3H), 4.89-5.06 (m, 2H), 4.73-4.88 (m, 1H), 3.70-3.86 (m, 2H), 3.55-3.65 (m, 2H), 3.33-3.55 (m, 4H), 3.17 (br d, 1H), 3.08 (br d, 1H), 2.79-2.94 (m, 1H), 2.28-2.48 (m, 1H), 2.08 (s, 1H), 1.84-1.97 (m, 2H), 1.75-1.84 (m, 1H), 1.04 (d, 1H), 0.74 (br d, 2H). MS ES+ m/z 340 [M+H]$^+$.

Intermediate Example 7

(3R)-4-(2,6-dichloro-4-pyridyl)-3-methyl-morpholine

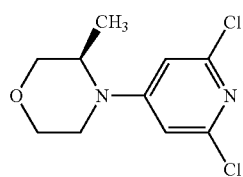

The title compound was prepared as described in Intermediate example 5, replacing 3-methylmorpholine with (R)-3-methylmorpholine, to give the product (900 mg, 66%). MS ES+ m/z 247 [M+H]+.

Intermediate Example 8

(3R)-4-(2-tert-butoxy-6-chloro-4-pyridyl)-3-methyl-morpholine

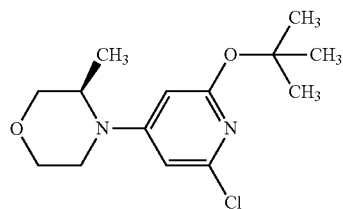 [SMILES: C[C@@H]1COCCN1c1cc(Cl)nc(OC(C)(C)C)c1]

The title compound was prepared as described in Intermediate example 6, starting from (3R)-4-(2,6-dichloro-4-pyridyl)-3-methyl-morpholine (700 mg), to give the product (510 mg, 63%). $^1$H NMR (400 MHz, CDCl$_3$) δ 6.29 (s, 1H), 5.92-5.81 (m, 1H), 4.04-3.92 (m, 1H), 3.85-3.69 (m, 3H), 3.65-3.52 (m, 1H), 3.29-3.10 (m, 2H), 1.59-1.53 (m, 9H), 1.21 (d, 3H). MS ES+ m/z 285 [M+H]+.

Intermediate Example 9

1-[6-tert-butoxy-4-[(3R)-3-methylmorpholin-4-yl]-2-pyridyl]-N,N-dimethyl-pyrrolidine-2-carboxamide

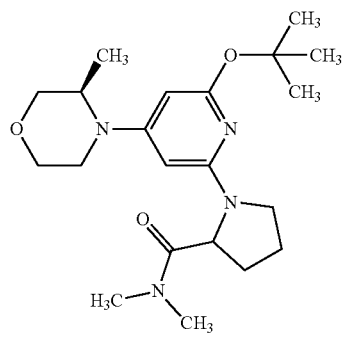 [SMILES: C[C@@H]1COCCN1c1cc(OC(C)(C)C)nc(N2CCCC2C(=O)N(C)C)c1]

(3R)-4-(2-tert-butoxy-6-chloro-4-pyridyl)-3-methyl-morpholine (250 mg, 0.88 mmol), N,N-dimethylpyrrolidine-2-carboxamide HCl salt (188 mg, 1.05 mmol), PEPPSI™-iPr (30 mg, 0.044 mmol) and KOtBu (197 mg, 1.76 mmol) were taken up in anh. 1,4-Dioxane (5 ml) and degassed with nitrogen for 5 min. The resulting mixture was stirred at 90° C. for 1 h. When cooled to rt the mixture was filtered through celite and the filtrate diluted with water and extracted with ethyl acetate. The combined organics were washed with brine, dried over Na$_2$SO$_4$, filtered, concentrated and purified on a silica gel column eluted with 20% EtOAc/Petroleum ether to give the title compound (160 mg, 46%). MS ES+ m/z 391 [M+H]+.

Example 10

N,N-dimethyl-1-[4-[(3R)-3-methylmorpholin-4-yl]-6-oxo-1H-pyridin-2-yl]pyrrolidine-2-carboxamide

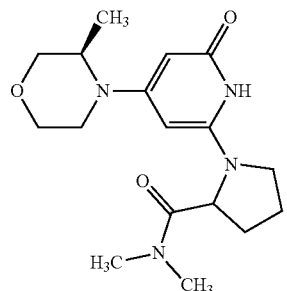

TFA (0.29 ml, 3.8 mmol) was added to a solution of 1-[6-tert-butoxy-4-[(3R)-3-methylmorpholin-4-yl]-2-pyridyl]-N,N-dimethyl-pyrrolidine-2-carboxamide (150 mg, 0.38 mmol) in DCM (3 ml) at 0° C. and the resulting mixture was stirred at rt overnight. The reaction mixture was basified with sat. aq. NaHCO$_3$ and extracted with DCM. The combined organics were washed with brine, dried over Na$_2$SO$_4$, filtered, concentrated and purified on a silica gel column eluted with 5% MeOH/DCM to give the title compound (50 mg, 39%). $^1$H NMR (400 MHz, CDCl$_3$) δ 5.21-5.02 (m, 2H), 4.83 (s, 1H), 3.95 (br d, 1H), 3.81-3.69 (m, 3H), 3.64-3.53 (m, 2H), 3.41 (dt, 1H), 3.27-3.14 (m, 2H), 3.09 (s, 3H), 2.92 (d, 3H), 2.39-2.32 (m, 1H), 2.09-1.93 (m, 3H), 1.27-1.15 (m, 3H). MS ES+ m/z 335 [M+H]+.

Intermediate Example 10

(3R)-4-[2-tert-butoxy-6-[2-(1-methoxy-1-methyl-ethyl)pyrrolidin-1-yl]-4-pyridyl]-3-methyl-morpholine

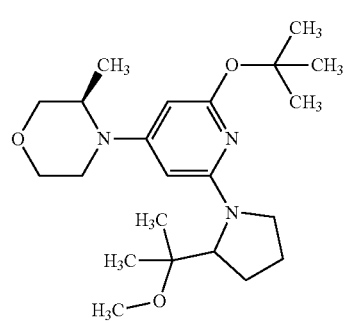 [SMILES: COC(C)(C)C1CCCN1c1cc(N2CCOC[C@H]2C)cc(OC(C)(C)C)n1]

The title compound was prepared as described in Intermediate example 9, starting from (3R)-4-(2-tert-butoxy-6-chloro-4-pyridyl)-3-methyl-morpholine (500 mg, 1.76 mmol) and 2-(1-methoxy-1-methyl-ethyl)pyrrolidine (302 mg, 2.11 mmol), to give the product (375 mg, 54%). MS ES+ m/z 392 [M+H]+.

Example 11

(R) and (S) 6-[2-(1-methoxy-1-methyl-ethyl)pyrrolidin-1-yl]-4-[(3R)-3-methylmorpholin-4-yl]-1H-pyridin-2-one

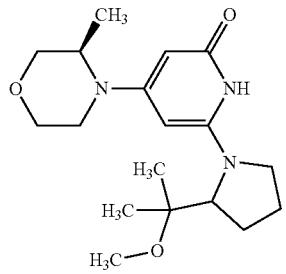 [SMILES: COC(C)(C)C1CCCN1c1cc(N2CCOC[C@H]2C)cc(=O)[nH]1]

The title compound was prepared as described in Example 10, starting from (3R)-4-[2-tert-butoxy-6-[2-(1-methoxy-1-methyl-ethyl)pyrrolidin-1-yl]-4-pyridyl]-3-methyl-morpholine (350 mg, 0.89 mmol) to give the product as a diastereomeric mixture (170 mg, 57%). 1H NMR (400 MHz, CDCl3) δ 10.48 (br s, 1H), 5.25 (s, 1H), 4.94-4.91 (m, 1H), 3.96 (br dd, 1H), 3.83-3.72 (m, 4H), 3.62-3.54 (m, 1H), 3.37-3.15 (m, 7H), 2.07-1.86 (m, 4H), 1.32-1.18 (m, 6H), 1.08 (d, 3H). MS ES+ m/z 336 [M+H]+. Chiral separation by SFC gave the two isomers.

Example 11-1, First Isomer to Elute, with Unknown Absolute Configuration

1H NMR (400 MHz, CDCl3) δ 10.70-10.44 (m, 1H), 5.33-5.21 (m, 1H), 4.99-4.88 (m, 1H), 3.96 (br dd, 1H), 3.85-3.71 (m, 4H), 3.58 (td, 1H), 3.39-3.29 (m, 5H), 3.28-3.16 (m, 2H), 2.08-1.85 (m, 4H), 1.27-1.19 (m, 6H), 1.09 (s, 3H). MS ES+ m/z 336 [M+H]+.

Example 11-2, Second Isomer to Elute, with Unknown Absolute Configuration

1H NMR (400 MHz, CDCl3) δ 10.62-10.40 (m, 1H), 5.25 (s, 1H), 4.93 (s, 1H), 3.96 (br dd, 1H), 3.85-3.68 (m, 4H), 3.58 (td, 1H), 3.41-3.26 (m, 5H), 3.19 (td, 1H), 2.10-1.87 (m, 5H), 1.28-1.17 (m, 6H), 1.08 (s, 3H). MS ES+ m/z 336 [M+H]+.

Intermediate Example 11

(3R)-4-[2-tert-butoxy-6-(2-cyclohexylpyrrolidin-1-yl)-4-pyridyl]-3-methyl-morpholine

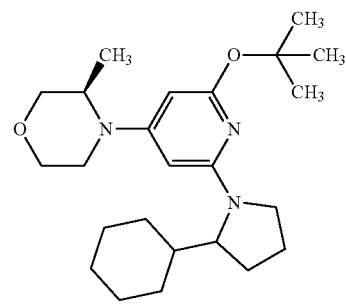 [SMILES: C[C@@H]1COCCN1c1cc(OC(C)(C)C)nc(N2CCCC2C2CCCCC2)c1]

The title compound was prepared as described in Intermediate example 9, starting from (3R)-4-(2-tert-butoxy-6-chloro-4-pyridyl)-3-methyl-morpholine (500 mg, 1.76 mmol) and 2-cyclohexylpyrrolidine (323 mg, 2.11 mmol), to give the product (310 mg, 44%). MS ES+ m/z 402 [M+H]+.

Example 12

(R) and (S) 6-(2-cyclohexylpyrrolidin-1-yl)-4-[(3R)-3-methylmorpholin-4-yl]-1H-pyridin-2-one

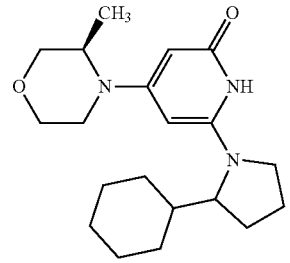 [SMILES: C[C@@H]1COCCN1c1cc(N2CCCC2C2CCCCC2)[nH]c(=O)c1]

The title compound was prepared as described in Example 10, starting from (3R)-4-[2-tert-butoxy-6-(2-cyclohexylpyrrolidin-1-yl)-4-pyridyl]-3-methyl-morpholine (300 mg, 0.75 mmol) to give the product as a diastereomeric mixture (218 mg, 81%). 1H NMR (400 MHz, CDCl3) δ 5.19 (s, 1H), 4.82 (br s, 1H), 3.97 (br d, 1H), 3.83-3.72 (m, 3H), 3.68-3.55 (m, 2H), 3.39 (br s, 1H), 3.33-3.18 (m, 3H), 2.04-1.88 (m, 4H), 1.80-1.61 (m, 7H), 1.27-1.22 (m, 3H), 1.16-0.96 (m, 4H). MS ES+ m/z 346 [M+H]+. Chiral separation by SFC gave the two isomers.

Example 12-1, First Isomer to Elute, with Unknown Absolute Configuration

1H NMR (400 MHz, CDCl3) δ 5.17 (br s, 1H), 4.81 (br s, 1H), 3.97 (br d, 1H), 3.81-3.70 (m, 3H), 3.68-3.56 (m, 2H), 3.38 (br s, 1H), 3.31-3.17 (m, 3H), 2.06-1.87 (m, 4H), 1.81-1.50 (m, 8H), 1.23 (br d, 3H), 1.17-1.08 (m, 3H). MS ES+ m/z 346 [M+H]+.

Example 12-2, Second Isomer to Elute, with Unknown Absolute Configuration

1H NMR (400 MHz, CDCl3) δ 5.19 (br s, 1H), 4.82 (br s, 1H), 3.97 (br d, 1H), 3.82-3.56 (m, 5H), 3.39 (br s, 1H), 3.32-3.16 (m, 3H), 1.99 (br s, 4H), 1.74 (br s, 8H), 1.24 (br d, 3H), 1.14-1.00 (m, 3H). MS ES+ m/z 346 [M+H]+.

Intermediate Example 12

(3R)-4-[2-tert-butoxy-6-[2-(3-fluorophenyl)pyrrolidin-1-yl]-4-pyridyl]-3-methyl-morpholine

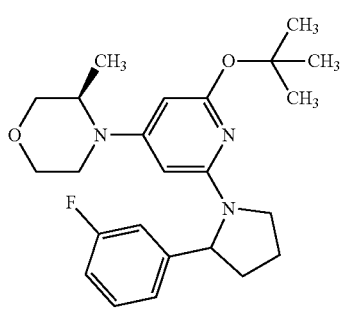 [SMILES: C[C@@H]1COCCN1c1cc(OC(C)(C)C)nc(N2CCCC2c2cccc(F)c2)c1]

The title compound was prepared as described in Intermediate example 9 except the mixture was stirred for 3 h, starting from (3R)-4-(2-tert-butoxy-6-chloro-4-pyridyl)-3-methyl-morpholine (650 mg, 2.28 mmol) and 2-(3-fluorophenyl)pyrrolidine (453 mg, 2.74 mmol), to give the product (373 mg, 39%). MS ES+ m/z 414 [M+H]+.

Example 13

(R) and (S) 6-[2-(3-fluorophenyl)pyrrolidin-1-yl]-4-[(3R)-3-methylmorpholin-4-yl]-1H-pyridin-2-one

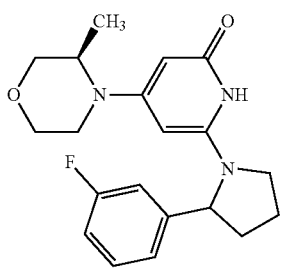 [SMILES: C[C@@H]1COCCN1c1cc(N2CCCC2c2cccc(F)c2)[nH]c(=O)c1]

The title compound was prepared as described in Example 10, starting from (3R)-4-[2-tert-butoxy-6-[2-(3-fluorophenyl)pyrrolidin-1-yl]-4-pyridyl]-3-methyl-morpholine (430 mg, 1.04 mmol) to give the product as a diastereomeric mixture (300 mg, 81%). ¹H NMR (400 MHz, CDCl₃) δ 7.29 (br d, 1H), 6.99-6.94 (m, 2H), 6.88 (br d, 1H), 5.14 (dd, 1H), 4.81-4.64 (m, 2H), 3.95-3.88 (m, 1H), 3.77-3.64 (m, 3H), 3.58-3.45 (m, 3H), 3.19-3.05 (m, 2H), 2.49-2.37 (m, 1H), 2.08-1.92 (m, 3H), 1.20 (d, 1.5H), 0.97 (br d, 1.5H). MS ES+ m/z 358 [M+H]+. Chiral separation by SFC gave the two isomers.

Example 13-1, First Isomer to Elute, with Unknown Absolute Configuration

¹H NMR (400 MHz, CDCl₃) δ 7.31 (br d, 1H), 7.01-6.94 (m, 2H), 6.87 (br d, 1H), 5.16 (br s, 1H), 4.79-4.72 (m, 2H), 3.92 (br d, 1H), 3.73-3.62 (m, 4H), 3.58-3.45 (m, 2H), 3.19-3.06 (m, 2H), 2.48-2.38 (m, 1H), 2.08-1.94 (m, 3H), 1.20 (br d, 3H). MS ES+ m/z 358 [M+H]+.

Example 13-2, Second Isomer to Elute, with Unknown Absolute Configuration

¹H NMR (400 MHz, CDCl₃) δ 7.30 (br d, 1H), 7.00-6.93 (m, 2H), 6.88 (br d, 1H), 5.16 (s, 1H), 4.75 (br dd, 1H), 4.67 (s, 1H), 3.92 (br d, 1H), 3.75 (br d, 1H), 3.67 (s, 2H), 3.59-3.47 (m, 3H), 3.13-3.08 (m, 2H), 2.45 (qd, 1H), 2.10-1.94 (m, 3H), 0.98 (d, 3H). MS ES+ m/z 358 [M+H]+.

Intermediate Example 13

(3R)-4-[2-tert-butoxy-6-[2-(2,5-difluorophenyl)pyrrolidin-1-yl]-4-pyridyl]-3-methyl-morpholine

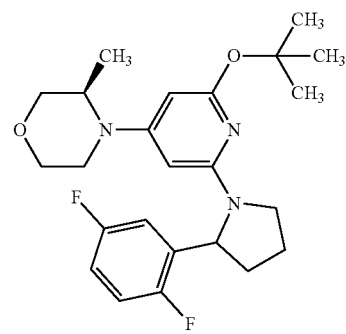 [SMILES: C[C@@H]1COCCN1c1cc(OC(C)(C)C)nc(N2CCCC2c2cc(F)ccc2F)c1]

The title compound was prepared as described in Intermediate example 9 except the mixture was stirred for 16 h, starting from (3R)-4-(2-tert-butoxy-6-chloro-4-pyridyl)-3-methyl-morpholine (700 mg, 2.46 mmol) and 2-(2,5-difluorophenyl)pyrrolidine (541 mg, 2.95 mmol), to give the product (600 mg, 57%). MS ES+ m/z 432 [M+H]+.

Example 14

(R) and (S) 6-[2-(2,5-difluorophenyl)pyrrolidin-1-yl]-4-[(3R)-3-methylmorpholin-4-yl]-1H-pyridin-2-one

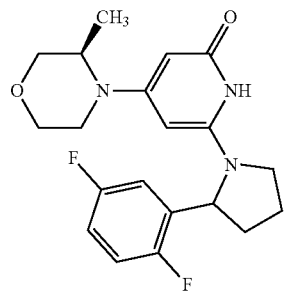 [SMILES: C[C@@H]1COCCN1c1cc(N2CCCC2c2cc(F)ccc2F)[nH]c(=O)c1]

The title compound was prepared as described in Example 10, starting from (3R)-4-[2-tert-butoxy-6-[2-(2,5-difluorophenyl)pyrrolidin-1-yl]-4-pyridyl]-3-methyl-morpholine (650 mg, 1.5 mmol) to give the product as a diastereomeric mixture (450 mg, 80%). ¹H NMR (400 MHz, CDCl₃) δ 7.06 (dt, 1H), 6.95 (br s, 1H), 6.78-6.71 (m, 1H), 5.50 (br s, 1H), 5.13-5.05 (m, 1H), 4.93 (br d, 1H), 4.00-3.91 (m, 2H), 3.75-3.46 (m, 5H), 3.25-3.06 (m, 2H), 2.54-2.42 (m, 1H), 2.17-2.00 (m, 3H), 1.26-1.19 (m, 1.5H), 0.98 (d, 1.5H). MS ES+ m/z 376 [M+H]⁺. Chiral separation by SFC gave the two isomers.

Example 14-1, First Isomer to Elute, with Unknown Absolute Configuration

¹H NMR (400 MHz, CDCl₃) δ 7.31 (br d, 1H), 7.01-6.94 (m, 2H), 6.87 (br d, 1H), 5.16 (br s, 1H), 4.79-4.72 (m, 2H), 3.92 (br d, 1H), 3.73-3.62 (m, 4H), 3.58-3.45 (m, 2H), 3.19-3.06 (m, 2H), 2.48-2.38 (m, 1H), 2.08-1.94 (m, 3H), 1.20 (br d, 3H). MS ES+m/z 358 [M+H]⁺.

Example 14-2, Second Isomer to Elute, with Unknown Absolute Configuration

¹H NMR (400 MHz, CDCl₃) δ 7.30 (br d, 1H), 7.00-6.93 (m, 2H), 6.88 (br d, 1H), 5.16 (s, 1H), 4.75 (br dd, 1H), 4.67 (s, 1H), 3.92 (br d, 1H), 3.75 (br d, 1H), 3.67 (s, 2H), 3.59-3.47 (m, 3H), 3.13-3.08 (m, 2H), 2.45 (qd, 1H), 2.10-1.94 (m, 3H), 0.98 (d, 3H). MS ES+ m/z 358 [M+H]⁺.

Intermediate Example 14

(3R)-4-[2-tert-butoxy-6-[2-[3-(trifluoromethoxy)phenyl]pyrrolidin-1-yl]-4-pyridyl]-3-methyl-morpholine

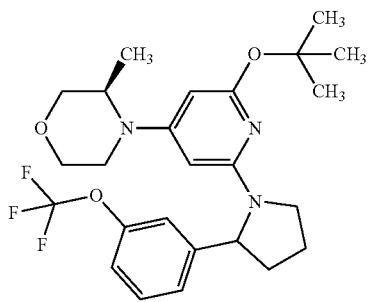 [SMILES: C[C@@H]1COCCN1c1cc(OC(C)(C)C)nc(N2CCCC2c2cccc(OC(F)(F)F)c2)c1]

The title compound was prepared as described in Intermediate example 9 except the mixture was stirred for 16 h, starting from (3R)-4-(2-tert-butoxy-6-chloro-4-pyridyl)-3-methyl-morpholine (500 mg, 1.76 mmol) and 2-[3-(trifluoromethoxy)phenyl]pyrrolidine (488 mg, 2.11 mmol), to give the product (170 mg, 20%). MS ES+ m/z 480 [M+H]⁺.

Example 15

(R) and (S) 4-[(3R)-3-methylmorpholin-4-yl]-6-[2-[3-(trifluoromethoxy)phenyl]pyrrolidin-1-yl]-1H-pyridin-2-one

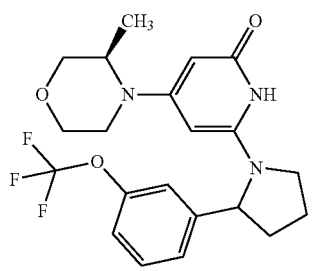 [SMILES: C[C@@H]1COCCN1c1cc(N2CCCC2c2cccc(OC(F)(F)F)c2)[nH]c(=O)c1]

The title compound was prepared as described in Example 10, starting from (3R)-4-[2-tert-butoxy-6-[2-(2,5-difluorophenyl)pyrrolidin-1-yl]-4-pyridyl]-3-methyl-morpholine (225 mg, 0.46 mmol) to give the product as a diastereomeric mixture (120 mg, 60%). ¹H NMR (400 MHz, CDCl₃) δ 7.38-7.33 (m, 1H), 7.12 (br d, 2H), 7.04 (br s, 1H), 5.14 (dd, 1H), 4.77 (ddd, 1H), 4.68-4.59 (m, 1H), 3.93-3.74 (m, 2H), 3.70-3.46 (m, 5H), 3.16-3.01 (m, 2H), 2.50-2.39 (m, 1H), 2.09-2.01 (m, 2H), 1.98-1.91 (m, 1H), 1.19 (d, 1.5H), 0.92 (d, 1.5H). MS ES+ m/z 424 [M+H]⁺. Chiral separation by SFC gave the two isomers.

Example 15-1, First Isomer to Elute, with Unknown Absolute Configuration

¹H NMR (400 MHz, CDCl₃) δ 7.38-7.34 (m, 1H), 7.12 (br d, 2H), 7.05 (s, 1H), 5.14 (d, 1H), 4.75 (dd, 1H), 4.61 (d, 1H), 3.90 (br d, 1H), 3.82-3.76 (m, 1H), 3.65 (s, 2H), 3.59-3.46 (m, 3H), 3.10-3.07 (m, 2H), 2.46 (qd, 1H), 2.09-1.91 (m, 3H), 0.92 (d, 3H). MS ES+ m/z 424 [M+H]⁺.

Example 15-2, Second Isomer to Elute, with Unknown Absolute Configuration

¹H NMR (400 MHz, CDCl₃) δ 7.40-7.34 (m, 1H), 7.13 (br t, 2H), 7.05-6.99 (m, 1H), 5.15 (s, 1H), 4.77 (br d, 1H), 4.69 (s, 1H), 3.91 (br d, 1H), 3.74-3.46 (m, 6H), 3.17-3.02 (m, 2H), 2.50-2.40 (m, 1H), 2.08-1.93 (m, 3H), 1.19 (br d, 3H). MS ES+ m/z 424 [M+H]⁺.

Intermediate Example 15

(3R)-4-[2-tert-butoxy-6-[2-[3-(trifluoromethyl)phenyl]pyrrolidin-1-yl]-4-pyridyl]-3-methyl-morpholine

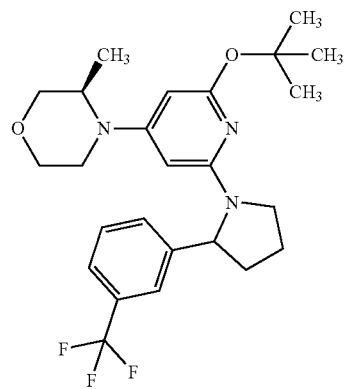 [SMILES: C[C@@H]1COCCN1c1cc(OC(C)(C)C)nc(N2CCCC2c2cccc(C(F)(F)F)c2)c1]

The title compound was prepared as described in Intermediate example 9 except the mixture was stirred for 3 h, starting from (3R)-4-(2-tert-butoxy-6-chloro-4-pyridyl)-3-methyl-morpholine (700 mg, 2.46 mmol) and 2-[3-(trifluoromethyl)phenyl]pyrrolidine (636 mg, 2.95 mmol), to give the product (800 mg, 70%). MS ES+ m/z 464 [M+H]⁺.

Example 16

(R) and (S) 4-[(3R)-3-methylmorpholin-4-yl]-6-[2-[3-(trifluoromethyl)phenyl]pyrrolidin-1-yl]-1H-pyridin-2-one

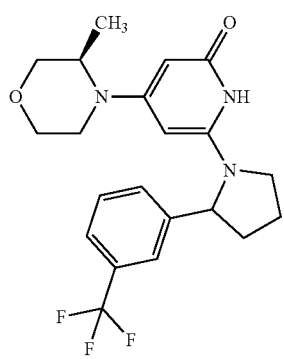 [SMILES: C[C@@H]1COCCN1c1cc(N2CCCC2c2cccc(C(F)(F)F)c2)[nH]c(=O)c1]

The title compound was prepared as described in Example 10, starting from (3R)-4-[2-tert-butoxy-6-[2-[3-(trifluoromethyl)phenyl]pyrrolidin-1-yl]-4-pyridyl]-3-methyl-morpholine (800 mg, 1.72 mmol) to give the product as a diastereomeric mixture (300 mg, 42%). $^1$H NMR (400 MHz, CDCl$_3$) δ 7.54-7.51 (m, 1H), 7.47-7.42 (m, 2H), 7.39-7.35 (m, 1H), 5.14 (dd, 1H), 4.89-4.78 (m, 1H), 4.68-4.58 (m, 1H), 3.93-3.76 (m, 2H), 3.71-3.45 (m, 5H), 3.16-3.01 (m, 2H), 2.52-2.41 (m, 1H), 2.10-2.00 (m, 2H), 1.98-1.92 (m, 1H), 1.19 (d, 1.5H), 0.88 (br d, 1.5H). MS ES+ m/z 408 [M+H]$^+$. Chiral separation by SFC gave the two isomers.

Example 16-1, First Isomer to Elute, with Unknown Absolute Configuration $^1$H NMR (400 MHz, CDCl$_3$) δ 7.55-7.51 (m, 1H), 7.49-7.44 (m, 2H), 7.37 (br d, 1H), 5.13 (s, 1H), 4.79 (br dd, 1H), 4.62 (s, 1H), 3.90 (br d, 1H), 3.80-3.74 (m, 1H), 3.65 (s, 2H), 3.58-3.46 (m, 3H), 3.09 (br d, 2H), 2.54-2.44 (m, 1H), 2.11-2.04 (m, 2H), 2.00-1.93 (m, 1H), 0.92 (d, 3H). MS ES+ m/z 408 [M+H]$^+$.

Example 16-2, Second Isomer to Elute, with Unknown Absolute Configuration $^1$H NMR (400 MHz, CDCl$_3$) δ 7.56-7.44 (m, 3H), 7.37 (br d, 1H), 5.16 (s, 1H), 4.82 (br d, 1H), 4.71 (s, 1H), 3.91 (br d, 1H), 3.71-3.47 (m, 6H), 3.17-3.03 (m, 2H), 2.50-2.43 (m, 1H), 2.09-1.98 (m, 3H), 1.20 (br d, 3H). MS ES+ m/z 408 [M+H]$^+$.

Intermediate Example 16

(3R)-4-[2-tert-butoxy-6-[2-(3-methoxyphenyl)pyrrolidin-1-yl]-4-pyridyl]-3-methyl-morpholine

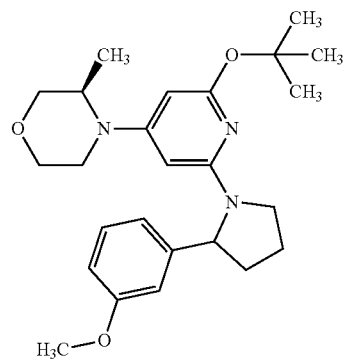 [SMILES: COc1cccc(C2CCCN2c2cc(N3CCOC[C@H]3C)cc(OC(C)(C)C)n2)c1]

The title compound was prepared as described in Intermediate example 9 except the mixture was stirred for 6 h at 110° C., starting from (3R)-4-(2-tert-butoxy-6-chloro-4-pyridyl)-3-methyl-morpholine (500 mg, 1.76 mmol) and 2-(3-methoxyphenyl)pyrrolidine (374 mg, 2.1 mmol), to give the product (550 mg, 73%). MS ES+ m/z 426 [M+H]$^+$.

Example 17

(R) and (S) 6-[2-(3-methoxyphenyl)pyrrolidin-1-yl]-4-[(3R)-3-methylmorpholin-4-yl]-1H-pyridin-2-one

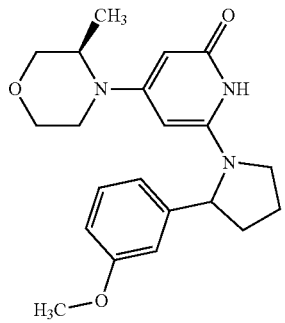 [SMILES: COc1cccc(C2CCCN2c2cc(N3CCOC[C@H]3C)cc(=O)[nH]2)c1]

The title compound was prepared as described in Example 10, starting from (3R)-4-[2-tert-butoxy-6-[2-(3-methoxyphenyl)pyrrolidin-1-yl]-4-pyridyl]-3-methylmorpholine (500 mg, 1.17 mmol) to give the product as a diastereomeric mixture (325 mg, 75%). $^1$H NMR (400 MHz, CDCl$_3$-d) δ 7.25-7.22 (m, 1H) 6.81-6.75 (m, 2H) 6.70 (s, 1H) 5.13 (dd, 1H) 4.77-4.69 (m, 2H) 3.95-3.89 (m, 1H) 3.79 (d, 3H) 3.75-3.65 (m, 4H) 3.60-3.43 (m, 3H) 3.21-3.06 (m, 2H) 2.47-2.36 (m, 1H) 2.12-1.93 (m, 3H) 1.20 (d, 1H) 1.00 (d, 1H). MS ES+ m/z 370 [M+H]$^+$. Chiral separation by SFC gave the two isomers.

Example 17-1, First Isomer to Elute, with Unknown Absolute Configuration $^1$H NMR (400 MHz, CDCl$_3$) δ 7.27 (br s, 0.5H) 7.23 (s, 0.5H) 6.81-6.75 (m, 2H) 6.70 (s, 1H) 5.13 (d, 1H) 4.77-4.71 (m, 2H) 3.92 (br dd, 1H) 3.79 (s, 3H) 3.72-3.65 (m, 4H)

3.58-3.43 (m, 2H) 3.21-3.06 (m, 2H) 2.46-2.36 (m, 1H) 2.08-1.93 (m, 3H) 1.20 (d, 3H). MS ES+ m/z 370 [M+H]⁺.

Example 17-2, Second Isomer to Elute, with Unknown Absolute Configuration

¹H NMR (400 MHz, CDCl₃) δ 7.24-7.22 (m, 1H) 6.80-6.75 (m, 2H) 6.71 (s, 1H) 5.12 (d, 1H) 4.72-4.68 (m, 2H) 3.91 (br d, 1H) 3.78 (s, 3H) 3.73 (td, 1H) 3.67 (d, 2H) 3.60-3.47 (m, 3H) 3.16-3.05 (m, 2H) 2.47-2.37 (m, 1H) 2.10-1.93 (m, 3H) 0.99 (d, 3H). MS ES+ m/z 370 [M+H]⁺.

Intermediate Example 17

(3R)-4-[2-tert-butoxy-6-(2-phenylpyrrolidin-1-yl)-4-pyridyl]-3-methyl-morpholine

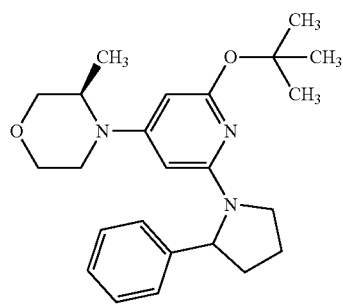 [SMILES: C[C@@H]1COCCN1c1cc(OC(C)(C)C)nc(N2CCCC2c2ccccc2)c1]

The title compound was prepared as described in Intermediate example 9 except the mixture was stirred for 6 h at 110° C., starting from (3R)-4-(2-tert-butoxy-6-chloro-4-pyridyl)-3-methyl-morpholine (400 mg, 1.4 mmol) and 2-phenylpyrrolidine (384 mg, 2.53 mmol), to give the product (325 mg, 58%). MS ES+ m/z 396 [M+H]⁺.

Example 18

(R) and (S) 4-[(3R)-3-methylmorpholin-4-yl]-6-(2-phenylpyrrolidin-1-yl)-1H-pyridin-2-one

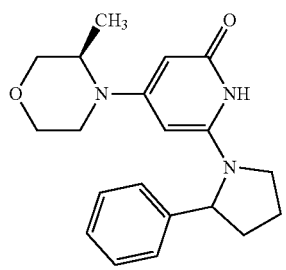 [SMILES: C[C@@H]1COCCN1c1cc(N2CCCC2c2ccccc2)[nH]c(=O)c1]

The title compound was prepared as described in Example 10, starting from (3R)-4-[2-tert-butoxy-6-(2-phenylpyrrolidin-1-yl)-4-pyridyl]-3-methyl-morpholine (320 mg, 0.86 mmol) to give the product as a diastereomeric mixture (230 mg, 55%). ¹H NMR (400 MHz, CDCl₃) δ ppm 7.32 (br dd, 3H) 7.17 (br d, 2H) 5.13 (dd, 1H) 4.79-4.67 (m, 2H) 3.94-3.88 (m, 1H) 3.72-3.45 (m, 6H) 3.19-3.05 (m, 2H) 2.48-2.37 (m, 1H) 2.11-1.94 (m, 3H) 1.25 (s, 1H) 1.20 (br d, 1H) 0.97 (d, 1H). MS ES+ m/z 340 [M+H]⁺. Chiral separation by SFC gave the two isomers.

Example 18-1, First Isomer to Elute, with Unknown Absolute Configuration

¹H NMR (400 MHz, CDCl₃) δ 7.36-7.28 (m, 3H) 7.17 (br d, 2H) 5.13 (d, 1H) 4.79-4.73 (m, 2H) 3.91 (br dd, 1H) 3.71-3.45 (m, 6H) 3.19-3.04 (m, 2H) 2.47-2.37 (m, 1H) 2.08-1.93 (m, 3H) 1.27 (dd, 1H) 1.20 (d, 2H). MS ES+ m/z 340 [M+H]⁺.

Example 18-2, Second Isomer to Elute, with Unknown Absolute Configuration

¹H NMR (400 MHz, CDCl₃) δ 7.34-7.29 (m, 2H) 7.25-7.15 (m, 3H) 5.12 (d, 1H) 4.76-4.66 (m, 2H) 3.90 (br d, 1H) 3.75 (td, 1H) 3.65 (s, 2H) 3.57-3.46 (m, 3H) 3.13-3.07 (m, 2H) 2.49-2.39 (m, 1H) 2.10-1.93 (m, 3H) 0.95 (d, 3H). MS ES+ m/z 340 [M+H]⁺.

Intermediate Example 18

(3R)-4-[2-tert-butoxy-6-[2-(1-methylpyrazol-4-yl)pyrrolidin-1-yl]-4-pyridyl]-3-methyl-morpholine

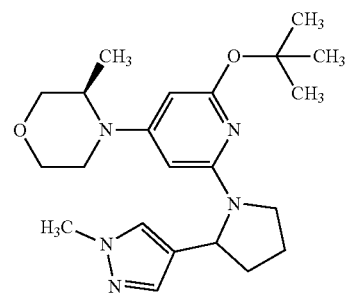 [SMILES: C[C@@H]1COCCN1c1cc(OC(C)(C)C)nc(N2CCCC2c2cnn(C)c2)c1]

The title compound was prepared as described in Intermediate example 9 except the mixture was stirred for 16 h at 90° C., starting from (3R)-4-(2-tert-butoxy-6-chloro-4-pyridyl)-3-methyl-morpholine (1 g, 3.42 mmol) and 1-methyl-4-pyrrolidin-2-yl-pyrazole (638 mg, 4.2 mmol), to give the product (800 mg, 57%). MS ES+ m/z 400 [M+H]⁺.

Example 19

(R) and (S) 4-[(3R)-3-methylmorpholin-4-yl]-6-[2-(1-methylpyrazol-4-yl)pyrrolidin-1-yl]-1H-pyridin-2-one

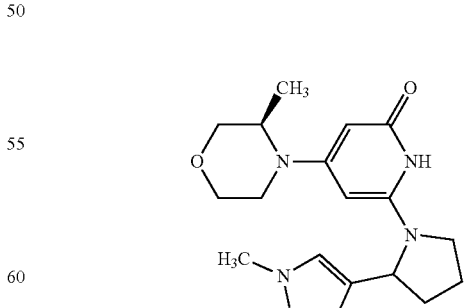

The title compound was prepared as described in Example 10, starting from (3R)-4-[2-tert-butoxy-6-[2-(1-methylpyrazol-4-yl)pyrrolidin-1-yl]-4-pyridyl]-3-methyl-morpholine (800 mg, 1.99 mmol) to give the product as a diastereomeric mixture (500 mg, 73%). ¹H NMR (400 MHz, CDCl₃) δ 7.32 (s, 1H), 7.19 (d, 1H), 5.15 (s, 1H), 4.80 (dd, 2H), 3.94 (br d, 1H), 3.84 (d, 3H), 3.71 (s, 3H), 3.61-3.51 (m, 2H), 3.41-3.32 (m, 1H), 3.25-3.11 (m, 2H), 2.36-2.24 (m, 1H), 2.10-2.02 (m, 2H), 1.97-1.91 (m, 1H), 1.22 (d, 1.5H), 1.14 (br d, 1.5H). MS ES+ m/z 344 [M+H]⁺. Chiral separation by SFC gave the two isomers.

Example 19-1, First Isomer to Elute, with Unknown Absolute Configuration

¹H NMR (400 MHz, CDCl₃) δ 7.32 (s, 1H), 7.19 (s, 1H), 5.15 (d, 1H), 4.84-4.80 (m, 2H), 3.94 (br dd, 1H), 3.84 (s, 3H), 3.74-3.66 (m, 3H), 3.61-3.52 (m, 2H), 3.36 (q, 1H), 3.25-3.11 (m, 2H), 2.34-2.24 (m, 1H), 2.08-2.02 (m, 2H), 1.96-1.90 (m, 1H), 1.21 (d, 3H). MS ES+ m/z 344 [M+H]⁺.

Example 19-2, Second Isomer to Elute, with Unknown Absolute Configuration

¹H NMR (400 MHz, CDCl₃) δ 7.32 (s, 1H), 7.19 (s, 1H), 5.15 (d, 1H), 4.83-4.79 (m, 2H), 3.96-3.91 (m, 1H), 3.83 (s, 3H), 3.73-3.68 (m, 3H), 3.63-3.51 (m, 2H), 3.38 (q, 1H), 3.22-3.11 (m, 2H), 2.35-2.26 (m, 1H), 2.10-2.01 (m, 2H), 1.97-1.91 (m, 1H), 1.13 (d, 3H). MS ES+ m/z 344 [M+H]⁺.

Intermediate Example 19

(3R)-4-[2-tert-butoxy-6-[2-(1,5-dimethylpyrazol-3-yl)pyrrolidin-1-yl]-4-pyridyl]-3-methyl-morpholine

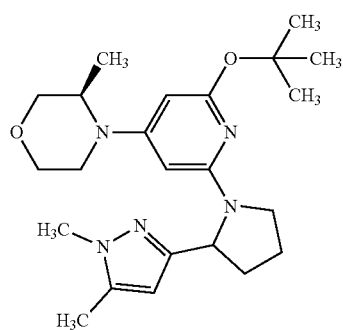 [SMILES: Cc1cc(C2CCCN2c2cc(N3CCOC[C@H]3C)cc(OC(C)(C)C)n2)nn1C]

The title compound was prepared as described in Intermediate example 9 except the mixture was stirred for 2 h at 100° C., starting from (3R)-4-(2-tert-butoxy-6-chloro-4-pyridyl)-3-methyl-morpholine (500 mg, 1.76 mmol) and 1,5-dimethyl-3-pyrrolidin-2-yl-pyrazole (342 mg, 2.1 mmol), to give the product (400 mg, 55%). MS ES+ m/z 414 [M+H]⁺.

Example 20

(R) and (S) 6-[2-(1,5-dimethylpyrazol-3-yl)pyrrolidin-1-yl]-4-[(3R)-3-methylmorpholin-4-yl]-1H-pyridin-2-one

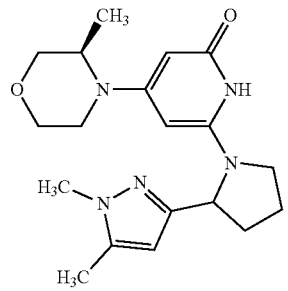 [SMILES: Cc1cc(C2CCCN2c2cc(N3CCOC[C@H]3C)cc(=O)[nH]2)nn1C]

The title compound was prepared as described in Example 10, starting from (3R)-4-[2-tert-butoxy-6-[2-(1,5-dimethylpyrazol-3-yl)pyrrolidin-1-yl]-4-pyridyl]-3-methyl-morpholine (400 mg, 0.96 mmol) to give the product as a diastereomeric mixture (200 mg, 58%). ¹H NMR (400 MHz, CDCl₃) δ 5.82 (d, 1H) 5.15 (br s, 1H) 4.87 (br s, 1H) 4.77 (br d, 1H) 3.94 (br dd, 1H) 3.77-3.70 (m, 6H) 3.59-3.51 (m, 2H) 3.35 (br s, 1H) 3.26-3.14 (m, 2H) 2.35-2.29 (m, 1H) 2.22-2.09 (m, 6H) 1.20 (d, 1.5H) 1.14 (d, 1.5H). MS ES+ m/z 358 [M+H]⁺. Chiral separation by SFC gave the two isomers.

Example 20-1, First Isomer to Elute, with Unknown Absolute Configuration

¹H NMR (400 MHz, CDCl₃) δ 5.83 (s, 1H) 5.15 (d, 1H) 4.87 (d, 1H) 4.78-4.75 (m, 1H) 3.94 (br dd, 1H) 3.77-3.68 (m, 6H) 3.60-3.49 (m, 2H) 3.37-3.30 (m, 1H) 3.26-3.11 (m, 2H) 2.34-2.29 (m, 1H) 2.21 (s, 3H) 2.17-2.05 (m, 3H) 1.20 (d, 3H). MS ES+ m/z 358 [M+H]⁺.

Example 20-2, Second Isomer to Elute, with Unknown Absolute Configuration

¹H NMR (400 MHz, CDCl₃) δ 5.81 (s, 1H) 5.14 (d, 1H) 4.87 (d, 1H) 4.76 (dd, 1H) 3.94 (dd, 1H) 3.77-3.68 (m, 6H) 3.59-3.51 (m, 2H) 3.39-3.33 (m, 1H) 3.25-3.11 (m, 2H) 2.37-2.29 (m, 1H) 2.22-2.04 (m, 6H) 1.14 (d, 3H). MS ES+ m/z 358 [M+H]⁺.

Intermediate Example 20

(3R)-4-[2-tert-butoxy-6-[2-(1-ethylpyrazol-3-yl)pyrrolidin-1-yl]-4-pyridyl]-3-methyl-morpholine

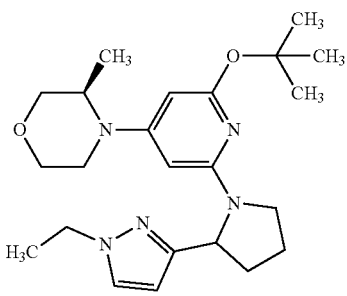 [SMILES: CCn1ccc(C2CCCN2c2cc(N3CCOC[C@H]3C)cc(OC(C)(C)C)n2)n1]

The title compound was prepared as described in Intermediate example 9 except the mixture was stirred for 10 h, starting from (3R)-4-(2-tert-butoxy-6-chloro-4-pyridyl)-3-methyl-morpholine (500 mg, 1.76 mmol) and 1-ethyl-3-pyrrolidin-2-yl-pyrazole (348 mg, 2.11 mmol), to give the product (380 mg, 52%). MS ES+ m/z 414 [M+H]+.

Example 21

(R) and (S) 6-[2-(1-ethylpyrazol-3-yl)pyrrolidin-1-yl]-4-[(3R)-3-methylmorpholin-4-yl]-1H-pyridin-2-one

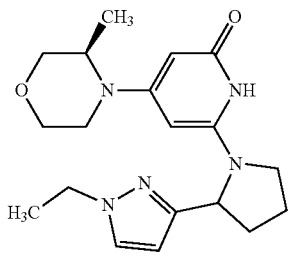 [SMILES: CCn1ccc(C2CCCN2c2cc(N3CCOC[C@H]3C)cc(=O)[nH]2)n1]

The title compound was prepared as described in Example 10, starting from (3R)-4-[2-tert-butoxy-6-[2-(1-ethylpyrazol-3-yl)pyrrolidin-1-yl]-4-pyridyl]-3-methyl-morpholine (370 mg, 0.89 mmol) to give the product as a diastereomeric mixture (260 mg, 81%). ¹H NMR (400 MHz, CDCl₃) δ 7.31-7.29 (m, 1H) 6.03 (d, 1H) 5.15 (br d, 1H) 4.85 (br d, 2H) 4.16-4.12 (m, 2H) 3.93 (br dd, 1H) 3.76-3.70 (m, 3H) 3.55-3.51 (m, 2H) 3.35 (br d, 1H) 3.25-3.15 (m, 2H) 2.19 (d, 1H) 2.14-1.88 (m, 3H) 1.50-1.47 (m, 3H) 1.20 (d, 3H). MS ES+ m/z 358 [M+H]+. Chiral separation by SFC gave the two isomers.

Example 21-1, First Isomer to Elute, with Unknown Absolute Configuration

¹H NMR (400 MHz, CDCl₃) δ 7.30 (s, 1H) 6.03 (d, 1H) 5.14 (s, 1H) 4.85 (br s, 2H) 4.13 (q, 2H) 3.93 (br d, 1H) 3.75-3.69 (m, 3H) 3.58-3.52 (m, 2H) 3.41-3.34 (m, 1H) 3.24-3.14 (m, 2H) 2.39-2.32 (m, 1H) 2.17 (br d, 3H) 1.48 (t, 3H) 1.13 (br d, 3H). MS ES+ m/z 358 [M+H]+.

Example 21-2, Second Isomer to Elute, with Unknown Absolute Configuration

¹H NMR (400 MHz, CDCl₃) δ 7.31 (s, 1H) 6.05 (s, 1H) 5.16 (s, 1H) 4.87-4.83 (m, 2H) 4.14 (q, 2H) 3.93 (br d, 1H) 3.76-3.69 (m, 3H) 3.54 (br d, 2H) 3.35 (br d, 1H) 3.25-3.13 (m, 2H) 2.37-2.31 (m, 1H) 2.20 (br d, 3H) 1.51-1.47 (m, 3H) 1.20 (br d, 3H). MS ES+ m/z 358 [M+H]+.

Intermediate Example 21

(3R)-4-[2-tert-butoxy-6-[2-(5-methyl-2-furyl)pyrrolidin-1-yl]-4-pyridyl]-3-methyl-morpholine

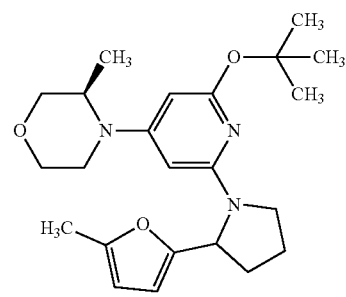 [SMILES: Cc1ccc(C2CCCN2c2cc(N3CCOC[C@H]3C)cc(OC(C)(C)C)n2)o1]

The title compound was prepared as described in Intermediate example 9 except the mixture was stirred for 16 h, starting from (3R)-4-(2-tert-butoxy-6-chloro-4-pyridyl)-3-methyl-morpholine (600 mg, 2.11 mmol) and 2-(5-methyl-2-furyl)pyrrolidine (383 mg, 2.53 mmol), to give the product (420 mg, 50%). MS ES+ m/z 400 [M+H]+.

Example 22

(R) and (S) 6-[2-(5-methyl-2-furyl)pyrrolidin-1-yl]-4-[(3R)-3-methylmorpholin-4-yl]-1H-pyridin-2-one

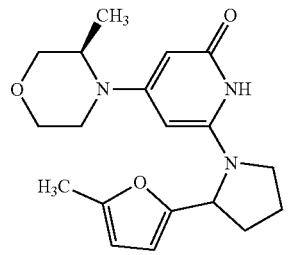 [SMILES: Cc1ccc(C2CCCN2c2cc(N3CCOC[C@H]3C)cc(=O)[nH]2)o1]

The title compound was prepared as described in Example 10, starting from (3R)-4-[2-tert-butoxy-6-[2-(5-methyl-2-furyl)pyrrolidin-1-yl]-4-pyridyl]-3-methyl-morpholine (420 mg, 1.05 mmol) to give the product as a diastereomeric mixture (250 mg, 69%). ¹H NMR (400 MHz, CDCl₃) δ 6.06-6.03 (m, 1H), 5.86 (br s, 1H), 5.17-5.15 (m, 1H), 4.87 (d, 1H), 4.75 (br d, 1H), 3.95 (br dd, 1H), 3.78-3.70 (m, 3H), 3.61-3.53 (m, 2H), 3.41-3.33 (m, 1H), 3.24-3.12 (m, 2H), 2.27-2.15 (m, 6H), 2.08-2.01 (m, 1H), 1.24-1.14 (m, 3H). MS ES+ m/z 344 [M+H]+. Chiral separation by SFC gave the two isomers.

Example 22-1, First Isomer to Elute, with Unknown Absolute Configuration

¹H NMR (400 MHz, CDCl₃) δ 6.04 (d, 1H), 5.86 (br s, 1H), 5.16 (s, 1H), 4.86 (s, 1H), 4.74 (br d, 1H), 3.95 (br d, 1H), 3.72 (s, 3H), 3.60-3.52 (m, 2H), 3.39-3.34 (m, 1H), 3.25-3.16 (m, 2H), 2.27-2.16 (m, 6H), 2.06 (br s, 1H), 1.16 (br d, 3H). MS ES+ m/z 344 [M+H]+.

Example 22-2, Second Isomer to Elute, with Unknown Absolute Configuration

¹H NMR (400 MHz, CDCl₃) δ 6.05 (d, 1H), 5.87 (br s, 1H), 5.17 (s, 1H), 4.87 (s, 1H), 4.74 (br d, 1H), 3.95 (br d,

1H), 3.78-3.71 (m, 3H), 3.61-3.51 (m, 2H), 3.37-3.18 (m, 3H), 2.27-2.16 (m, 6H), 2.06 (br s, 1H), 1.22 (d, 3H). MS ES+ m/z 344 [M+H]+.

Intermediate Example 22

3-[1-[6-tert-butoxy-4-[(3R)-3-methylmorpholin-4-yl]-2-pyridyl]pyrrolidin-2-yl]-N,N-dimethyl-aniline

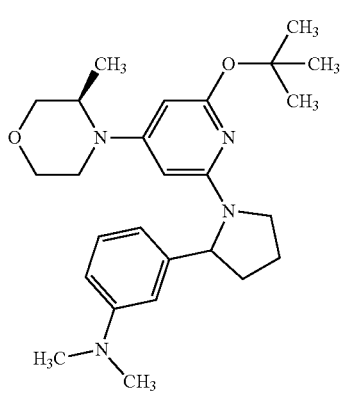 [SMILES: C[C@@H]1COCCN1c1cc(OC(C)(C)C)nc(N2CCCC2c2cccc(N(C)C)c2)c1]

The title compound was prepared as described in Intermediate example 9 except the mixture was stirred for 2 h at 70° C., starting from (3R)-4-(2-tert-butoxy-6-chloro-4-pyridyl)-3-methyl-morpholine (100 mg, 0.35 mmol) and N,N-dimethyl-3-pyrrolidin-2-yl-aniline (100 mg, 0.53 mmol), to give the product (136 mg, 88%). MS ES+ m/z 439 [M+H]+.

Example 23

(R) and (S) 6-[2-[3-(dimethylamino)phenyl]pyrrolidin-1-yl]-4-[(3R)-3-methylmorpholin-4-yl]-1H-pyridin-2-one

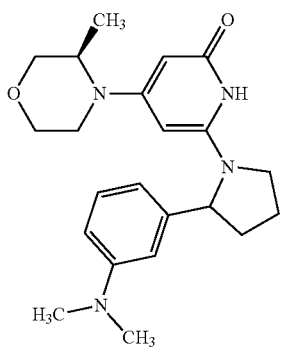 [SMILES: C[C@@H]1COCCN1c1cc(N2CCCC2c2cccc(N(C)C)c2)[nH]c(=O)c1]

The title compound was prepared as described in Example 10, starting from 3-[1-[6-tert-butoxy-4-[(3R)-3-methylmorpholin-4-yl]-2-pyridyl]pyrrolidin-2-yl]-N,N-dimethyl-aniline (136 mg, 0.31 mmol) to give the product as a diastereomeric mixture (33 mg, 28%). 1H NMR (500 MHz, DMSO-d6) δ 7.14-7.04 (m, 1H), 6.63-6.53 (m, 2H), 6.50-6.39 (m, 1H), 4.94-4.74 (m, 3H), 3.86-3.79 (m, 1H), 3.75-3.69 (m, 1H), 3.62 (br d, 2H), 3.56-3.42 (m, 4H), 3.18 (br d, 1H), 3.08 (br d, 1H), 2.88-2.85 (m, 6H), 2.39-2.25 (m, 1H), 1.97-1.87 (m, 2H), 1.80 (br d, 1H), 1.09-1.00 (m, 1.5H), 0.77 (br d, 1.5H). MS ES+ m/z 383 [M+H]+.

Intermediate Example 23

(3R)-4-[2-tert-butoxy-6-(3-methylmorpholin-4-yl)-4-pyridyl]-3-methyl-morpholine

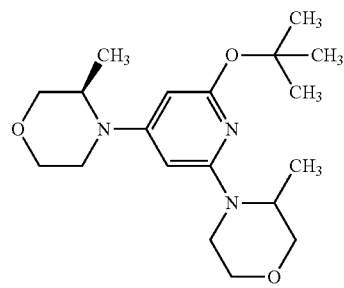 [SMILES: CC1COCCN1c1cc(N2CCOC[C@H]2C)cc(OC(C)(C)C)n1]

The title compound was prepared as described in Intermediate example 9 except the mixture was stirred for 6 h at 110° C., starting from (3R)-4-(2-tert-butoxy-6-chloro-4-pyridyl)-3-methyl-morpholine (500 mg, 1.76 mmol) and 3-methylmorpholine (213 mg, 2.1 mmol), to give the product (470 mg, 76%). MS ES+ m/z 350 [M+H]+.

Example 24

(R) and (S) 4-[(3R)-3-methylmorpholin-4-yl]-6-(3-methylmorpholin-4-yl)-1H-pyridin-2-one

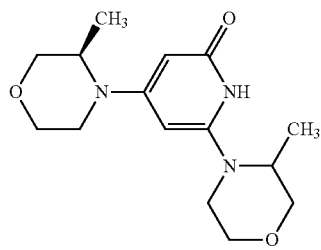 [SMILES: CC1COCCN1c1cc(N2CCOC[C@H]2C)cc(=O)[nH]1]

The title compound was prepared as described in Example 10, starting from (3R)-4-[2-tert-butoxy-6-(3-methylmorpholin-4-yl)-4-pyridyl]-3-methyl-morpholine (500 mg, 1.42 mmol) to give the product as a diastereomeric mixture (230 mg, 55%). 1H NMR (400 MHz, CDCl3) δ 5.30 (s, 1H) 5.08 (d, 1H) 4.00-3.55 (m, 10H) 3.32-3.16 (m, 3H) 3.08 (br t, 1H) 1.26-1.17 (m, 6H). MS ES+ m/z 294 [M+H]+. Chiral separation by SFC gave the two isomers.

Example 24-1, First Isomer to Elute, with Unknown Absolute Configuration

1H NMR (400 MHz, CDCl3) δ 5.29 (d, 1H), 5.07 (d, 1H), 3.95 (br d, 3H), 3.85-3.69 (m, 7H), 3.25-3.19 (m, 3H), 3.05 (br d, 1H), 1.22-1.17 (m, 6H). MS ES+ m/z 294 [M+H]+.

Example 24-2, Second Isomer to Elute, with Unknown Absolute Configuration

1H NMR (400 MHz, CDCl3) δ 5.28 (br s, 1H), 5.03 (br s, 1H), 3.99-3.72 (m, 10H), 3.33-3.18 (m, 4H), 1.25-1.18 (m, 6H). MS ES+ m/z 294 [M+H]+.

Intermediate Example 24

(3R)-4-[2-tert-butoxy-6-[2-(trifluoromethyl)-1-piperidyl]-4-pyridyl]-3-methyl-morpholine

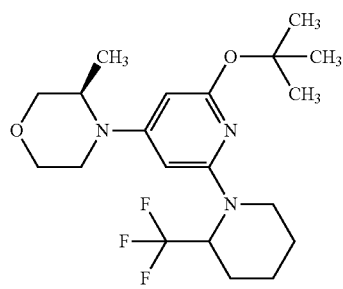 [SMILES: C[C@@H]1COCCN1c1cc(OC(C)(C)C)nc(N2CCCCC2C(F)(F)F)c1]

The title compound was prepared as described in Intermediate example 9, starting from (3R)-4-(2-tert-butoxy-6-chloro-4-pyridyl)-3-methyl-morpholine (500 mg, 1.76 mmol) and 2-(trifluoromethyl)piperidine (323 mg, 2.11 mmol), to give the product (575 mg, 81%). MS ES+ m/z 402 [M+H]+.

Example 25

(R) and (S) 4-[(3R)-3-methylmorpholin-4-yl]-6-[2-(trifluoromethyl)-1-piperidyl]-1H-pyridin-2-one

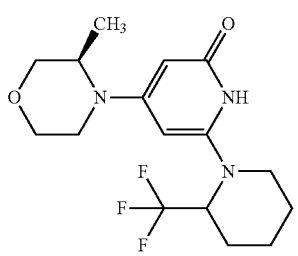 [SMILES: C[C@@H]1COCCN1c1cc(N2CCCCC2C(F)(F)F)[nH]c(=O)c1]

The title compound was prepared as described in Example 10, starting from (3R)-4-[2-tert-butoxy-6-[2-(trifluoromethyl)-1-piperidyl]-4-pyridyl]-3-methyl-morpholine (500 mg, 1.24 mmol) to give the product as a diastereomeric mixture (230 mg, 53%). 1H NMR (300 MHz, DMSO-d6) δ 9.71 (br s, 1H), 5.59-5.55 (m, 1H), 5.32 (br s, 2H), 3.89 (br s, 3H), 3.69-3.65 (m, 2H), 3.61 (br s, 2H), 3.34-3.32 (m, 2H), 1.91 (br s, 1H), 1.65 (br s, 5H), 1.06 (br s, 3H). MS ES+ m/z 346 [M+H]+. Chiral separation by SFC gave the two isomers.

Example 25-1, First Isomer to Elute, with Unknown Absolute Configuration

1H NMR (400 MHz, CDCl3) δ 5.29 (d, 1H), 5.20 (d, 1H), 4.78-4.74 (m, 1H), 3.99-3.95 (m, 1H), 3.83-3.75 (m, 3H), 3.63-3.58 (m, 1H), 3.39 (br d, 1H), 3.24-3.18 (m, 3H), 2.13-2.03 (m, 2H), 1.80-1.69 (m, 4H), 1.21 (d, 3H). MS ES+ m/z 346 [M+H]+.

Example 25-2, Second Isomer to Elute, with Unknown Absolute Configuration

1H NMR (400 MHz, CDCl3) δ 5.30 (d, 1H), 5.20 (d, 1H), 4.75-4.70 (m, 1H), 3.97 (br dd, 1H), 3.81-3.74 (m, 3H), 3.64-3.59 (m, 1H), 3.39 (br d, 1H), 3.31-3.20 (m, 3H), 2.11-1.99 (m, 2H), 1.80-1.69 (m, 4H), 1.23 (d, 3H). MS ES+ m/z 346 [M+H]+.

Intermediate Example 25

4-[6-tert-butoxy-4-[(3R)-3-methylmorpholin-4-yl]-2-pyridyl]-3-phenyl-morpholine

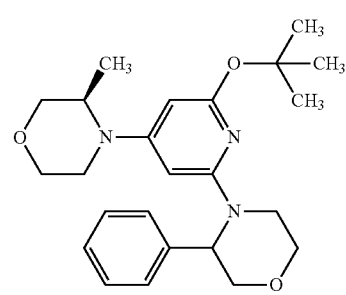 [SMILES: C[C@@H]1COCCN1c1cc(OC(C)(C)C)nc(N2CCOCC2c2ccccc2)c1]

The title compound was prepared as described in Intermediate example 9, starting from (3R)-4-(2-tert-butoxy-6-chloro-4-pyridyl)-3-methyl-morpholine (400 mg, 1.4 mmol) and 3-phenylmorpholine (275 mg, 1.69 mmol), to give the product (360 mg, 62%). MS ES+ m/z 412 [M+H]+.

Example 26

(R) and (S) 4-[(3R)-3-methylmorpholin-4-yl]-6-(3-phenylmorpholin-4-yl)-1H-pyridin-2-one

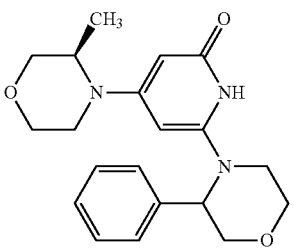 [SMILES: C[C@@H]1COCCN1c1cc(N2CCOCC2c2ccccc2)[nH]c(=O)c1]

The title compound was prepared as described in Example 10, starting from 4-[6-tert-butoxy-4-[(3R)-3-methylmorpholin-4-yl]-2-pyridyl]-3-phenyl-morpholine (350 mg, 0.85 mmol) to give the product as a diastereomeric mixture (100 mg, 33%). 1H NMR (400 MHz, CDCl3) δ 7.36-7.27 (m, 3H), 7.25-7.19 (m, 2H), 5.35-5.21 (m, 1H), 5.08-4.98 (m, 1H), 4.49-4.43 (m, 0.5H), 4.33-4.27 (m, 0.5H), 4.01-3.82 (m, 4H), 3.74-3.58 (m, 3H), 3.57-3.38 (m, 3H), 3.15-2.93 (m, 3H), 1.17-1.06 (m, 1.5H), 0.78-0.63 (m, 1.5H). MS ES+ m/z 356 [M+H]+. Chiral separation by SFC gave the two isomers.

Example 26-1, First Isomer to Elute, with Unknown Absolute Configuration

1H NMR (400 MHz, CDCl3) δ 7.36-7.28 (m, 3H), 7.25-7.19 (m, 2H), 5.26 (br s, 1H), 5.02 (br s, 1H), 4.35-4.26 (m, 1H), 4.00-3.87 (m, 4H), 3.72-3.62 (m, 4H), 3.52-3.42 (m, 2H), 3.00 (br s, 3H), 0.76-0.66 (m, 3H). MS ES+ m/z 356 [M+H]+.

Example 26-2, Second Isomer to Elute, with Unknown Absolute Configuration $^1$H NMR (400 MHz, CDCl$_3$) δ 7.40-7.27 (m, 3H), 7.23 (br s, 2H), 5.35-5.21 (m, 1H), 5.09-4.90 (m, 1H), 4.57-4.36 (m, 1H), 4.11-3.73 (m, 5H), 3.71-3.29 (m, 4H), 3.71-3.29 (m, 1H), 3.20-2.90 (m, 3H), 1.13 (br d, 3H). MS ES+ m/z 356 [M+H]$^+$.

Intermediate Example 26

4-[6-tert-butoxy-4-[(3R)-3-methylmorpholin-4-yl]-2-pyridyl]-1,4-thiazinane 1-oxide

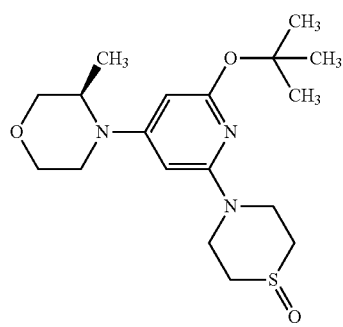 [SMILES: C[C@@H]1COCCN1c1cc(OC(C)(C)C)nc(N2CCS(=O)CC2)c1]

The title compound was prepared as described in Intermediate example 9, except the mixture was stirred overnight at 70° C., starting from (3R)-4-(2-tert-butoxy-6-chloro-4-pyridyl)-3-methyl-morpholine (100 mg, 0.35 mmol) and 1,4-thiazinane 1-oxide (67 mg, 0.56 mmol), to give the product (70 mg, 54%). MS ES+ m/z 368 [M+H]$^+$.

Example 27

4-[(3R)-3-methylmorpholin-4-yl]-6-(1-oxo-1,4-thiazinan-4-yl)-1H-pyridin-2-one

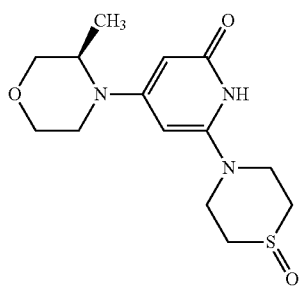 [SMILES: C[C@@H]1COCCN1c1cc(N2CCS(=O)CC2)[nH]c(=O)c1]

The title compound was prepared as described in Example 10, starting from 4-[6-tert-butoxy-4-[(3R)-3-methylmorpholin-4-yl]-2-pyridyl]-1,4-thiazinane 1-oxide (70 mg, 0.19 mmol) to give the product (14 mg, 24%). 1H NMR (500 MHz, DMSO-d$_6$) δ 5.61 (br s, 1H), 5.27 (s, 1H), 3.95-3.84 (m, 4H), 3.82-3.73 (m, 2H), 3.71-3.64 (m, 1H), 3.64-3.57 (m, 1H), 3.52-3.42 (m, 1H), 2.99 (td, 1H), 2.92-2.81 (m, 2H), 2.67-2.59 (m, 2H), 2.04-2.11 (m, 2H), 1.07 (d, 3H). MS ES+ m/z 312 [M+H]$^+$.

Intermediate Example 27

4-[6-tert-butoxy-4-[(3R)-3-methylmorpholin-4-yl]-2-pyridyl]-1,4-thiazinane 1,1-dioxide

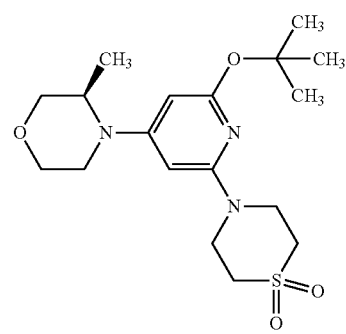 [SMILES: C[C@@H]1COCCN1c1cc(OC(C)(C)C)nc(N2CCS(=O)(=O)CC2)c1]

The title compound was prepared as described in Intermediate example 9, except the mixture was stirred overnight at 70° C., starting from (3R)-4-(2-tert-butoxy-6-chloro-4-pyridyl)-3-methyl-morpholine (100 mg, 0.35 mmol) and 1,4-thiazinane 1,1-dioxide (71 mg, 0.53 mmol), to give the product (86 mg, 64%). MS ES+ m/z 384 [M+H]$^+$.

Example 28

6-(1,1-dioxo-1,4-thiazinan-4-yl)-4-[(3R)-3-methylmorpholin-4-yl]-1H-pyridin-2-one

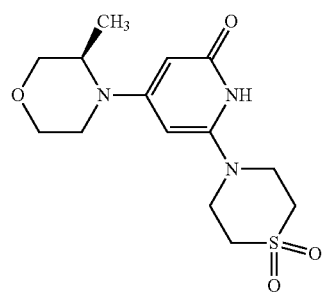 [SMILES: C[C@@H]1COCCN1c1cc(N2CCS(=O)(=O)CC2)[nH]c(=O)c1]

The title compound was prepared as described in Example 10, starting from 4-[6-tert-butoxy-4-[(3R)-3-methylmorpholin-4-yl]-2-pyridyl]-1,4-thiazinane 1,1-dioxide (86 mg, 0.22 mmol) to give the product (38 mg, 52%). 1H NMR (500 MHz, DMSO-d$_6$) δ 5.72 (br s, 1H), 5.37 (br s, 1H), 3.96-3.86 (m, 6H), 3.72-3.65 (m, 1H), 3.63-3.57 (m, 1H), 3.50-3.43 (m, 1H), 3.38 (m, 2H), 3.18 (br d, 1H), 3.09-3.05 (m, 3H), 3.03-2.94 (m, 1H), 1.07 (d, 3H). MS ES+ m/z 328 [M+H]$^+$.

Intermediate Example 28

1-[4-[6-tert-butoxy-4-[(3R)-3-methylmorpholin-4-yl]-2-pyridyl]piperazin-1-yl]ethanone

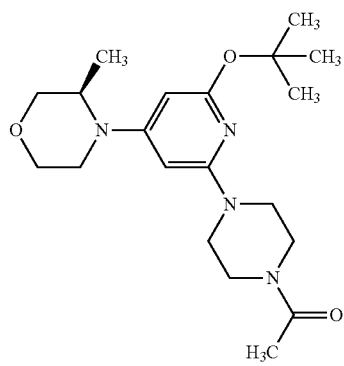 [SMILES: CC(=O)N1CCN(c2cc(N3CCOC[C@H]3C)cc(OC(C)(C)C)n2)CC1]

The title compound was prepared as described in Intermediate example 9, except the mixture was stirred for 2 h at 70° C., starting from (3R)-4-(2-tert-butoxy-6-chloro-4-pyridyl)-3-methyl-morpholine (100 mg, 0.35 mmol) and 1-piperazin-1-ylethanone (67 mg, 0.562 mmol), to give the product (67 mg, 48%). MS ES+ m/z 378 [M+H]+.

Example 29

6-(4-acetylpiperazin-1-yl)-4-[(3R)-3-methylmorpholin-4-yl]-1H-pyridin-2-one

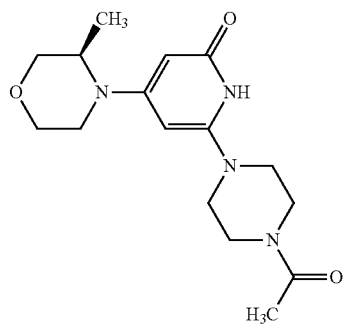 [SMILES: CC(=O)N1CCN(c2cc(N3CCOC[C@H]3C)cc(=O)[nH]2)CC1]

The title compound was prepared as described in Example 10, starting from 1-[4-[6-tert-butoxy-4-[(3R)-3-methylmorpholin-4-yl]-2-pyridyl]piperazin-1-yl]ethanone (67 mg, 0.18 mmol) to give the product (31 mg, 54%). $^1$H NMR (500 MHz, DMSO-$d_6$) δ 5.42 (br s, 1H), 5.20 (br s, 1H), 3.97-3.83 (m, 2H), 3.76-3.63 (m, 1H), 3.63-3.54 (m, 1H), 3.54-3.39 (m, 5H), 3.32-3.28 (m, 2H), 3.27-3.16 (m, 3H), 2.99 (td, 1H), 2.03 (s, 3H), 1.07 (d, 3H). MS ES+ m/z 321 [M+H]+.

Intermediate Example 29

(3R)-4-[2-tert-butoxy-6-[(2R)-2-phenyl-1-piperidyl]-4-pyridyl]-3-methyl-morpholine

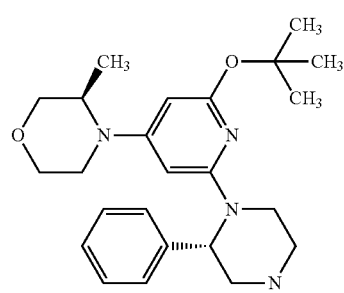 [SMILES: C[C@@H]1COCCN1c1cc(OC(C)(C)C)nc(N2CCNC[C@@H]2c2ccccc2)c1]

The title compound was prepared as described in Intermediate example 9, except the mixture was stirred for 2 h at 70° C., starting from (3R)-4-(2-tert-butoxy-6-chloro-4-pyridyl)-3-methyl-morpholine (100 mg, 0.35 mmol) and (2R)-2-phenylpiperidine (85 mg, 0.53 mmol), to give the product (137 mg, 91%). MS ES+ m/z 410 [M+H]+.

Example 30

4-[(3R)-3-methylmorpholin-4-yl]-6-[(2R)-2-phenyl-1-piperidyl]-1H-pyridin-2-one

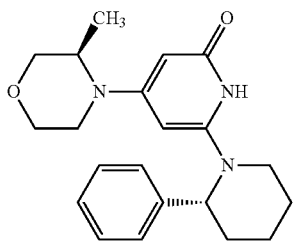 [SMILES: C[C@@H]1COCCN1c1cc(N2CCCC[C@@H]2c2ccccc2)[nH]c(=O)c1]

The title compound was prepared as described in Example 10, starting from (3R)-4-[2-tert-butoxy-6-[(2R)-2-phenyl-1-piperidyl]-4-pyridyl]-3-methyl-morpholine (137 mg, 0.33 mmol) to give the product (30 mg, 25%). $^1$H NMR (500 MHz, DMSO) δ 10.07 (br s, 1H), 7.39-7.09 (m, 5H), 5.42-5.27 (m, 1H), 5.12-5.04 (m, 1H), 5.03-4.92 (m, 1H), 3.87-3.78 (m, 1H), 3.75-3.69 (m, 1H), 3.63-3.58 (m, 1H), 3.57-3.52 (m, 1H), 3.52-3.45 (m, 1H), 3.42-3.29 (m, 2H), 3.26-3.19 (m, 1H), 3.15-3.09 (m, 1H), 2.93-2.83 (m, 1H), 2.01-1.91 (m, 1H), 1.87-1.78 (m, 1H), 1.71-1.55 (m, 1H), 1.54-1.43 (m, 2H), 0.86-0.73 (m, 3H). MS ES+ m/z 354 [M+H]+.

Intermediate Example 30

(3R)-4-[2-tert-butoxy-6-(4-methyl-2-phenyl-piperazin-1-yl)-4-pyridyl]-3-methyl-morpholine

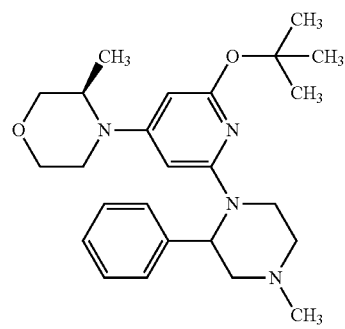 [SMILES: C[C@@H]1COCCN1c1cc(OC(C)(C)C)nc(N2CCN(C)CC2c2ccccc2)c1]

The title compound was prepared as described in Intermediate example 9, except the mixture was stirred for 2 h at 70° C., starting from (3R)-4-(2-tert-butoxy-6-chloro-4-pyridyl)-3-methyl-morpholine (100 mg, 0.35 mmol) and 1-methyl-3-phenyl-piperazine (93 mg, 0.53 mmol), to give the product (149 mg, 95%). MS ES+ m/z 425 [M+H]+.

Example 31

4-[(3R)-3-methylmorpholin-4-yl]-6-(4-methyl-2-phenyl-piperazin-1-yl)-1H-pyridin-2-one

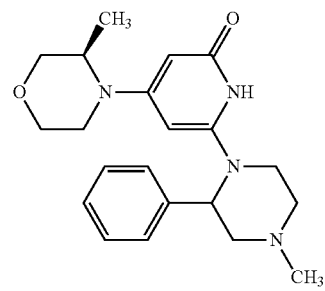 [SMILES: C[C@@H]1COCCN1c1cc(N2CCN(C)CC2c2ccccc2)[nH]c(=O)c1]

The title compound was prepared as described in Example 10, starting from (3R)-4-[2-tert-butoxy-6-(4-methyl-2-phenyl-piperazin-1-yl)-4-pyridyl]-3-methyl-morpholine (149 mg, 0.35 mmol) to give the product (42 mg, 32%). $^1$H NMR (500 MHz, DMSO) δ 7.41-7.09 (m, 5H), 5.84-5.68 (m, 1H), 5.41-5.20 (m, 1H), 5.19-4.88 (m, 1H), 3.88-3.78 (m, 1H), 3.78-3.68 (m, 1H), 3.65-3.50 (m, 2H), 3.47-3.08 (m, 5H), 3.02-2.94 (m, 0.5H), 2.94-2.81 (m, 1H), 2.73-2.63 (m, 1H), 2.61-2.55 (m, 0.5H), 2.45-2.38 (m, 0.5H), 2.37-2.28 (m, 0.5H), 2.17 (s, 3H), 1.09-0.97 (m, 1.5H), 0.84-0.71 (m, 1.5H). MS ES+ m/z 369 [M+H]+.

Intermediate Example 31

4-[6-tert-butoxy-4-[(3R)-3-methylmorpholin-4-yl]-2-pyridyl]-3-(trifluoromethyl)morpholine

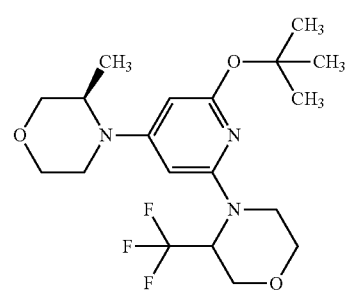 [SMILES: C[C@@H]1COCCN1c1cc(OC(C)(C)C)nc(N2CCOCC2C(F)(F)F)c1]

The title compound was prepared as described in Intermediate example 9, except the mixture was stirred overnight at 70° C., starting from (3R)-4-(2-tert-butoxy-6-chloro-4-pyridyl)-3-methyl-morpholine (100 mg, 0.35 mmol) and 3-(trifluoromethyl)morpholine hydrochloride (101 mg, 0.53 mmol), to give the product (74 mg, 52%). MS ES+ m/z 404 [M+H]+.

Example 32

4-[(3R)-3-methylmorpholin-4-yl]-6-[3-(trifluoromethyl)morpholin-4-yl]-1H-pyridin-2-one

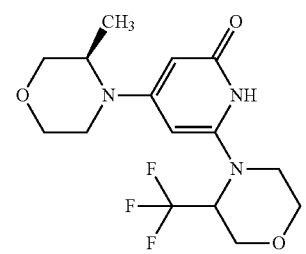 [SMILES: C[C@@H]1COCCN1c1cc(N2CCOCC2C(F)(F)F)[nH]c(=O)c1]

The title compound was prepared as described in Example 10, starting from 4-[6-tert-butoxy-4-[(3R)-3-methylmorpholin-4-yl]-2-pyridyl]-3-(trifluoromethyl)morpholine (74 mg, 0.18 mmol) to give the product (16 mg, 26%). $^1$H NMR (500 MHz, DMSO) δ 6.39-6.32 (m, 0.5H), 5.87-5.79 (m, 0.5H), 5.69-5.58 (m, 1H), 5.44-5.36 (m, 1H), 5.24-5.09 (m, 1H), 4.21-4.09 (m, 1H), 3.99-3.82 (m, 3H), 3.75-3.63 (m, 3H), 3.63-3.55 (m, 1H), 3.55-3.27 (m, 4H), 3.26-3.15 (m, 1H), 3.08-2.92 (m, 1H), 1.16-0.99 (m, 3H). MS ES+ m/z 348 [M+H]+.

Intermediate Example 32

(3R)-4-[2-tert-butoxy-6-(3-cyclopropylmorpholin-4-yl)-4-pyridyl]-3-methyl-morpholine

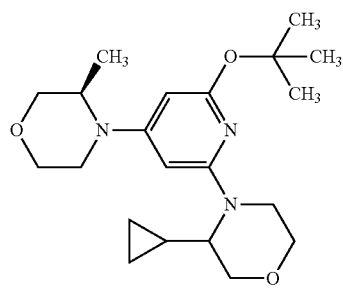 [SMILES: C[C@@H]1COCCN1c1cc(OC(C)(C)C)nc(N2CCOCC2C2CC2)c1]

The title compound was prepared as described in Intermediate example 9, except the mixture was stirred for 2 h at 70° C., starting from (3R)-4-(2-tert-butoxy-6-chloro-4-pyridyl)-3-methyl-morpholine (100 mg, 0.35 mmol) and 3-cyclopropylmorpholine (67 mg, 0.56 mmol), to give the product (93 mg, 70%). MS ES+ m/z 376 [M+H]$^+$.

Example 33

6-(3-cyclopropylmorpholin-4-yl)-4-[(3R)-3-methyl-morpholin-4-yl]-1H-pyridin-2-one

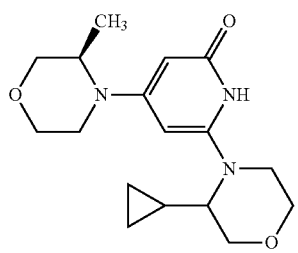 [SMILES: C[C@@H]1COCCN1c1cc(N2CCOCC2C2CC2)[nH]c(=O)c1]

The title compound was prepared as described in Example 10, starting from 4-[6-tert-butoxy-4-[(3R)-3-methylmorpholin-4-yl]-2-pyridyl]-3-(trifluoromethyl)morpholine (93 mg, 0.25 mmol) to give the product (6 mg, 7%). 1H NMR (500 MHz, CD$_3$OD) δ 5.30 (d, 1H), 5.15 (t, 1H), 3.84-3.73 (m, 5H), 3.70-3.53 (m, 4H), 3.52-3.46 (m, 1H), 3.46-3.36 (m, 1H), 3.33-3.18 (m, 3H), 3.08-2.99 (m, 1H), 2.91-2.78 (m, 2H), 2.73-2.63 (m, 1H), 1.32-1.21 (m, 1H), 1.08 (d, 1H), 1.05 (d, 2H), 0.37-0.22 (m, 3H), 0.14--0.07 (m, 3H). MS ES+ m/z 320 [M+H]$^+$.

Intermediate Example 33

(3R)-4-[2-tert-butoxy-6-[(2S)-2-(trifluoromethyl)pyrrolidin-1-yl]-4-pyridyl]-3-methyl-morpholine

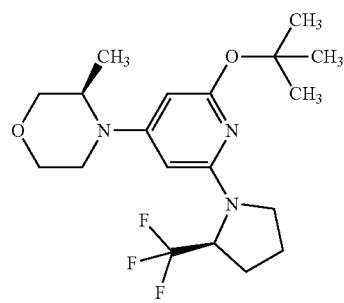 [SMILES: C[C@@H]1COCCN1c1cc(OC(C)(C)C)nc(N2CCC[C@H]2C(F)(F)F)c1]

The title compound was prepared as described in Intermediate example 9, except the mixture was stirred for 2 h at 70° C., starting from (3R)-4-(2-tert-butoxy-6-chloro-4-pyridyl)-3-methyl-morpholine (100 mg, 0.35 mmol) and (2S)-2-(trifluoromethyl)pyrrolidine (73 mg, 0.53 mmol), to give the product (79 mg, 58%). MS ES+ m/z 388 [M+H]$^+$.

Example 34

4-[(3R)-3-methylmorpholin-4-yl]-6-[(2S)-2-(trifluoromethyl)pyrrolidin-1-yl]-1H-pyridin-2-one

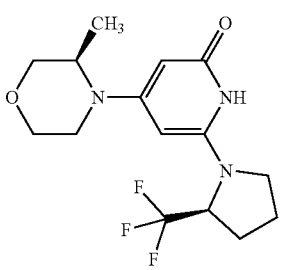 [SMILES: C[C@@H]1COCCN1c1cc(N2CCC[C@H]2C(F)(F)F)[nH]c(=O)c1]

The title compound was prepared as described in Example 10, starting from (3R)-4-[2-tert-butoxy-6-[(2S)-2-(trifluoromethyl)pyrrolidin-1-yl]-4-pyridyl]-3-methyl-morpholine (79 mg, 0.2 mmol) to give the product (36 mg, 53%). 1H NMR (500 MHz, DMSO-d$_6$) δ 9.74 (br s, 1H), 5.44 (s, 1H), 5.34 (s, 1H), 4.99 (m, 1H), 3.94-3.83 (m, 2H), 3.72-3.64 (m, 1H), 3.64-3.54 (m, 2H), 3.46 (td, 1H), 3.39-3.34 (m, 2H), 3.31-3.22 (m, 1H), 2.99 (td, 1H), 2.05-1.97 (m, 3H), 1.07 (d, 3H). MS ES+ m/z 332 [M+H]$^+$.

Intermediate Example 34

(3R)-4-[2-tert-butoxy-6-[(2R)-2-(trifluoromethyl)pyrrolidin-1-yl]-4-pyridyl]-3-methyl-morpholine

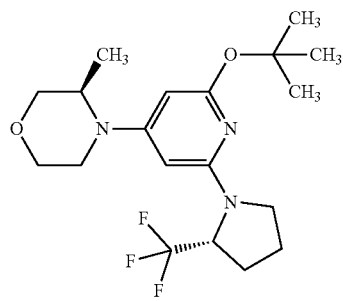 [SMILES: C[C@@H]1COCCN1c1cc(OC(C)(C)C)nc(N2CCC[C@@H]2C(F)(F)F)c1]

The title compound was prepared as described in Intermediate example 9, except the mixture was stirred for 2 h at 70° C., starting from (3R)-4-(2-tert-butoxy-6-chloro-4-pyridyl)-3-methyl-morpholine (100 mg, 0.35 mmol) and (2R)-2-(trifluoromethyl)pyrrolidine (73 mg, 0.53 mmol), to give the product (76 mg, 56%). MS ES+ m/z 388 [M+H]+.

Example 35

4-[(3R)-3-methylmorpholin-4-yl]-6-[(2R)-2-(trifluoromethyl)pyrrolidin-1-yl]-1H-pyridin-2-one

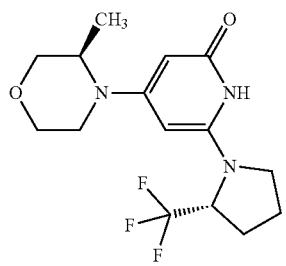 [SMILES: C[C@@H]1COCCN1c1cc(N2CCC[C@@H]2C(F)(F)F)[nH]c(=O)c1]

The title compound was prepared as described in Example 10, starting from (3R)-4-[2-tert-butoxy-6-[(2R)-2-(trifluoromethyl)pyrrolidin-1-yl]-4-pyridyl]-3-methyl-morpholine (76 mg, 0.2 mmol) to give the product (34 mg, 52%). 1H NMR (500 MHz, DMSO-d$_6$) δ 9.75 (br s, 1H), 5.44 (s, 1H), 5.33 (s, 1H), 4.98 (m, 1H), 3.89 (m, 2H), 3.73-3.65 (m, 1H), 3.65-3.55 (m, 2H), 3.46 (td, 1H), 3.32-3.24 (m, 2H), 2.99 (td, 1H), 2.12-1.95 (m, 4H), 1.07 (d, 3H). MS ES+ m/z 332 [M+H]+.

Example 36

(R) and (S) 6-[2-(3-chlorophenyl)pyrrolidin-1-yl]-4-[(3R)-3-methylmorpholin-4-yl]-1H-pyridin-2-one

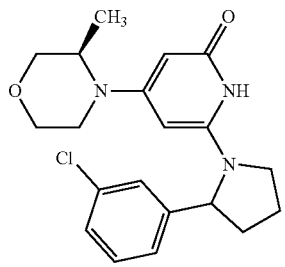 [SMILES: C[C@@H]1COCCN1c1cc(N2CCCC2c2cccc(Cl)c2)[nH]c(=O)c1]

(3R)-4-(2-tert-butoxy-6-chloro-4-pyridyl)-3-methyl-morpholine (1 g, 3.52 mmol), 2-(3-chlorophenyl)pyrrolidine (764 mg, 4.2 mmol), Chloro(2-dicyclohexylphosphino-2',4',6'-triisopropyl-1,1'-biphenyl)[2-(2'-amino-1,1'-biphenyl)]palladium(II) (110 mg, 0.35 mmol) and K$_3$PO$_4$ (1.5 g, 7.04 mmol) were taken up in anh. 1,4-Dioxane (10 ml) and degassed with nitrogen for 5 min. The resulting mixture was heated in a microwave reactor at 100° C. for 1 h. When cooled to rt the mixture was filtered through celite and the filtrate was diluted with water and extracted with EtOAc. The combined organics were washed with brine, filtered, concentrated and purified on a silica gel column eluted with 20% EtOAc/Petroleum ether. The intermediate was dissolved in DCM (10 ml) and TFA (1.87 ml, 24.5 mmol) was added slowly at 0° C. The reaction mixture was stirred at rt for 1 h, then basified with sat. aq. NaHCO$_3$ and extracted with DCM. The combined organics were washed with brine, dried over Na$_2$SO$_4$, filtered, concentrated and purified on a silica gel column eluted with 5% MeOH/DCM to give the title compound (190 mg, 14%). 1H NMR (400 MHz, CDCl$_3$) δ 7.27 (br s, 1H), 7.25-7.24 (m, 1H), 7.17 (s, 1H), 7.07 (br d, 1H), 5.15 (dd, 1H), 4.77-4.64 (m, 2H), 3.95-3.89 (m, 1H), 3.76-3.65 (m, 3H), 3.59-3.45 (m, 3H), 3.20-3.06 (m, 2H), 2.49-2.38 (m, 1H), 2.08-1.91 (m, 3H), 1.21 (d, 1.5H), 0.99 (d, 1.5H). MS ES+ m/z 374 [M+H]+. Chiral separation by SFC gave the two isomers.

Example 36-1, First Isomer to Elute, with Unknown Absolute Configuration

1H NMR (400 MHz, DMSO-d$_6$) δ 7.33 (d, 1H), 7.29-7.26 (m, 1H), 7.22 (s, 1H), 7.15 (br d, 1H), 5.05-4.90 (m, 3H), 3.83 (br dd, 1H), 3.73-3.40 (m, 6H), 3.19 (br d, 1H), 2.86 (dt, 1H), 2.35-2.27 (m, 1H), 1.93-1.77 (m, 3H), 1.04 (d, 3H). MS ES+ m/z 374 [M+H]+.

Example 36-2, Second Isomer to Elute, with Unknown Absolute Configuration

1H NMR (400 MHz, DMSO-d$_6$) δ 7.33 (d, 1H), 7.28-7.24 (m, 2H), 7.17 (br d, 1H), 4.99-4.79 (m, 3H), 3.84-3.73 (m, 2H), 3.62-3.33 (m, 5H), 3.10 (br d, 1H), 2.88 (dt, 1H), 2.38-2.30 (m, 1H), 1.93-1.75 (m, 3H), 0.77 (br d, 3H). MS ES+ m/z 374 [M+H]+.

Example 37

6-[2-(3-cyclopropylphenyl)pyrrolidin-1-yl]-4-[(3R)-3-methylmorpholin-4-yl]-1H-pyridin-2-one

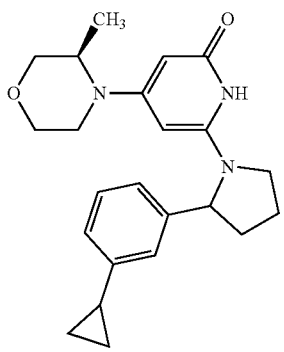 [SMILES: C[C@@H]1COCCN1c1cc(N2CCCC2c2cccc(C3CC3)c2)[nH]c(=O)c1]

2-cyclopropyl-4,4,5,5-tetramethyl-1,3,2-dioxaborolane (189 mg, 1.13 mmol), Chloro(2-dicyclohexylphosphino-2',4',6'-triisopropyl-1,1'-biphenyl)[2-(2'-amino-1,1'-biphenyl)]palladium(II) (29 mg, 0.09 mmol) and 0.5M aq. K$_3$PO$_4$ (5 ml) were taken up in THF (10 ml) and the resulting mixture was degassed with argon for 15 min. 6-[2-(3-chlorophenyl)pyrrolidin-1-yl]-4-[(3R)-3-methylmorpholin-4-yl]-1H-pyridin-2-one (350 mg, 0.93 mmol) was added and the resulting mixture was heated in a microwave reactor at 100° C. for 1 h. The reaction mixture was filtered through celite and the filtrate was diluted with water and extracted with ethyl acetate. The combined organics were washed with brine, dried over Na$_2$SO$_4$, filtered, concentrated and purified by preparative HPLC (using 0.1% formic acid in MeCN). The crude product was further purified on a silica gel column eluted with 5% MeOH/DCM to give the title compound (45 mg, 4%). $^1$H NMR (400 MHz, CDCl$_3$) δ 7.19 (td, 1H), 6.95-6.88 (m, 3H), 5.12 (dd, 1H), 4.77-4.66 (m, 2H), 3.95-3.89 (m, 1H), 3.72-3.64 (m, 3H), 3.59-3.43 (m, 3H), 3.21-3.09 (m, 2H), 2.41 (br dd, 1H), 2.10-1.92 (m, 3H), 1.86 (td, 1H), 1.21 (br d, 2H), 1.00-0.93 (m, 3H), 0.68-0.63 (m, 2H). MS ES+ m/z 380 [M+H]$^+$.

Intermediate Example 35

(3R)-4-[2-tert-butoxy-6-[2-(2-pyridyl)pyrrolidin-1-yl]-4-pyridyl]-3-methyl-morpholine

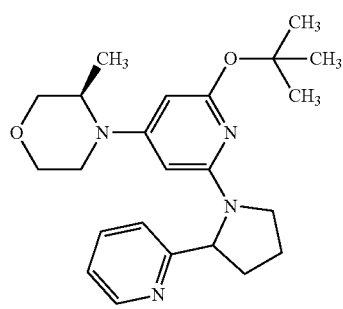 [SMILES: C[C@@H]1COCCN1c1cc(OC(C)(C)C)nc(N2CCCC2c2ccccn2)c1]

(3R)-4-(2-tert-butoxy-6-chloro-4-pyridyl)-3-methyl-morpholine (750 mg, 2.64 mmol), 2-pyrrolidin-2-ylpyridine (469 mg, 3.16 mmol) and KOtBu (591 mg, 5.3 mmol) were taken up in anh. 1,4-Dioxane (10 ml) and the resulting reaction mixture was degassed with nitrogen for 15 minutes. Then XPhos (207 mg, 0.26 mmol) and Pd(OAc)$_2$ (59 mg, 0.26 mmol) were added and the reaction mixture was stirred at 110° C. in sealed tube for 16 hours. When cooled to rt the mixture was filtered through celite and the filtrate was diluted with water and extracted with EtOAc. The combined organics were washed with brine, filtered, concentrated and purified on a silica gel column eluted with 20% EtOAc/Petroleum ether to give the title compound (470 mg, 45%). MS ES+ m/z 397 [M+H]$^+$.

Example 38

(R) and (S) 4-[(3R)-3-methylmorpholin-4-yl]-6-[2-(2-pyridyl)pyrrolidin-1-yl]-1H-pyridin-2-one

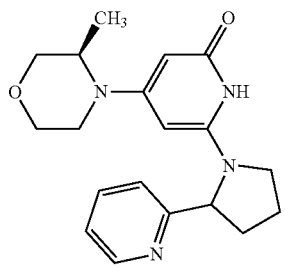 [SMILES: C[C@@H]1COCCN1c1cc(N2CCCC2c2ccccn2)[nH]c(=O)c1]

The title compound was prepared as described in Example 10, starting from (3R)-4-[2-tert-butoxy-6-[2-(2-pyridyl)pyrrolidin-1-yl]-4-pyridyl]-3-methyl-morpholine (470 mg, 1.18 mmol) to give the product as a diastereomeric mixture (230 mg, 57%). $^1$H NMR (400 MHz, CDCl$_3$) δ 8.61-8.57 (m, 1H), 7.69-7.63 (m, 1H), 7.19 (br t, 2H), 5.15 (br d, 1H), 4.88-4.82 (m, 1H), 4.73-4.67 (m, 1H), 3.90 (br d, 1H), 3.82-3.74 (m, 1H), 3.71-3.46 (m, 5H), 3.17-3.02 (m, 2H), 2.54-2.41 (m, 1H), 2.21-2.05 (m, 3H), 1.17 (br d, 1.5H), 0.93 (br d, 1.5H). MS ES+ m/z 341 [M+H]$^+$. Chiral separation by SFC gave the two isomers.

Example 38-1, First Isomer to Elute, with Unknown Absolute Configuration $^1$H NMR (400 MHz, CDCl$_3$) δ 8.60 (d, 1H), 7.66 (dt, 1H), 7.23-7.17 (m, 2H), 5.16 (d, 1H), 4.87 (dd, 1H), 4.73 (d, 1H), 3.91 (dd, 1H), 3.77-3.62 (m, 4H), 3.56-3.48 (m, 2H), 3.18-3.02 (m, 2H), 2.46 (qd, 1H), 2.22-2.06 (m, 3H), 1.18 (d, 3H). MS ES+ m/z 341 [M+H]$^+$.

Example 38-2, Second Isomer to Elute, with Unknown Absolute Configuration $^1$H NMR (400 MHz, CDCl$_3$) δ 8.58 (dd, 1H), 7.64 (dt, 1H), 7.21-7.16 (m, 2H), 5.14 (d, 1H), 4.84 (dd, 1H), 4.67 (d, 1H), 3.92-3.80 (m, 2H), 3.66-3.46 (m, 5H), 3.14-3.03 (m, 2H), 2.54-2.44 (m, 1H), 2.18-2.05 (m, 2H), 0.93 (d, 3H). MS ES+ m/z 341 [M+H]$^+$.

Intermediate Example 36

(3R)-4-[2-tert-butoxy-6-(2-thiazol-2-ylpyrrolidin-1-yl)-4-pyridyl]-3-methyl-morpholine

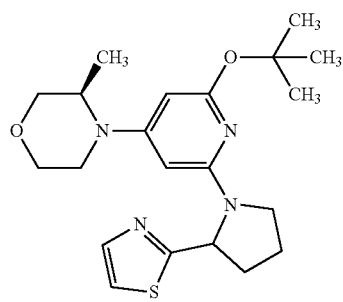 [SMILES: C[C@@H]1COCCN1c1cc(OC(C)(C)C)nc(N2CCCC2c2nccs2)c1]

The title compound was prepared as described in Intermediate example 35, starting from (3R)-4-(2-tert-butoxy-6-chloro-4-pyridyl)-3-methyl-morpholine (400 mg, 1.4 mmol) and 2-pyrrolidin-2-ylthiazole hydrochloride (321 mg, 1.69 mmol), to give the product (110 mg, 19%). MS ES+ m/z 403 [M+H]+.

Example 39

(R) and (S) 4-[(3R)-3-methylmorpholin-4-yl]-6-(2-thiazol-2-ylpyrrolidin-1-yl)-1H-pyridin-2-one

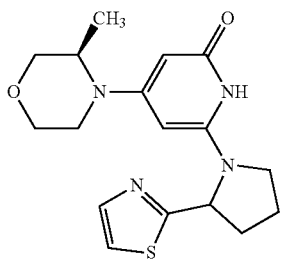 [SMILES: C[C@@H]1COCCN1c1cc(N2CCCC2c2nccs2)[nH]c(=O)c1]

The title compound was prepared as described in Example 10, starting from (3R)-4-[2-tert-butoxy-6-(2-thiazol-2-ylpyrrolidin-1-yl)-4-pyridyl]-3-methyl-morpholine (100 mg, 0.24 mmol) to give the product as a diastereomeric mixture (10 mg, 12%). $^1$H NMR (400 MHz, CDCl$_3$) δ 7.75 (dd, 1H) 5.25-5.12 (m, 2H) 4.88 (br s, 1H) 3.92 (br d, 1H) 3.72-3.64 (m, 4H) 3.54-3.48 (m, 2H) 3.21-3.11 (m, 2H) 2.48 (br d, 1H) 2.28-2.14 (m, 4H) 1.25 (s, 1H) 1.19 (br d, 1H) 1.01 (br d, 1H). MS ES+ m/z 347 [M+H]+.

Example 40

(R) and (S) 6-[2-(5-methylisoxazol-3-yl)pyrrolidin-1-yl]-4-[(3R)-3-methylmorpholin-4-yl]-1H-pyridin-2-one

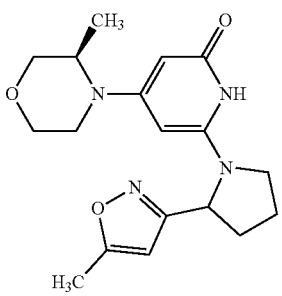 [SMILES: Cc1cc(C2CCCN2c2cc(N3CCOC[C@H]3C)cc(=O)[nH]2)no1]

(3R)-4-(2-tert-butoxy-6-chloro-4-pyridyl)-3-methyl-morpholine (500 mg, 1.76 mmol), 5-methyl-3-pyrrolidin-2-yl-isoxazole (321 mg, 2.11 mmol) and KOtBu (3.94 mg, 3.5 mmol) were taken up in toluene (10 ml) and the resulting reaction mixture was degassed with nitrogen for 15 minutes. Then XPhos (138 mg, 0.17 mmol) and Pd(OAc)$_2$ (39 mg, 0.17 mmol) were added and the reaction mixture was stirred at 110° C. in sealed tube for 16 hours. When cooled to rt the mixture was filtered through celite and the filtrate was diluted with water and extracted with EtOAc. The combined organics were washed with brine, filtered, concentrated and purified by preparative HPLC (using 0.1% formic acid in MeCN) to give the product as a diastereomeric mixture (200 mg, 33%). $^1$H NMR (400 MHz, CDCl$_3$) b 5.83 (br d, 1H) 5.17 (br s, 1H) 4.92-4.87 (m, 2H) 3.94 (br d, 1H) 3.74-3.68 (m, 4H) 3.52 (br d, 2H) 3.24-3.10 (m, 2H) 2.38 (d, 4H) 2.12 (br s, 3H) 1.20 (br d, 1.5H) 1.05 (br d, 1.5H). MS ES+ m/z 345 [M+H]+. Chiral separation by SFC gave the two isomers.

Example 40-1, First Isomer to Elute, with Unknown Absolute Configuration $^1$H NMR (400 MHz, CDCl$_3$) δ 5.84 (s, 1H) 5.16 (s, 1H) 4.92-4.89 (m, 2H) 3.94 (br dd, 1H) 3.75-3.68 (m, 4H) 3.55-3.49 (m, 2H) 3.24-3.19 (m, 1H) 3.12 (br dd, 1H) 2.38 (s, 4H) 2.12 (br t, 3H) 1.20 (br d, 3H). MS ES+ m/z 345 [M+H]+.

Example 40-2, Second Isomer to Elute, with Unknown Absolute Configuration $^1$H NMR (400 MHz, CDCl$_3$) δ 5.83 (s, 1H) 5.16 (br s, 1H) 4.90 (br s, 2H) 3.92 (br s, 1H) 3.70 (br d, 4H) 3.53 (br s, 2H) 3.16 (br s, 2H) 2.37 (s, 4H) 2.12 (br s, 3H) 1.06 (br s, 3H). MS ES+ m/z 345 [M+H]+.

Example 41

1-methyl-4-[(3R)-3-methylmorpholin-4-yl]-6-[(2R)-2-(trifluoromethyl)-1-piperidyl]pyridin-2-one

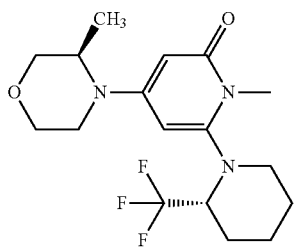 [SMILES: C[C@@H]1COCCN1c1cc(N2CCCC[C@@H]2C(F)(F)F)n(C)c(=O)c1]

LiOtBu (111 mg, 1.39 mmol) and Methyl iodide (0.19 ml, 1.39 mmol) were added to a solution of 4-[(3R)-3-methylmorpholin-4-yl]-6-[(2R)-2-(trifluoromethyl)-1-piperidyl]-1H-pyridin-2-one (240 mg, 0.7 mmol) in Acetone (10 ml) and the resulting mixture was stirred at 80° C. for 1 h. When cooled to rt the mixture was concentrated. Water (10 ml) was added and the mixture extracted with EtOAc (3×10 ml). The combined organics were washed with brine, dried over $Na_2SO_4$, filtered, concentrated and purified by preparative HPLC to give the product as a solid (40 mg, 12%). $^1$H NMR (400 MHz, DMSO-$d_6$) VT 90° C.: δ 5.80 (s, 1H), 5.31 (d, 1H), 4.04-3.85 (m, 3H), 3.67-3.61 (m, 2H), 3.50-3.43 (m, 1H), 3.26-3.18 (m, 5H), 3.06-3.02 (m, 1H), 2.88-2.85 (m, 1H), 2.00-1.99 (m, 1H), 1.83-1.81 (m, 1H), 1.70-1.60 (m, 4H), 1.08 (d, 3H). MS ES+ m/z 360 [M+H]$^+$.

Intermediate Example 37

5-[6-tert-butoxy-4-[(3R)-3-methylmorpholin-4-yl]-2-pyridyl]-8-oxa-5-azaspiro[3.5]nonane

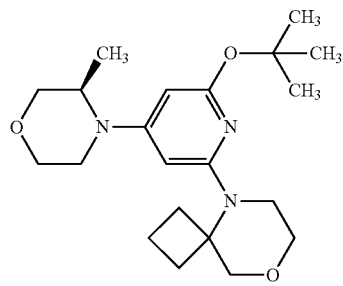 [SMILES: C[C@@H]1COCCN1c1cc(OC(C)(C)C)nc(N2CCOCC23CCC3)c1]

The title compound was prepared as described in Intermediate example 9 except the mixture was heated in a microwave reactor at 130° C. for 2 h, starting from (3R)-4-(2-tert-butoxy-6-chloro-4-pyridyl)-3-methyl-morpholine (100 mg, 0.35 mmol) and 8-oxa-5-azaspiro[3.5]nonane (54 mg, 0.42 mmol), to give the product (86 mg, 65%). MS ES+m/z 376 [M+H]$^+$.

Example 42

4-[(3R)-3-methylmorpholin-4-yl]-6-(8-oxa-5-azaspiro[3.5]nonan-5-yl)-1H-pyridin-2-one

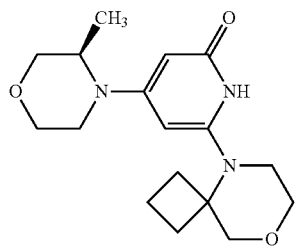 [SMILES: C[C@@H]1COCCN1c1cc(N2CCOCC23CCC3)[nH]c(=O)c1]

The title compound was prepared as described in Example 10, starting from 5-[6-tert-butoxy-4-[(3R)-3-methylmorpholin-4-yl]-2-pyridyl]-8-oxa-5-azaspiro[3.5]nonane (130 mg, 0.35 mmol) to give the product (35 mg, 31%). $^1$H NMR (500 MHz, DMSO-$d_6$). δ 10.21 (br. s, 1H), 5.21 (s, 1H), 5.11 (s, 1H), 3.88-3.83 (m, 2H), 3.69-3.58 (m, 4H), 3.48-3.42 (m, 3H), 3.31-3.28 (m, 1H), 3.18-3.17 (m, 2H), 2.99-2.96 (m, 1H), 2.08-2.00 (m, 4H), 1.64-1.61 (m, 2H), 1.07 (d, 3H). MS ES+ m/z 320 [M+H]$^+$.

Intermediate Example 38

4-[6-tert-butoxy-4-[(3R)-3-methylmorpholin-4-yl]-2-pyridyl]-3-(trifluoromethyl)morpholine

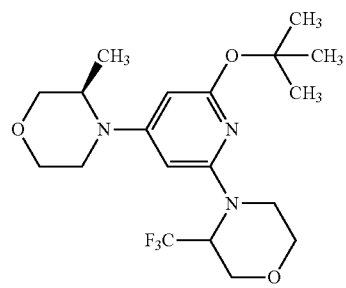 [SMILES: C[C@@H]1COCCN1c1cc(OC(C)(C)C)nc(N2CCOCC2C(F)(F)F)c1]

The title compound was prepared as described in Intermediate example 9 except the mixture was heated in a microwave reactor at 150° C. for 3 h, starting from (3R)-4-(2-tert-butoxy-6-chloro-4-pyridyl)-3-methyl-morpholine (400 mg, 1.4 mmol) and 3-(trifluoromethyl)morpholine (330 mg, 1.68 mmol), to give the product (330 mg, 58%). MS ES+ m/z 404 [M+H]$^+$.

Example 43

4-[(3R)-3-methylmorpholin-4-yl]-6-[3-(trifluoromethyl)morpholin-4-yl]-1H-pyridin-2-one

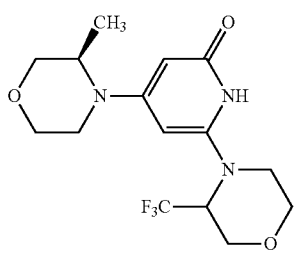 [SMILES: C[C@@H]1COCCN1c1cc(N2CCOCC2C(F)(F)F)[nH]c(=O)c1]

The title compound was prepared as described in Example 10, starting from 4-[6-tert-butoxy-4-[(3R)-3-methylmorpholin-4-yl]-2-pyridyl]-3-(trifluoromethyl)morpholine (350 mg, 0.87 mmol) to give the product as a diastereomeric mixture (200 mg, 65%). MS ES+ m/z 348 [M+H]⁺. Chiral separation by SFC gave the two isomers.

Example 43-1, First Isomer to Elute, with Unknown Absolute Configuration

¹H NMR (400 MHz, DMSO-d₆): δ 9.9-9.6 (br. s, 1H), 5.62 (d, 1H), 5.38 (s, 1H), 5.15 (br. s, 1H), 4.13 (d, 1H), 3.91-3.86 (m, 2.3H), 3.67-3.58 (m, 3H), 3.5-3.4 (m, 2H), 3.38-3.25 (m, 3H), 3.17 (q, 1H), 3.01-2.95 (m, 1H), 1.06 (d, 3H). MS ES+ m/z 348 [M+H]⁺.

Example 43-2, Second Isomer to Elute, with Unknown Absolute Configuration

¹H NMR (400 MHz, DMSO-d₆): δ 9.9-9.6 (br. s, 1H), 5.62 (s, 1H), 5.38 (s, 1H), 5.15 (br. s, 1H), 4.13 (d, 1H), 3.91-3.86 (m, 3H), 3.68-3.57 (m, 4H), 3.49-3.42 (m, 2H), 3.286 (s, 1H), 3.17 (q, 1H), 3.01-2.94 (m, 1H), 1.06 (d, 3H). MS ES+ m/z 348 [M+H]⁺.

Intermediate Example 39

(3R)-4-[2-tert-butoxy-6-[2-(3-methoxyphenyl)-1-piperidyl]-4-pyridyl]-3-methyl-morpholine

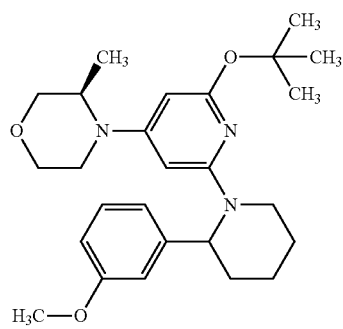 [SMILES: COc1cccc(C2CCCCN2c2cc(N3CCOC[C@H]3C)cc(OC(C)(C)C)n2)c1]

The title compound was prepared as described in Intermediate example 9 except the mixture stirred for 4 h, starting from (3R)-4-(2-tert-butoxy-6-chloro-4-pyridyl)-3-methyl-morpholine (500 mg, 1.7 mmol) and 2-(3-methoxyphenyl) piperidine (404 mg, 2.11 mmol), to give the product (460 mg, 61%). MS ES+ m/z 440 [M+H]⁺.

Example 44

6-[2-(3-methoxyphenyl)-1-piperidyl]-4-[(3R)-3-methylmorpholin-4-yl]-1H-pyridin-2-one

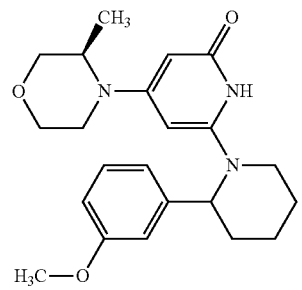 [SMILES: COc1cccc(C2CCCCN2c2cc(N3CCOC[C@H]3C)cc(=O)[nH]2)c1]

The title compound was prepared as described in Example 10, starting from (3R)-4-[2-tert-butoxy-6-[2-(3-methoxyphenyl)-1-piperidyl]-4-pyridyl]-3-methyl-morpholine (460 mg, 1 mmol) to give the product as a diastereomeric mixture (390 mg, 98%). MS ES+ m/z 384 [M+H]⁺. Chiral separation by SFC gave the two isomers.

Example 44-1, First Isomer to Elute, with Unknown Absolute Configuration

¹H NMR (500 MHz, CDCl₃) δ 7.20 (t, 1H), 6.83-6.71 (m, 3H), 5.21 (d, 1H), 5.11 (d, 1H), 4.28 (br dd, 1H), 3.92 (br d, 1H), 3.75 (s, 3H), 3.68 (d, 2H), 3.59-3.43 (m, 3H), 3.16-3.03 (m, 3H), 2.01-1.85 (m, 2H), 1.81-1.70 (m, 4H), 0.89 (d, 3H). MS ES+ m/z 384 [M+H]⁺.

Example 44-2, Second Isomer to Elute, with Unknown Absolute Configuration

¹H NMR (400 MHz, CDCl₃) δ 7.26-7.20 (m, 1H), 6.84-6.74 (m, 3H), 5.22 (d, 1H), 5.11 (d, 1H), 4.56 (br t, 1H), 3.92 (br dd, 1H), 3.77 (s, 3H), 3.72-3.62 (m, 3H), 3.54 (dt, 1H), 3.41-3.31 (m, 2H), 3.20-3.04 (m, 2H), 2.10-1.93 (m, 2H), 1.73 (br dd, 4H), 1.19 (d, 3H). MS ES+ m/z 384 [M+H]⁺.

Intermediate Example 40 tert-butyl 4-[6-tert-butoxy-4-[(3R)-3-methylmorpholin-4-yl]-2-pyridyl]-3-(trifluoromethyl)piperazine-1-carboxylate

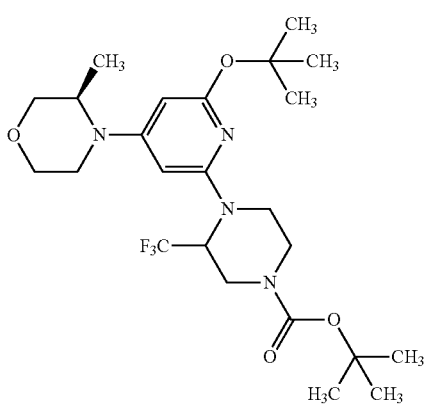 [SMILES: C[C@@H]1COCCN1c1cc(OC(C)(C)C)nc(N2CCN(C(=O)OC(C)(C)C)CC2C(F)(F)F)c1]

The title compound was prepared as described in Intermediate example 9 except the mixture was heated in a microwave reactor at 130° C. for 3 h, starting from (3R)-4-(2-tert-butoxy-6-chloro-4-pyridyl)-3-methyl-morpholine (200 mg, 0.7 mmol) and tert-butyl 3-(trifluoromethyl)piperazine-1-carboxylate (214 mg, 0.84 mmol), to give the product (150 mg, 43%). MS ES+ m/z 503 [M+H]+.

Intermediate Example 41

4-[(3R)-3-methylmorpholin-4-yl]-6-[2-(trifluoromethyl)piperazin-1-yl]-1H-pyridin-2-one

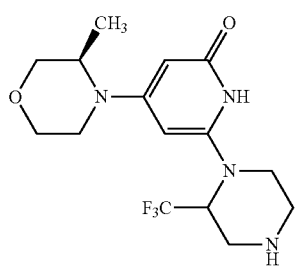 [SMILES: C[C@@H]1COCCN1c1cc(N2CCNCC2C(F)(F)F)[nH]c(=O)c1]

The title compound was prepared as described in Example 10, starting from tert-butyl 4-[6-tert-butoxy-4-[(3R)-3-methylmorpholin-4-yl]-2-pyridyl]-3-(trifluoromethyl)piperazine-1-carboxylate (300 mg, 0.6 mmol) to give the product (150 mg, 72%). MS ES+ m/z 347 [M+H]+.

Example 45

6-[4-acetyl-2-(trifluoromethyl)piperazin-1-yl]-4-[(3R)-3-methylmorpholin-4-yl]-1H-pyridin-2-one

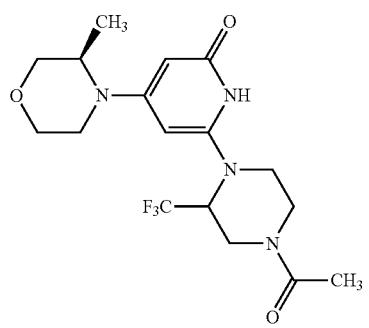 [SMILES: CC(=O)N1CCN(c2cc(N3CCOC[C@H]3C)cc(=O)[nH]2)C(C(F)(F)F)C1]

Acetyl chloride (0.04 ml, 0.53 mmol) and Et3N (0.1 ml, 0.7 mmol) were added to a solution of 4-[(3R)-3-methylmorpholin-4-yl]-6-[2-(trifluoromethyl)piperazin-1-yl]-1H-pyridin-2-one (100 mg, 0.35 mmol) in DCM (2 ml) at 0° C. The mixture was stirred at 0° C. for 30 min. Water (5 ml) was added and the mixture extracted with DCM (3×5 ml). The combined organics were washed with brine, dried over Na2SO4, filtered and concentrated. The residue was taken up in EtOH (1 ml) and 3 M Methylamine in EtOH (3 ml) was added at rt. The resulting mixture was stirred at rt for 1 h, concentrated and purified by preparative HPLC to give the product (60 mg, 53%). 1H NMR (400 MHz, DMSO-d6): δ 9.77 (br. s, 1H), 5.65 (s, 1H), 5.43 (s, 1H), 5.33 (bs, 1H), 3.90-3.86 (m, 4H), 3.67-3.63 (m, 2H), 3.51-3.45 (m, 2H), 3.34-3.28 (m, 3H), 3.20-3.18 (m, 2H), 3.08-3.01 (m, 2H), 2.01 (s, 2H), 1.10-1.08 (m, 3H). MS ES+ m/z 389 [M+H]+.

Example 46

6-[4-(5-fluoropyridine-3-carbonyl)-2-(trifluoromethyl)piperazin-1-yl]-4-[(3R)-3-methylmorpholin-4-yl]-1H-pyridin-2-one

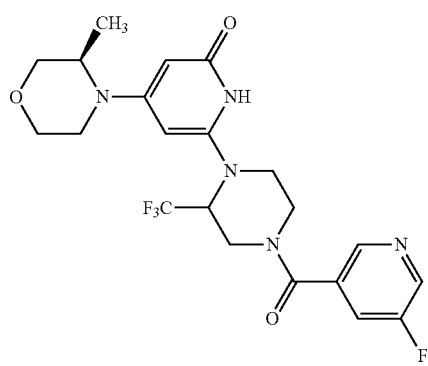 [SMILES: C[C@@H]1COCCN1c1cc(N2CCN(C(=O)c3cncc(F)c3)CC2C(F)(F)F)[nH]c(=O)c1]

To a stirred solution of 4-[(3R)-3-methylmorpholin-4-yl]-6-[2-(trifluoromethyl)piperazin-1-yl]-1H-pyridin-2-one (100 mg, 0.3 mmol) and 5-fluoropyridine-3-carboxylic acid (45 mg, 0.32 mmol) in DMF (2 ml), were added DIPEA (0.15 ml, 0.87 mmol) and T3P (0.17 ml, 0.58 mmol) at 0° C. The reaction mixture was stirred at rt for 1 h. The mixture was poured in to ice cold water (10 mL) and extracted with EtOAc (3×10 mL). The combined organics were washed with brine, dried over Na2SO4, filtered, concentrated and purified by preparative HPLC to give the product (30 mg, 22%). 1H NMR (400 MHz, DMSO-d6) VT at 90° C.: δ 9.40 (br. s, 1H), 8.64 (d, 1H), 8.43 (s, 1H), 7.77 (d, 1H), 5.67 (s, 1H), 5.44 (s 1H), 5.40 (br. s, 1H), 4.31 (br. s, 1H), 3.93-3.67 (m, 4H), 3.67-3.60 (m, 2H), 3.50-3.45 (m, 2H), 3.34-2.23 (m, 3H), 3.07-2.96 (m, 1H), 1.10-1.07 (m, 3H). MS ES+ m/z 470 [M+H]+.

Example 47

6-[4-[2-(4-fluorophenyl)acetyl]-2-(trifluoromethyl)piperazin-1-yl]-4-[(3R)-3-methylmorpholin-4-yl]-1H-pyridin-2-one

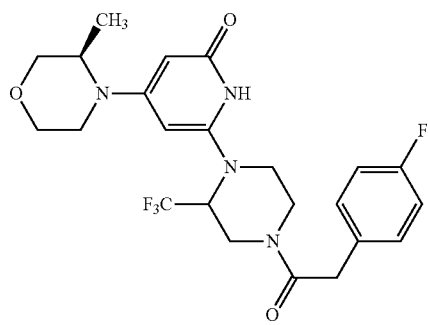 [SMILES: C[C@@H]1COCCN1c1cc(N2CCN(C(=O)Cc3ccc(F)cc3)CC2C(F)(F)F)[nH]c(=O)c1]

The title compound was prepared as described in Example 49, replacing 5-fluoropyridine-3-carboxylic acid with 2-(4-fluorophenyl)acetic acid (49 mg, 0.32 mmol) to give the product (40 mg, 28%). $^1$H NMR (400 MHz, DMSO-d$_6$) VT 90° C.: δ 9.40 (br. s, 1H), 7.22 (t, 2H), 7.06 (t, 2H), 5.64 (s, 1H), 5.43 (s, 1H), 5.34 (br. s, 1H), 4.46 (br. s, 1H), 4.00-3.86 (m, 4H), 3.76-3.60 (m, 4H), 3.48 (t, 1H), 3.34-3.03 (m, 5H), 1.09 (t, 3H). MS ES+ m/z 483 [M+H]$^+$.

Example 48

4-[(3R)-3-methylmorpholin-4-yl]-6-[4-(tetrahydrofuran-2-carbonyl)-2-(trifluoromethyl)piperazin-1-yl]-1H-pyridin-2-one

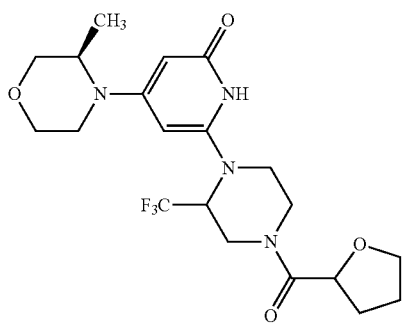 [SMILES: C[C@@H]1COCCN1c1cc(N2CCN(C(=O)C3CCCO3)CC2C(F)(F)F)[nH]c(=O)c1]

The title compound was prepared as described in Example 49, replacing 5-fluoropyridine-3-carboxylic acid with tetrahydrofuran-2-carboxylic acid (36 mg, 0.32 mmol). Purification by SFC provided two products.

Example 48-1, First Isomer to Elute, with Unknown Absolute Configuration (10 mg, 8%)

$^1$H NMR (400 MHz, DMSO-d$_6$) VT at 90° C.: δ 9.40 (br. s, 1H), 5.65 (s, 1H), 5.42 (s, 1H), 5.34 (br. s, 1H), 4.62-4.59 (m, 1H), 4.49 (br. s, 1H), 4.11-4.08 (m, 1H), 3.93-3.85 (m, 3H), 3.75 (t, 2H), 3.67-3.60 (m, 2H), 3.50-3.45 (m, 1H), 3.34-3.17 (m, 3H), 3.08-3.04 (m, 2H), 2.15-2.11 (m, 1H), 1.97-1.90 (m, 1H), 1.87-1.81 (m 2H), 1.10-1.08 (m, 3H). MS ES+ m/z 445 [M+H]$^+$.

Example 48-2, Second Isomer to Elute, with Unknown Absolute Configuration (15 mg, 12%)

$^1$H NMR (400 MHz, DMSO-d$_6$) VT at 90° C.: δ 9.45 (br s, 1H), 5.65 (s, 1H), 5.42 (s, 1H), 5.34 (br. s, 1H), 4.66-4.62 (m, 1H), 4.49 (br. s, 1H), 4.04-4.02 (m, 1H), 3.89-3.85 (m, 3H), 3.82-3.71 (m, 2H), 3.67-3.60 (m, 2H), 3.51-3.45 (m, 1H), 3.34-3.28 (m, 1H), 3.20-3.18 (m, 2H), 3.08-3.04 (m, 2H), 2.05-2.00 (m, 2H), 1.88-1.80 (m, 2H), 1.11-1.08 (m, 3H). MS ES+ m/z 445 [M+H]$^+$.

Intermediate Example 42

(3R)-4-[2-tert-butoxy-6-[2-(trifluoromethyl)piperazin-1-yl]-4-pyridyl]-3-methyl-morpholine

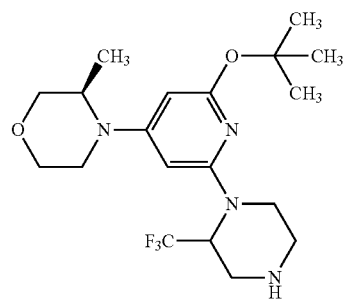 [SMILES: C[C@@H]1COCCN1c1cc(OC(C)(C)C)nc(N2CCNCC2C(F)(F)F)c1]

Lithium aluminum hydride (56 mg, 1.5 mmol) was added to a solution of tert-butyl 4-[6-tert-butoxy-4-[(3R)-3-methylmorpholin-4-yl]-2-pyridyl]-3-(trifluoromethyl)piperazine-1-carboxylate (250 mg, 0.5 mmol) in THF (5 ml) at 0° C. The reaction mixture was stirred at rt overnight and quenched with sat. aq. Na$_2$SO$_4$ and EtOAc. The mixture was filtered through celite and the filtrate was concentrated to give the product (120 mg, 60%). MS ES+ m/z 403 [M+H]$^+$.

Intermediate Example 43

(3R)-4-[2-tert-butoxy-6-[4-methyl-2-(trifluoromethyl)piperazin-1-yl]-4-pyridyl]-3-methyl-morpholine

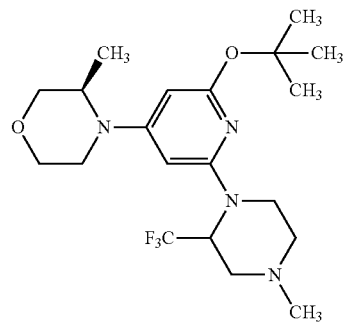 [SMILES: C[C@@H]1COCCN1c1cc(OC(C)(C)C)nc(N2CCN(C)CC2C(F)(F)F)c1]

37% aq. Formaldehyde (0.05 ml, 0.56 mmol) and acetic acid (0.03 mml, 0.56 mmol) was added to a solution of (3R)-4-[2-tert-butoxy-6-[2-(trifluoromethyl)piperazin-1-yl]-4-pyridyl]-3-methyl-morpholine (75 mg, 0.19 mmol) in MeOH (2 ml) at rt. After 10 min NaBH$_3$CN (35 mg, 0.56 mmol) was added and the mixture stirred at rt for 1 h. The mixture was concentrated and the resulting residue was taken up in water (10 ml) and EtOAc (10 ml). The organic layer was separated and the aqueous layer extracted with EtOAc (2×10 ml). The combined organics were washed with brine, dried over Na$_2$SO$_4$, filtered, concentrated and purified by preparative HPLC to give the product as a solid (30 mg, 38%). MS ES+ m/z 417 [M+H]$^+$.

Example 49

4-[(3R)-3-methylmorpholin-4-yl]-6-[4-methyl-2-(trifluoromethyl)piperazin-1-yl]-1H-pyridin-2-one

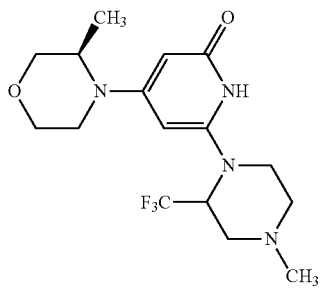 [SMILES: C[C@@H]1COCCN1c1cc(N2CCN(C)CC2C(F)(F)F)[nH]c(=O)c1]

The title compound was prepared as described in Example 10, starting from (3R)-4-[2-tert-butoxy-6-[4-methyl-2-(trifluoromethyl)piperazin-1-yl]-4-pyridyl]-3-methyl-morpholine (60 mg, 0.14 mmol) to give the product (25 mg, 48%). $^1$H NMR (400 MHz, DMSO-$d_6$): δ 9.33 (br. s, 1H), 5.57 (s, 1H), 5.36 (s, 1H), 5.26-5.24 (m, 1H), 3.87-3.66 (m 3H), 3.63-3.59 (m, 2H), 3.50-3.44 (m, 1H), 3.33-3.17 (m, 2H), 3.06-3.01 (m, 2H), 2.77-2.75 (m, 1H), 2.19 (s, 3H), 2.15-2.12 (m, 1H), 1.94-1.89 (m, 1H), 1.10-1.07 (m, 3H). MS ES+ m/z 361 [M+H]$^+$.

Example 50

Vps34 Biochemical Assay

Dilution series of compounds of the invention were prepared in DMSO at 100 times the final assay concentration ($n_1 = n_0/3$ in 10 points). The compounds were further diluted to 4 times the assay concentration in assay buffer (Life technologies buffer Q, PV5125, diluted 5 times supplemented with 2 mM DTT and 2 mM MnCl$_2$). 2.5 µl of the diluted compounds were added to a 384 well assay plate followed by 2.5 µl of 16.5 nM Vps34 enzyme (Life technologies, PV5126). Enzyme and compounds were pre-incubated at rt for 15 min. Then 5 µl of substrate mix containing 20 µM ATP (Life technologies, PV3227) and 200 µM PI:PS substrate (Life technologies, PV5122) in assay buffer was added to the wells containing compound and enzyme. Mixing was performed by pipetting several times. The reaction was incubated at room temperature for 1 h. Then 5 µl stop-detection mix, prepared as described in the Adapta kinase assay kit instructions (Life technologies, PV5099) containing Adapta Eu-anti-ADP antibody (2.3 nM), Alexa Fluor 647 ADP tracer (9 nM) and EDTA (30 mM) in TR-FRET buffer, was added to quench the reaction. Mixing was performed by pipetting several times. The assay plate was then incubated at room temperature for 30 min and read with Artemis micro plate reader. Percent inhibition of the compounds as compared to DMSO treated control samples was calculated. By the use of Dotmatics software compound concentration versus percent inhibition was fitted to generate IC$_{50}$ values.

The example compounds effectively inhibited Vps34 and the results of the assay are shown in Table 1 (Median IC$_{50}$ µM Adapta).

TABLE 1

Median IC$_{50}$ values for the Vps34 assay

| Example Compound | Median IC50 uM Adapta |
|---|---|
| 1 | 0.05 |
| 2 | 0.1 |
| 3 | 0.2 |
| 4 | 0.05 |
| 5 | 0.2 |
| 6 | 0.2 |
| 7 | 0.004 |
| 8 | 0.05 |
| 9 | 0.02 |
| 10 | 0.4 |
| 11 | 0.09 |
| 11_1 | 0.2 |
| 11_2 | 0.3 |
| 12 | 0.09 |
| 12_1 | 0.2 |
| 12_2 | 0.2 |
| 13 | 0.02 |
| 13_1 | 0.06 |
| 13_2 | 0.1 |
| 14 | 0.04 |
| 14_1 | 0.02 |
| 14_2 | 0.05 |
| 15 | 0.06 |
| 15_1 | 0.2 |
| 15_2 | 0.2 |
| 16 | 0.04 |
| 16_1 | 0.03 |
| 16_2 | 0.08 |
| 17 | 0.01 |
| 17_1 | 0.02 |
| 17_2 | 0.006 |
| 18 | 0.06 |
| 18_1 | 0.07 |
| 18_2 | 0.02 |
| 19 | 0.1 |
| 19_1 | 0.3 |
| 19_2 | 0.3 |
| 20 | 0.2 |
| 20_1 | 0.06 |
| 20_2 | 0.2 |
| 21 | 0.06 |
| 21_1 | 0.1 |
| 21_2 | 0.3 |
| 22 | 0.06 |
| 22_1 | 0.04 |
| 22_2 | 0.1 |
| 23 | 0.03 |
| 24 | 0.03 |
| 24_1 | 0.01 |
| 24_2 | 0.2 |
| 25 | 0.004 |
| 25_1 | 0.002 |
| 25_2 | 0.08 |
| 26 | 0.06 |
| 26_1 | 0.04 |
| 26_2 | 0.3 |
| 27 | 0.4 |
| 28 | 0.4 |
| 29 | 0.2 |
| 30 | 0.008 |
| 31 | 0.3 |
| 32 | 0.006 |
| 33 | 0.03 |
| 34 | 0.1 |
| 35 | 0.009 |
| 36 | 0.02 |
| 36_1 | 0.01 |
| 36_2 | 0.02 |
| 37 | 0.02 |
| 38 | 0.05 |
| 38_1 | 0.05 |
| 38_2 | 0.2 |
| 39 | 0.05 |
| 40 | 0.1 |

TABLE 1-continued

Median IC$_{50}$ values for the Vps34 assay

| Example Compound | Median IC50 uM Adapta |
|---|---|
| 40_1 | 0.1 |
| 40_2 | 0.1 |
| 39 | 0.05 |
| 40 | 0.1 |
| 40_1 | 0.1 |
| 40_2 | 0.1 |
| 41 | 0.01 |
| 42 | 0.03 |
| 43_1 | 0.003 |
| 43_2 | 0.1 |
| 44_1 | 0.001 |
| 44_2 | 0.006 |
| 45 | 0.003 |
| 46 | 0.005 |
| 47 | 0.006 |
| 48_1 | 0.01 |
| 48_2 | 0.02 |
| 49 | 0.03 |

Example 51

High Content Screening Autophagy Assay

Human osteosarcoma cells (HOS) stably expressing a Green Fluorescent Protein (GFP) tagged LC3 (GFP-LC3) were used to determine the inhibitory effect on autophagy of proprietary compounds. For that purpose, autophagy was activated by using the mTOR inhibitor KU-0063794 at 500 nM in the presence of Bafilomycin A1 (Sigma-Aldrich) at 5 nM. Shortly, cells were plated overnight in clear bottom 96-well plates in DMEM-High Modified media (Hi-Clone Cat #SH30285.01). At the start of the experiment, the media was removed and replaced with fresh media containing the mTOR inhibitor, Bafilomycin A1 and the vehicle or a test compound as indicated. After 6 hours the media was removed, cells were washed twice with ice-cold phosphate buffered saline (PBS) and fixed with 4% paraformaldehyde for 20 minutes at room temperature. Then the cells were washed twice with ice-cold PBS before adding Hoechst 33342 at 1 μg/ml in PBS for nuclear staining. After incubation overnight at 4° C., cells were washed once with PBS to remove the excess of dye and 100 μl of PBS was added to each well. Images were acquired at 20× magnification, 6 images per well, using the ImageXpress automated microscope (Molecular Devices Inc.) and analyzed with MetaXpress software to identify LC3-GFP foci. Foci area per cell values were used to generate dose response curves and IC50 values were calculated using the non-linear fitting analysis in GraphPad Prism software.

The tested example compounds effectively inhibited autophagy in HOS cells. The results of the assay are shown in Table 2 (Median IC$_{50}$ μM HOS-LC3).

TABLE 2

Median IC$_{50}$ values for the Vps34 assay and autophagy in HOS cells assay.

| Example Compound | Median IC50 (uM) Cellular assay |
|---|---|
| 1 | 5 |
| 3 | 13 |
| 4 | 9 |
| 5 | 15 |
| 6 | 5 |
| 7 | 0.5 |
| 8 | 10 |
| 9 | 2 |
| 13 | 2 |
| 16 | 0.3 |
| 17 | 0.1 |
| 17_2 | 0.3 |
| 18_2 | 1 |
| 24_1 | 1.4 |
| 25 | 0.02 |
| 25_1 | 0.03 |
| 26_1 | 0.2 |
| 30 | 0.6 |
| 32 | 0.3 |
| 35 | 0.7 |
| 36 | 0.03 |
| 36_1 | 0.4 |
| 36_2 | 0.7 |
| 37 | 0.3 |
| 41 | 0.08 |
| 43_1 | 0.03 |
| 44_1 | 0.2 |
| 45 | 0.1 |
| 47 | 0.09 |

The invention claimed is:

1. A process for preparing a compound represented by Formula (I):

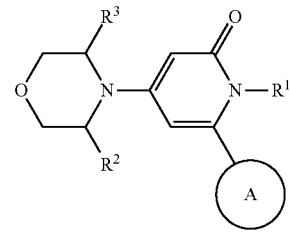

wherein

R$^1$, R$^2$ and R$^3$ are independently selected from the group consisting of hydrogen, C$_1$-C$_3$haloalkyl and C$_1$-C$_3$alkyl;

A represents

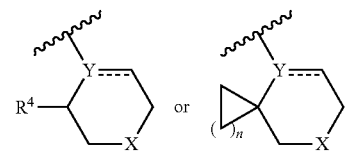

wherein

X is selected from the group consisting of CH$_2$, S, SO, SO$_2$, NR$^5$, NCOR$^5$, NCOR$^9$, NCOCH$_2$R$^9$, and a bond;

Y is selected from the group consisting of N, CH and C;

n is selected from the group consisting of 1, 2, 3 and 4;

$R^4$ is selected from the group consisting of hydrogen, halogen, $COR^6$, $C_1$-$C_6$alkyl, $C_1$-$C_3$alkoxyC$_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl and heteroaryl, wherein said aryl and said heteroaryl are optionally substituted with one or more $R^7$;

$R^5$ is selected from the group consisting of hydrogen, $C_1$-$C_3$fluoroalkyl, $C_1$-$C_3$alkyl, $C_1$-$C_3$alkoxyC$_1$-$C_3$alkyl and $C_3$-$C_6$cycloalkyl;

$R^6$ is selected from the group consisting of $C_1$-$C_3$alkoxy, N—$C_1$-$C_3$alkylamino, N,N-diC$_1$-$C_3$alkylamino, 1-pyrrolidinyl, 1-piperidinyl and 1-azetidinyl;

$R^7$ is selected from the group consisting of $C_1$-$C_6$alkyl, $C_3$-$C_6$cycloalkyl, $C_1$-$C_3$alkoxyC$_1$-$C_3$alkyl, $C_1$-$C_3$haloalkyl, halogen, N—$C_1$-$C_3$alkylamino, N,N-diC$_1$-$C_3$alkylamino, $C_1$-$C_3$haloalkoxy and $C_1$-$C_3$alkoxy;

$R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and $R^8$ is selected from the group consisting of halogen, $C_1$-$C_3$haloalkyl and $C_1$-$C_3$alkyl;

and pharmaceutically acceptable salts, stereoisomers and tautomers thereof;

the process comprising:
(i) providing a compound represented by Formula (III):

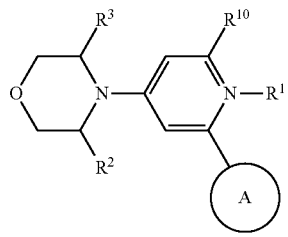

III wherein
$R^1$, $R^2$, $R^3$, and A are as defined as above;
$R^{10}$ is selected from the group consisting of F, OCH$_3$, OC(CH$_3$)$_3$, and OSiR'R"R'"; and
R', R", and R'" are each independently aryl or alkyl; and
(ii) converting the compound represented by Formula (III) into the compound represented by Formula (I).

2. The process of claim 1, wherein Y is N.

3. The process of claim 1, wherein $R^1$ and $R^3$ are independently selected from hydrogen and methyl.

4. The process of claim 1, wherein $R^2$ is hydrogen.

5. The process of claim 1, wherein $R^5$ is $C_1$-$C_3$alkyl.

6. The process of claim 1, wherein $R^6$ is dimethylamino.

7. The process of claim 1, wherein $R^7$ is selected from the group consisting of fluorine, chlorine, trifluoromethyl, trifluoromethoxy, methoxy, methyl, ethyl, cyclopropyl and dimethylamino.

8. The process of claim 1, wherein $R^9$ is selected from the group consisting of $C_1$-$C_3$alkoxy, heterocyclyl, phenyl and a monocyclic heteroaryl, wherein said heterocyclyl, said phenyl and said monocyclic heteroaryl are optionally substituted with one or two $R^8$.

9. The process of claim 1, wherein $R^9$ is selected from the group consisting of heterocyclyl, phenyl and a monocyclic heteroaryl, wherein said heterocyclyl, said phenyl and said monocyclic heteroaryl are optionally substituted with one or two $R^8$.

10. The process of claim 1, wherein said monocyclic heteroaryl in $R^4$ is selected from the group consisting of pyridyl, furyl, isoxasolyl, pyrazolyl and thiazolyl, each optionally substituted with one or more $R^7$.

11. The process of claim 1, wherein $R^7$ is selected from the group consisting of fluorine, chlorine, methyl, ethyl, methoxy, trifluoromethoxy, trifluoromethyl, cyclopropyl and N,N-dimethylamino.

12. The process of claim 1, wherein X represents a bond.

13. The process of claim 1, wherein A is selected from the group consisting of:

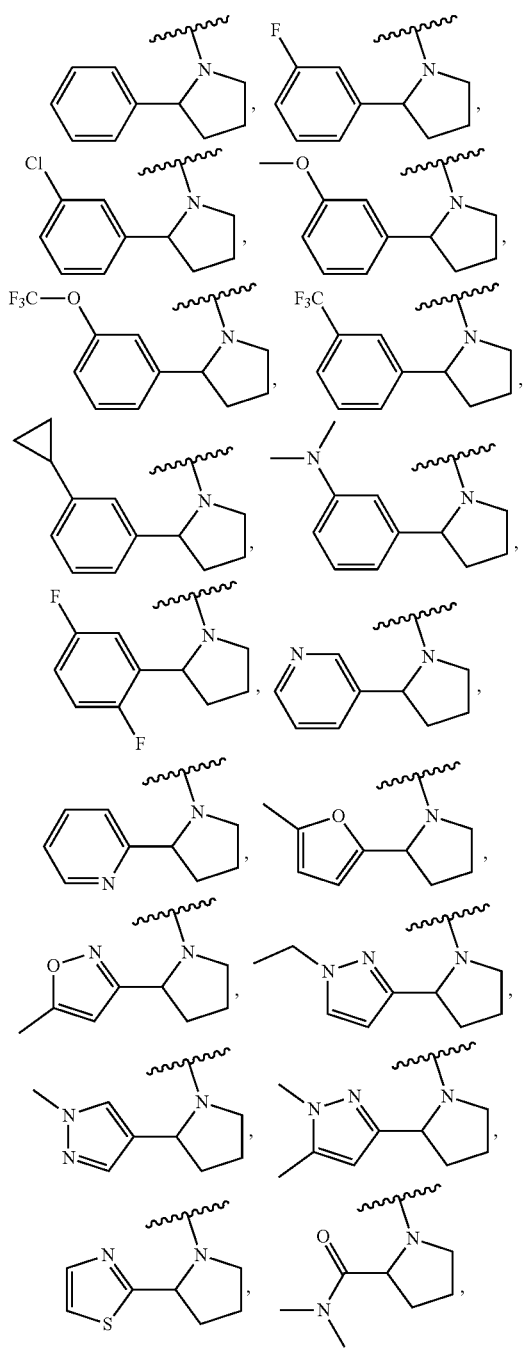

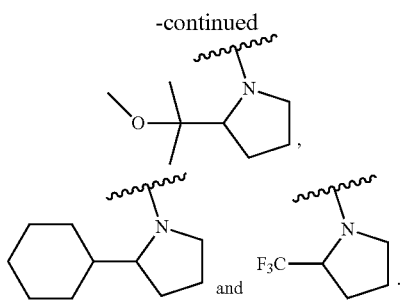

14. The process of claim 1, wherein X is selected from the group consisting of $CH_2$, SO, $SO_2$, $NR^5$, $NCOR^5$, $NCOR^9$, $NCOCH_2R^9$ and O; and $R^5$ is $C_1$-$C_3$alkyl.

15. The process of claim 1, wherein the compound is selected from the group consisting of:
   4-morpholino-6-(2-phenylpyrrolidin-1-yl)-1H-pyridin-2-one;
   1-methyl-4-morpholino-6-(2-phenylpyrrolidin-1-yl)pyridin-2-one;
   4-morpholino-6-[(2S)-2-phenylpyrrolidin-1-yl]-1H-pyridin-2-one;
   4-morpholino-6-[(2R)-2-phenylpyrrolidin-1-yl]-1H-pyridin-2-one;
   6-(3,6-dihydro-2H-pyran-4-yl)-4-(3-methylmorpholin-4-yl)-1H-pyridin-2-one;
   4-(3-methylmorpholin-4-yl)-6-tetrahydropyran-4-yl-1H-pyridin-2-one;
   6-[2-(3-methoxyphenyl)pyrrolidin-1-yl]-4-(3-methylmorpholin-4-yl)-1H-pyridin-2-one;
   4-(3-methylmorpholin-4-yl)-6-[2-(3-pyridyl)pyrrolidin-1-yl]-1H-pyridin-2-one;
   4-(3-methylmorpholin-4-yl)-6-(2-phenylpyrrolidin-1-yl)-1H-pyridin-2-one;
   N,N-dimethyl-1-[4-[(3R)-3-methylmorpholin-4-yl]-6-oxo-1H-pyridin-2-yl]pyrrolidine-2-carboxamide;
   6-[2-(1-methoxy-1-methyl-ethyl)pyrrolidin-1-yl]-4-[(3R)-3-methylmorpholin-4-yl]-1H-pyridin-2-one;
   6-(2-cyclohexylpyrrolidin-1-yl)-4-[(3R)-3-methylmorpholin-4-yl]-1H-pyridin-2-one;
   6-[2-(3-fluorophenyl)pyrrolidin-1-yl]-4-[(3R)-3-methylmorpholin-4-yl]-1H-pyridin-2-one;
   6-[2-(2,5-difluorophenyl)pyrrolidin-1-yl]-4-[(3R)-3-methylmorpholin-4-yl]-1H-pyridin-2-one;
   4-[(3R)-3-methylmorpholin-4-yl]-6-[2-[3-(trifluoromethoxy)phenyl]pyrrolidin-1-yl]-1H-pyridin-2-one;
   4-[(3R)-3-methylmorpholin-4-yl]-6-[2-[3-(trifluoromethyl)phenyl]pyrrolidin-1-yl]-1H-pyridin-2-one;
   6-[2-(3-methoxyphenyl)pyrrolidin-1-yl]-4-[(3R)-3-methylmorpholin-4-yl]-1H-pyridin-2-one;
   4-[(3R)-3-methylmorpholin-4-yl]-6-(2-phenylpyrrolidin-1-yl)-1H-pyridin-2-one;
   4-[(3R)-3-methylmorpholin-4-yl]-6-[2-(1-methylpyrazol-4-yl)pyrrolidin-1-yl]-1H-pyridin-2-one;
   6-[2-(1,5-dimethylpyrazol-3-yl)pyrrolidin-1-yl]-4-[(3R)-3-methylmorpholin-4-yl]-1H-pyridin-2-one;
   6-[2-(1-ethylpyrazol-3-yl)pyrrolidin-1-yl]-4-[(3R)-3-methylmorpholin-4-yl]-1H-pyridin-2-one;
   6-[2-(5-methyl-2-furyl)pyrrolidin-1-yl]-4-[(3R)-3-methylmorpholin-4-yl]-1H-pyridin-2-one;
   6-[2-[3-(dimethylamino)phenyl]pyrrolidin-1-yl]-4-[(3R)-3-methylmorpholin-4-yl]-1H-pyridin-2-one;
   4-[(3R)-3-methylmorpholin-4-yl]-6-(3-methylmorpholin-4-yl)-1H-pyridin-2-one;
   4-[(3R)-3-methylmorpholin-4-yl]-6-[2-(trifluoromethyl)-1-piperidyl]-1H-pyridin-2-one;
   4-[(3R)-3-methylmorpholin-4-yl]-6-(3-phenylmorpholin-4-yl)-1H-pyridin-2-one;
   4-[(3R)-3-methylmorpholin-4-yl]-6-(1-oxo-1,4-thiazinan-4-yl)-1H-pyridin-2-one;
   6-(1,1-dioxo-1,4-thiazinan-4-yl)-4-[(3R)-3-methylmorpholin-4-yl]-1H-pyridin-2-one;
   6-(4-acetylpiperazin-1-yl)-4-[(3R)-3-methylmorpholin-4-yl]-1H-pyridin-2-one;
   4-[(3R)-3-methylmorpholin-4-yl]-6-[(2R)-2-phenyl-1-piperidyl]-1H-pyridin-2-one;
   4-[(3R)-3-methylmorpholin-4-yl]-6-(4-methyl-2-phenylpiperazin-1-yl)-1H-pyridin-2-one;
   4-[(3R)-3-methylmorpholin-4-yl]-6-[3-(trifluoromethyl)morpholin-4-yl]-1H-pyridin-2-one;
   6-(3-cyclopropylmorpholin-4-yl)-4-[(3R)-3-methylmorpholin-4-yl]-1H-pyridin-2-one;
   4-[(3R)-3-methylmorpholin-4-yl]-6-[(2S)-2-(trifluoromethyl)pyrrolidin-1-yl]-1H-pyridin-2-one;
   4-[(3R)-3-methylmorpholin-4-yl]-6-[(2R)-2-(trifluoromethyl)pyrrolidin-1-yl]-1H-pyridin-2-one;
   6-[2-(3-chlorophenyl)pyrrolidin-1-yl]-4-[(3R)-3-methylmorpholin-4-yl]-1H-pyridin-2-one;
   6-[2-(3-cyclopropylphenyl)pyrrolidin-1-yl]-4-[(3R)-3-methylmorpholin-4-yl]-1H-pyridin-2-one;
   4-[(3R)-3-methylmorpholin-4-yl]-6-[2-(2-pyridyl)pyrrolidin-1-yl]-1H-pyridin-2-one;
   4-[(3R)-3-methylmorpholin-4-yl]-6-(2-thiazol-2-ylpyrrolidin-1-yl)-1H-pyridin-2-one;
   6-[2-(5-methylisoxazol-3-yl)pyrrolidin-1-yl]-4-[(3R)-3-methylmorpholin-4-yl]-1H-pyridin-2-one;
   1-methyl-4-[(3R)-3-methylmorpholin-4-yl]-6-[(2R)-2-(trifluoromethyl)-1-piperidyl]pyridin-2-one; and
   4-[(3R)-3-methylmorpholin-4-yl]-6-(8-oxa-5-azaspiro[3.5]nonan-5-yl)-1H-pyridin-2-one;
   6-[2-(3-methoxyphenyl)-1-piperidyl]-4-[(3R)-3-methylmorpholin-4-yl]-1H-pyridin-2-one;
   6-[4-acetyl-2-(trifluoromethyl)piperazin-1-yl]-4-[(3R)-3-methylmorpholin-4-yl]-1H-pyridin-2-one;
   6-[4-(5-fluoropyridine-3-carbonyl)-2-(trifluoromethyl)piperazin-1-yl]-4-[(3R)-3-methylmorpholin-4-yl]-1H-pyridin-2-one;
   6[4-[2-(4-fluorophenyl)acetyl]-2-(trifluoromethyl)piperazin-1-yl]-4-[(3R)-3-methylmorpholin-4-yl]-1H-pyridin-2-one;
   4-[(3R)-3-methylmorpholin-4-yl]-6-[4-(tetrahydrofuran-2-carbonyl)-2-(trifluoromethyl)piperazin-1-yl]-1H-pyridin-2-one;
   4-[(3R)-3-methylmorpholin-4-yl]-6-[4-methyl-2-(trifluoromethyl)piperazin-1-yl]-1H-pyridin-2-one; and pharmaceutically acceptable salts, tautomers and stereoisomers thereof.

16. The process of claim 1, wherein:
   (a) when $R^{10}$ is F, converting the compound of Formula (III) comprises carrying out acidic hydrolysis of the compound of Formula (III);
   (b) when $R^{10}$ is $OCH_3$, converting the compound of Formula (III) comprises reacting the compound of Formula (III) with trimethylsilyl iodide in a suitable solvent, reacting the compound of Formula (III) with HBr in a suitable solvent, or reacting the compound of Formula (III) with $BBr_3$ in a suitable solvent;
   (c) when $R^{10}$ is $OC(CH_3)_3$, converting the compound of Formula (III) comprises reacting the compound of Formula (III) with trifluoroacetic acid in a suitable solvent; or (d) when R¹⁰ is OSiR'R''R''', converting the compound of Formula (III) comprises reacting the compound of Formula (III) with HCl in a suitable solvent or by reacting the compound of Formula (III) with tetrabutyl ammonium fluoride in tetrahydrofuran.

17. The process of claim 1, wherein each of R', R'', and R''' is independently selected from the group consisting of phenyl, methyl, and tert-butyl.

18. The process of claim 1, further comprising:
reacting a compound represented by Formula (II):

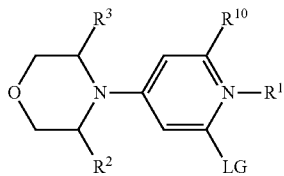

II wherein $R^1$, $R^2$, $R^3$, and $R^{10}$ are as defined as in claim 1; and

LG is a leaving group;

with a coupling partner represented by:

to produce the compound of Formula (III), wherein reaction of the coupling partner with the LG of the compound of Formula II produces A as defined in claim 1, wherein the coupling partner is a boronic acid or a boronic acid derivative bound to A or is A as a free base or a salt thereof.

19. The process of claim 18, wherein LG is halogen.

20. The process of claim 18, comprising reacting the compound of Formula (II) with the coupling partner in the presence of a metal catalyst.

\* \* \* \* \*